US008173653B2

(12) United States Patent
Dorsch et al.

(10) Patent No.: US 8,173,653 B2
(45) Date of Patent: May 8, 2012

(54) PYRIDIAZINONE DERIVATIVES FOR THE TREATMENT OF TUMOURS

(75) Inventors: Dieter Dorsch, Ober-Ramstadt (DE); Oliver Schadt, Rodenbach (DE); Andree Blaukat, Muehltal (DE)

(73) Assignee: Merck Patent Gesellschaft MIT Beschraenkter Haftung, Darmstadt (DE)

( * ) Notice: Subject to any disclaimer, the term of this patent is extended or adjusted under 35 U.S.C. 154(b) by 990 days.

(21) Appl. No.: 12/096,079

(22) PCT Filed: Nov. 7, 2006

(86) PCT No.: PCT/EP2006/010668
§ 371 (c)(1),
(2), (4) Date: Jun. 4, 2008

(87) PCT Pub. No.: WO2007/065518
PCT Pub. Date: Jun. 14, 2007

(65) Prior Publication Data
US 2008/0293719 A1 Nov. 27, 2008

(30) Foreign Application Priority Data
Dec. 5, 2005 (DE) .......................... 10 2005 057 924

(51) Int. Cl.
*A01N 43/58* (2006.01)
*A61K 31/50* (2006.01)
*C07D 237/02* (2006.01)

(52) U.S. Cl. ........................................ 514/247; 544/224
(58) Field of Classification Search .................. 544/224, 544/247; 514/247, 224
See application file for complete search history.

(56) References Cited

U.S. PATENT DOCUMENTS

| 5,753,642 | A | 5/1998 | Michelotti et al. |
| 7,060,822 | B1 | 6/2006 | Arnold et al. |
| 2004/0259863 | A1 | 12/2004 | Eggenweiler et al. |
| 2007/0027116 | A1 | 2/2007 | Cho et al. |

FOREIGN PATENT DOCUMENTS

| EP | 0478195 A1 | 4/1992 |
| RO | 79562 B | 8/1982 |
| RO | 79566 B | 8/1982 |
| WO | WO 0109121 A3 | 2/2001 |
| WO | WO 03004494 A1 | 1/2003 |
| WO | WO 03037349 A | 5/2003 |
| WO | WO 2004100960 A2 | 11/2004 |
| WO | WO 2006095666 A1 | 9/2006 |

OTHER PUBLICATIONS

Goekce et al., Synthesis of new Mannich bases of arylpyridazinones as analgesic and anti-inflammatory agents. Arzneimittel Forschung (2005), 55(6), 318-325 CODEN: ARZNAD; ISSN: 0004-4172.*
Salives et al., Journal of Combinatorial Chemistry (2005), 7(3), 414-420.*
Salives R. et al, "Solid-phase syntheses of 6-arylpyridazin-3(2H)-ones", Journal of Combinatorial Chemistry, 7(3), pp. 414-420, Mar. 23, 2005, XP002423455.
Fontaine F. et al, "Incorporating molecular shape into the alignment-free Grid-Independent Descriptors", Journal of Medicinal Chemistry, American Chemical Society, Washington DC, Bd. 47 Nr. 11, 24, Apr. 24, 2004, 2805-2815, XP002410361.
Colletti S. L. et al, "Hybrid-designed inhibitors of p38 MAP kinase utilizing N-arylpyridazinones", Journal of Medicinal Chemistry, American Chemical Society, Washington DC, Bd. 46, 2003, 349-352, XP002966978.

* cited by examiner

*Primary Examiner* — Paul V. Ward
(74) *Attorney, Agent, or Firm* — Millen, White, Zelano & Branigan, P.C.

(57) ABSTRACT

Compounds of the formula (I), in which $R^1$, $R^2$ and $R^3$ have the meanings indicated in claim 1, are inhibitors of tyrosine kinases, in particular Met kinase, and can be employed, inter alia, for the treatment of tumors.

16 Claims, 1 Drawing Sheet

Effect of "A56" and "A91" on the growth of TPR - Met / NIH 3T3 cells in Baln C nude mice.
Number of cells: $4\times10^6$ cells/mouse; date of cell injection: 30.06.06.
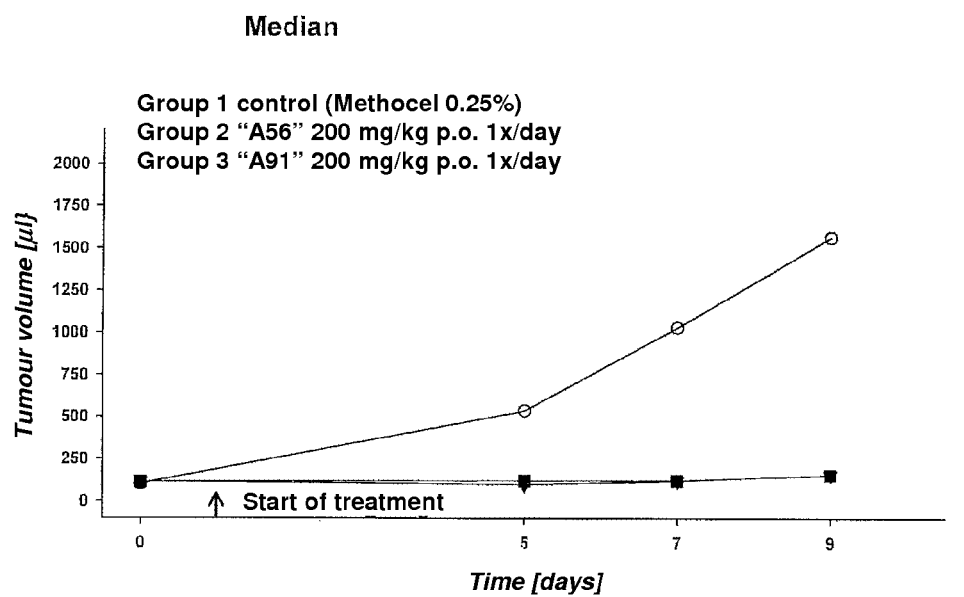
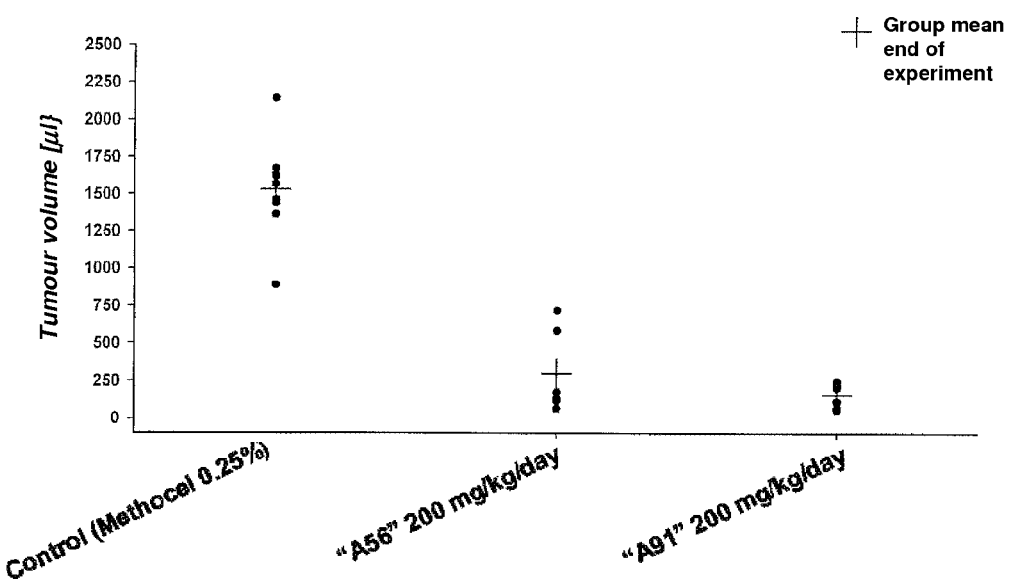

PYRIDIAZINONE DERIVATIVES FOR THE TREATMENT OF TUMOURS

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases and/or serine/threonine kinases, plays a role, furthermore to pharmaceutical compositions which comprise these compounds, and to the use of the compounds for the treatment of kinase-induced diseases.

In particular, the present invention relates to compounds and to the use of compounds in which the inhibition, regulation and/or modulation of signal transduction by Met kinase plays a role.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The role of the receptor tyrosine kinase Met in human oncogenesis and the possibility of inhibition of HGF (hepatocyte growth factor)-dependent Met activation are described by S. Berthou et al. in Oncogene, Vol. 23, No. 31, pages 5387-5393 (2004). The inhibitor SU11274 described therein, a pyrrole-indoline compound, is potentially suitable for combating cancer. Another Met kinase inhibitor for cancer therapy is described by J. G. Christensen et al. in Cancer Res. 2003, 63(21), 7345-55.

A further tyrosine kinase inhibitor for combating cancer is reported by H. Hov et al. in Clinical Cancer Research Vol. 10, 6686-6694 (2004). The compound PHA-665752, an indole derivative, is directed against the HGF receptor c-Met. It is furthermore reported therein that HGF and Met make a considerable contribution to the malignant process of various forms of cancer, such as, for example, multiple myeloma.

The synthesis of small compounds which specifically inhibit, regulate and/or modulate signal transduction by tyrosine kinases and/or serine/threonine kinases, in particular Met kinase, is therefore desirable and an aim of the present invention.

It has been found that the compounds according to the invention and salts thereof have very valuable pharmacological properties while being well tolerated.

The present invention specifically relates to compounds of the formula I which inhibit, regulate and/or modulate signal transduction by Met kinase, to compositions which comprise these compounds, and to processes for the use thereof for the treatment of Met kinase-induced diseases and complaints such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, trans-plant rejection, metabolic diseases and diseases of the immune system, also autoimmune diseases, cirrhosis, diabetes and diseases of the blood vessels, also instability and permeability and the like in mammals.

Solid tumours, in particular fast-growing tumours, can be treated with Met kinase inhibitors. These solid tumours include monocytic leukaemia, brain, urogenital, lymphatic system, stomach, laryngeal and lung carcinoma, including lung adenocarcinoma and small-cell lung carcinoma.

The present invention is directed to processes for the regulation, modulation or inhibition of Met kinase for the prevention and/or treatment of diseases in connection with unregulated or disturbed Met kinase activity. In particular, the compounds of the formula I can also be employed in the treatment of certain forms of cancer. The compounds of the formula I can furthermore be used to provide additive or synergistic effects in certain existing cancer chemotherapies, and/or can be used to restore the efficacy of certain existing cancer chemotherapies and radiotherapies.

The compounds of the formula I can furthermore be used for the isolation and investigation of the activity or expression of Met kinase. In addition, they are particularly suitable for use in diagnostic methods for diseases in connection with unregulated or disturbed Met kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit trans-plant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-anti-bodies (phospho-ABs). The phospho-AB binds only the phosphorylated substrate. This binding can be detected by chemiluminescence using a second peroxidase-conjugated anti-sheep antibody (Ross et al., 2002, Biochem. J.).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

Dihydropyridazinones for combating cancer are described in WO 03/037349 A1.

Other pyridazines for the treatment of diseases of the immune system, ischaemic and inflammatory diseases are known from EP 1 043 317 A1 and EP 1 061 077 A1.

EP 0 738 716 A2 and EP 0 711 759 B1 describe other dihydropyridazinones and pyridazinones as fungicides and insecticides.

Other pyridazinones are described as cardiotonic agents in U.S. Pat. No. 4,397,854. JP 57-95964 discloses other pyridazinones.

SUMMARY OF THE INVENTION

The invention relates to compounds of the formula I

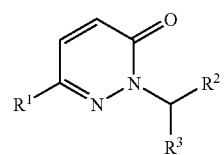

in which
$R^1$ denotes $Ar^1$ or Het,
$R^2$ denotes $Ar^2$ or $Het^2$,
$R^3$ denotes H or A,
A denotes unbranched or branched alkyl having 1-10 C atoms, in which 1-7H atoms may be replaced by F, Cl and/or Br, and/or in which one or two $CH_2$ groups may be replaced by O, S, SO, $SO_2$ and/or CH=CH groups, or cyclic alkyl having 3-7 C atoms,
$Ar^1$ denotes phenyl, naphthyl or biphenyl, each of which is unsubstituted or mono-, di- or trisubstituted by Hal, A, $OR^3$, $N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, CO-$Het^1$, $Het^1$, $O[C(R^3)_2]_nN(R^3)$, $O[C(R^3)_2]_nHet^1$, NHCOOA, $NHCON(R^3)_2$, $NHCOO[C(R^3)_2]_nN(R^3)_2$, NHCOO$[C(R^3)_2]_pHet^1$, $NHCONH[C(R^3)_2]_nN(R^3)_2$, NHCONH[$C(R^3)_2]_pHet^1$, $OCONH[C(R^3)_2]_nN(R^3)_2$, OCONH$[C(R^3)_2]_nHet^1$, CHO and/or COA,
$Ar^2$ denotes phenyl, naphthyl or biphenyl, each of which is mono-, di- or trisubstituted by Hal, A, $OR^3$, $N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, CO-$Het^1$, $Het^1$, $O[C(R^3)_2]_nN(R^3)$, $O[C(R^3)_2]_nHet^1$, NHCOOA, $NHCON(R^3)_2$, NHCOO$[C(R^3)_2]_nN(R^3)_2$, $NHCOO[C(R^3)_2]_pHet^1$, NHCONH$[C(R^3)_2]_nN(R^3)_2$, $NHCONH[C(R^3)_2]_pHet^1$, OCONH$[C(R^3)_2]_nN(R^3)_2$, OCONH$[C(R^3)_2]_nHet^1$, CHO and/or COA,
Het, $Het^2$ each, independently of one another, denote a mono-, bi- or tricyclic saturated, unsaturated or aromatic heterocycle having 1 to 4 N, O and/or S atoms, which may be unsubstituted or mono-, di- or trisubstituted by Hal, A, $OR^3$, $(CH_2)_pN(R^3)_2$, $SR^3$, $NO_2$, CN, $COOR^3$, $CON(R^3)_2$, $O[C(R^3)_2]_nN(R^3)$, $O[C(R^3)_2]_nHet^1$, NHCOOA, NHCON$(R^3)_2$, NHCOO$[C(R^3)_2]_nN(R^3)_2$, NHCOO$[C(R^3)_2]_nHet^1$, NHCONH$[C(R^3)_2]_nN(R^3)_2$, NHCONH$[C(R^3)_2]_nHet^1$, OCONH$[C(R^3)_2]_nN(R^3)_2$, OCONH$[C(R^3)_2]_nHet^1$, $NR^3COA$, $NR^3SO_2A$, $SO_2N(R^3)_2$, $S(O)_mA$, CO-$Het^1$, CHO, COA, =S, =NH, =NA, oxy (—$O^-$) and/or =O (carbonyl oxygen), Het¹ denotes a monocyclic saturated or aromatic heterocycle having 1 to 2 N and/or O atoms, which may be mono- or disubstituted by A, OA, OH, Hal and/or =O (carbonyl oxygen), Hal denotes F, Cl, Br or I, m denotes 0, 1 or 2, n denotes 1, 2, 3 or 4, p denotes 0, 1, 2, 3 or 4, and pharmaceutically usable derivatives, solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to Claims 1-11 and pharmaceutically usable derivatives, salts, solvates and stereoisomers thereof, characterised in that a) a compound of the formula II

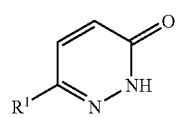

in which $R^1$ has the meaning indicated in Claim 1, is reacted with a compound of the formula III

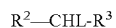

$$R^2\text{—CHL-}R^3 \qquad \text{III,}$$

in which $R^2$ and $R^3$ have the meanings indicated in Claim 1 and

L denotes Cl, Br, I or a free or reactively functionally modified OH group, or b) a radical $R^2$ is converted into another radical $R^2$ by acylating an amino group, or c) it is liberated from one of its functional derivatives by treatment with a solvolysing or hydrogenolysing agent, and/or a base or acid of the formula I is converted into one of its salts.

Above and below, the radicals $R^1$, $R^2$ and $R^3$ have the meanings indicated for the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl (cycloalkyl) preferably denotes cyclopropyl, cyclobutyl, cyclopentyl, cyclohexyl or cycloheptyl.

$Ar^1$ denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or paminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylaminopropyl)ureido]phenyl, o-, m- or p-(3-diethylaminopropoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6- methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

In a further embodiment, $Ar^1$ preferably denotes phenyl which is unsubstituted or mono-, di- or trisubstituted by Hal, A, $OR^3$, CN, $CONH_2$, $O[C(R^3)_2]_nN(R^3)_2$ and/or $O[C(R^3)_2]_nHet^1$.

$Ar^2$ denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylaminopropyl)ureido]phenyl, o-, m- or p-(3-diethylaminopropoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

In a further embodiment, $Ar^2$ preferably denotes phenyl which is mono-, di- or trisubstituted by $N(R^3)_2$, CN, COOA, COOH, OH, OA, $NR^3COA$, NHCOOA, $NHCON(R^3)_2$, $NHCOO[C(R^3)_2]_nN(R^3)_2$, $OCONH[C(R^3)_2]_nN(R^3)_2$, $NHCOO[C(R^3)_2]_nOR^3$, $NHCOO(CH_2)_nO(CH_2)_nOR^3$, $NHCOO[C(R^3)_2]_pHet^1$, $NHCONH[C(R^3)_2]_nN(R^3)_2$ and/or $NHCONH[C(R^3)_2]_pHet^1$.

$Ar^2$ particularly preferably denotes phenyl which is substituted in the 3-position by $N(R^3)_2$, CN, COOA, COOH, OH, OA, $NR^3COA$, NHCOOA, $NHCON(R^3)_2$, $NHCOO[C(R^3)_2]_nN(R^3)_2$, $OCONH[C(R^3)_2]_nN(R^3)_2$, $NHCOO[C(R^3)_2]_nOR^3$, $NHCOO(CH_2)_nO(CH_2)_nOR^3$, $NHCOO[C(R^3)_2]_pHet^1$, $NHCONH[C(R^3)_2]_nN(R^3)_2$ or $NHCONH[C(R^3)_2]_pHet^1$.

$Ar^2$ very particularly preferably denotes phenyl which is monosubstituted in the 3-position by $NHCOO[C(R^3)_2]_nN(R^3)_2$ or $NHCOO[C(R^3)_2]_pHet^1$, where
$R^3$ preferably denotes H or methyl,
$Het^1$ preferably denotes morpholin-4-yl,
n preferably denotes 2, 3 or 4 and
p preferably denotes 2 or 3.

Irrespective of further substitutions, Het and $Het^2$ each, independently of one another, denote, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl or dibenzofuranyl. The heterocyclic radicals may also be partially or fully hydrogenated. Irrespective of further substitutions, Het and $Het^2$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8- 3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1Hquinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

In a further embodiment, Het preferably denotes a mono- or bicyclic aromatic heterocycle having 1 to 3 N, O and/or S atoms, which may be un-substituted or mono-, di- or trisubstituted by Hal.

Het particularly preferably denotes thiazolyl, thienyl, pyridyl, benzo-1,2,5-thiadiazolyl or benzo-1,3-dioxolyl.

$Het^1$ preferably denotes a monocyclic saturated or aromatic heterocycle having 1 to 2 N and/or O atoms, which may be mono- or disubstituted by A. $Het^1$ particularly preferably denotes piperidin-1-yl, pyrrolidin-1-yl, morpholin-4-yl, piperazin-1-yl, 1,3-oxazolidin-3-yl, imidazolidinyl, oxazolyl, thiazolyl, thienyl, furanyl or pyridyl, where the radicals may also be mono- or disubstituted by A.

$Het^2$ preferably denotes a mono-, bi- or tricyclic unsaturated or aromatic heterocycle having 1 to 4 N, O and/or S atoms, which may be unsubstituted or mono-, di- or trisubstituted by $OR^3$, $(CH_2)_pN(R^3)_2$, oxy ($—O^-$) and/or $=O$ (carbonyl oxygen).

Het² particularly preferably denotes benzimidazole, benzotriazole, pyridine, benzo-1,3-dioxole or benzo-2,1,3-thiadiazole, each of which may be unsubstituted or mono-, di- or trisubstituted by OR³, oxy (—O⁻) and/or $(CH_2)_pN(R^3)_2$, where R³ preferably denotes H, methyl, ethyl, propyl or isopropyl.

R¹ preferably denotes

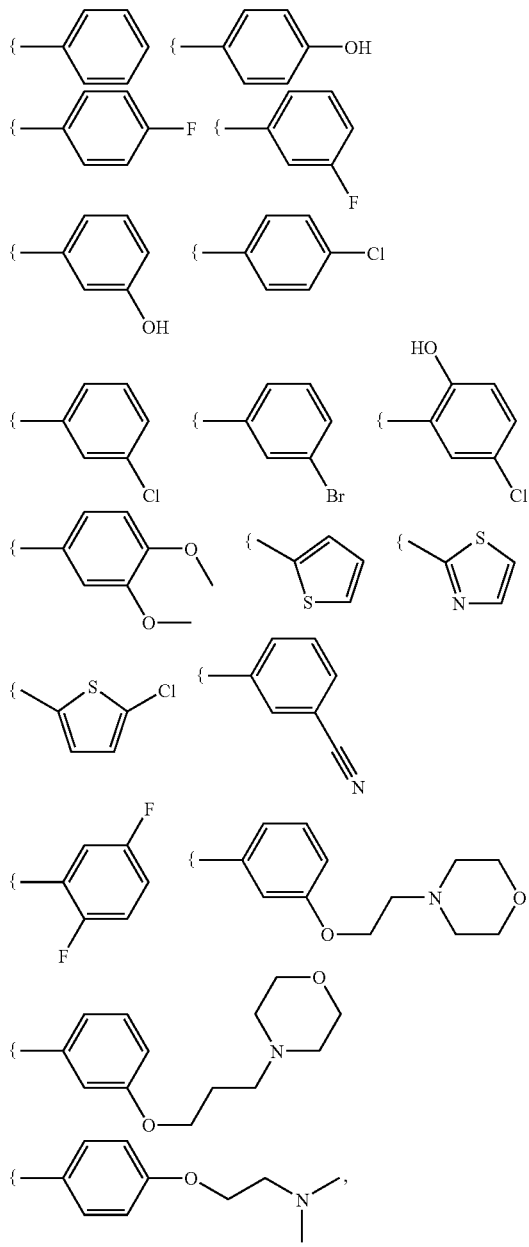

3,5-difluorophenyl, 3,4-difluorophenyl, 2,3-difluorophenyl, 3,4,5-trifluorophenyl, 3- or 4-cyanophenyl, 3,5-dichlorophenyl, pyridyl, benzo-1,2,5-thiadiazolyl or benzo-1,3-dioxolyl.

R¹ very particularly preferably denotes 3,5-difluorophenyl, 3,4-difluorophenyl, 2,3-difluorophenyl or 3,4,5-trifluorophenyl.

R³ preferably denotes H, methyl, ethyl, propyl or isopropyl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to In, which conform to the formula I and in which the radicals not designated in greater detail have the meaning indicated for the formula I, but in which in Ia A denotes unbranched or branched alkyl having 1-10 C atoms,
  in which 1-7H atoms may be replaced by F and/or Cl;
in Ib Ar¹ denotes phenyl which is unsubstituted or mono-, di- or trisubstituted by Hal, A, OR³, CN, CONH₂, $O[C(R^3)_2]_n$—$N(R^3)_2$ and/or $O[C(R^3)_2]_n$Het¹;
in Ic Het denotes a mono- or bicyclic aromatic heterocycle having 1 to 3 N, O and/or S atoms, which may be unsubstituted or mono-, di- or trisubstituted by Hal;
in Id Het denotes thiazolyl, thienyl, pyridyl, benzo-1,2,5-thiadiazolyl or benzo-1,3-dioxolyl;
in Ie Ar² denotes phenyl which is mono-, di- or trisubstituted by N(R³)₂, CN, COOA, COOH, OH, OA, NR³COA, NHCOOA, NHCON(R³)₂, NHCOO$[C(R^3)_2]_n$N(R³)₂, OCONH$[C(R^3)_2]_n$N(R³)₂, NHCOO$[C(R^3)_2]_n$OR³, NHCOO(CH₂)ₙO(CH₂)ₙOR³, NHCOO$[C(R^3)_2]_p$Het¹, NHCONH$[C(R^3)_2]_n$N(R³)₂ and/or NHCONH$[C(R^3)_2]_p$Het¹;
in If Ar² denotes phenyl which is monosubstituted in the 3-position by N(R³)₂, CN, COOA, COOH, OH, OA, NR³COA, NHCOOA, NHCON(R³)₂, NHCOO$[C(R^3)_2]_n$—N(R³)₂, OCONH$[C(R^3)_2]_n$N(R³)₂, NHCOO$[C(R^3)_2]_n$OR³NHCOO(CH₂)ₙO(CH₂)ₙOR³, NHCOO$[C(R^3)_2]_p$Het¹, NHCONH$[C(R^3)_2]_n$N(R³)₂ or NHCONH$[C(R^3)_2]_p$Het¹;
in Ig Het² denotes a mono-, bi- or tricyclic unsaturated or aromatic heterocycle having 1 to 4 N, O and/or S atoms, which may be unsubstituted or mono-, di- or trisubstituted by OR³, $(CH_2)_pN(R^3)_2$, oxy (—O⁻) and/or =O (carbonyl oxygen);
in Ih Het² denotes benzimidazole, benzotriazole, pyridine, benzo-1,3-dioxole or benzo-2,1,3-thiadiazole, each of which may be unsubstituted or mono-, di- or trisubstituted by OR³, oxy (—O⁻) and/or $(CH_2)_pN(R^3)_2$, where R³ denotes H, methyl, ethyl, propyl or isopropyl;
in Ii Het¹ denotes a monocyclic saturated or aromatic heterocycle having 1 to 2 N and/or O atoms, which may be mono- or disubstituted by A;
in Ij Het¹ denotes piperidin-1-yl, pyrrolidin-1-yl, morpholin-4-yl, piperazin-1-yl, 1,3-oxazolidin-3-yl, imidazolidinyl, oxazolyl, thiazolyl, thienyl, furanyl or pyridyl, where the radicals may also be mono- or disubstituted by A;
in Ik R¹ denotes Ar¹ or Het,
  R² denotes Ar² or Het²,
  R³ denotes H or A,
  A denotes unbranched or branched alkyl having 1-10 C atoms, in which 1-7H atoms may be replaced by F and/or Cl,
  Ar¹ denotes phenyl which is unsubstituted or mono-, di- or trisubstituted by Hal, A, OR³, CN, CONH₂, $O[C(R^3)_2]_n$—N(R³)₂ and/or $O[C(R^3)_2]_n$Het¹, Het denotes a mono- or bicyclic aromatic heterocycle having 1 to 3 N, O and/or S atoms, which may be unsubstituted or mono-, di- or trisubstituted by Hal, $Ar^2$ denotes phenyl which is mono-, di- or trisubstituted by $N(R^3)_2$, CN, COOA, COOH, OH, OA, $NR^3COA$, NHCOOA, $NHCON(R^3)_2$, $NHCOO[C(R^3)_2]_nN(R^3)_2$, $OCONH[C(R^3)_2]_nN(R^3)_2$, $NHCOO[C(R^3)_2]_nOR^3NHCOO(CH_2)_nO(CH_2)_nOR^3$, $NHCOO[C(R^3)_2]_pHet^1$, $NHCONH[C(R^3)_2]_nN(R^3)_2$ and/or $NHCONH[C(R^3)_2]_pHet^1$, $Het^2$ denotes a mono-, bi- or tricyclic unsaturated or aromatic heterocycle having 1 to 4 N, O and/or S atoms, which may be unsubstituted or mono-, di- or trisubstituted by $OR^3$, $(CH_2)_pN(R^3)_2$, oxy ($—O^-$) and/or $=O$ (carbonyl oxygen), $Het^1$ denotes a monocyclic saturated or aromatic heterocycle having 1 to 2 N and/or O atoms, which may be mono- or disubstituted by A, Hal denotes F, Cl, Br or I, n denotes 1, 2, 3 or 4, p denotes 0, 1, 2, 3 or 4;

in II $R^1$ denotes $Ar^1$ or Het, $R^2$ denotes $Ar^2$ or $Het^2$, $R^3$ denotes H or A, A denotes unbranched or branched alkyl having 1-6 C atoms,
in which 1-7H atoms may be replaced by F and/or Cl, $Ar^1$ denotes phenyl which is unsubstituted or mono-, di- or trisubstituted by Hal, A, $OR^3$, CN, $CONH_2$, $O[C(R^3)_2]_n—N(R^3)_2$ and/or $O[C(R^3)_2]_nHet^1$, Het denotes a mono- or bicyclic aromatic heterocycle having 1 to 3 N, O and/or S atoms, which may be unsubstituted or mono-, di- or trisubstituted by Hal, $Ar^2$ denotes phenyl which is substituted in the 3-position by $N(R^3)_2$, CN, COOA, COOH, OH, OA, $NR^3COA$, NHCOOA, $NHCON(R^3)_2$, $NHCOO[C(R^3)_2]_nN(R^3)_2$, $OCONH[C(R^3)_2]_nN(R^3)_2$, $NHCOO[C(R^3)_2]_nOR^3NHCOO(CH_2)_nO(CH_2)_nOR^3$, $NHCOO[C(R^3)_2]_pHet^1$, $NHCONH[C(R^3)_2]_nN(R^3)_2$ or $NHCONH[C(R^3)_2]_pHet^1$, $Het^2$ denotes a mono-, bi- or tricyclic unsaturated or aromatic heterocycle having 1 to 4 N, O and/or S atoms, which may be unsubstituted or mono-, di- or trisubstituted by $OR^3$, $(CH_2)_pN(R^3)_2$, oxy ($—O^-$) and/or $=O$ (carbonyl oxygen), $Het^1$ denotes a monocyclic saturated or aromatic heterocycle having 1 to 2 N and/or O atoms, which may be mono- or disubstituted by A, Hal denotes F, Cl, Br or I, n denotes 1, 2, 3 or 4, p denotes 0, 1, 2, 3 or 4;

in Im $R^1$ denotes $Ar^1$ or Het, $R^2$ denotes $Ar^2$ or $Het^2$, $R^3$ denotes H or A, A denotes unbranched or branched alkyl having 1-6 C atoms,
in which 1-7H atoms may be replaced by F and/or Cl, $Ar^1$ denotes phenyl which is unsubstituted or mono-, di- or trisubstituted by Hal, A, $OR^3$, CN, $CONH_2$, $O[C(R^3)_2]_n—N(R^3)_2$ and/or $O[C(R^3)_2]_nHet^1$, Het denotes thiazolyl, thienyl, pyridyl, benzo-1,2,5-thiadiazolyl or benzo-1,3-dioxolyl, $Ar^2$ denotes phenyl which is substituted in the 3-position by $N(R^3)_2$, CN, COOA, COOH, OH, OA, $NR^3COA$, NHCOOA, $NHCON(R^3)_2$, $NHCOO[C(R^3)_2]_nN(R^3)_2$, $OCONH[C(R^3)_2]_nN(R^3)_2$, $NHCOO[C(R^3)_2]_nOR^3NHCOO(CH_2)_nO(CH_2)_nOR^3$, $NHCOO[C(R^3)_2]_pHet^1$, $NHCONH[C(R^3)_2]_nN(R^3)_2$ or $NHCONH[C(R^3)_2]_pHet^1$, $Het^2$ denotes benzimidazole, benzotriazole, pyridine, benzo-1,3-dioxole or benzo-2,1,3-thiadiazole, each of which may be unsubstituted or mono-, di- or trisubstituted by $OR^3$, oxy ($—O^-$) and/or $(CH_2)_pN(R^3)_2$, where $R^3$ denotes H, methyl, ethyl, propyl or isopropyl, $Het^1$ denotes piperidin-1-yl, pyrrolidin-1-yl, morpholin-4-yl, piperazin-1-yl, 1,3-oxazolidin-3-yl, imidazolidinyl, oxazolyl, thiazolyl, thienyl, furanyl or pyridyl, where the radicals may also be mono- or disubstituted by A, Hal denotes F, Cl, Br or I, n denotes 1, 2, 3 or 4, p denotes 0, 1, 2, 3 or 4;

in In $R^1$ denotes 3,5-difluorophenyl, 3,4-difluorophenyl, 2,3-difluorophenyl or 3,4,5-trifluorophenyl, $R^2$ denotes $Ar^2$ or $Het^2$, $R^3$ denotes H or A, A denotes unbranched or branched alkyl having 1-6 C atoms,
in which 1-7H atoms may be replaced by F and/or Cl, $Ar^2$ denotes phenyl which is substituted in the 3-position by $NHCOO[C(R^3)_2]_nN(R^3)_2$ or $NHCOO[C(R^3)_2]_pHet^1$, where
$R^3$ denotes H or methyl,
$Het^1$ denotes morpholin-4-yl,
n denotes 2, 3 or 4 and
p denotes 2 or 3, $Het^2$ denotes benzimidazole, benzotriazole, pyridine, benzo-1,3-dioxole or benzo-2,1,3-thiadiazole, which may be unsubstituted or mono-, di- or trisubstituted by $OR^3$, oxy ($—O^-$) and/or $(CH_2)_pN(R^3)_2$, where $R^3$ denotes H, methyl, ethyl, propyl or isopropyl, $Het^1$ denotes piperidin-1-yl, pyrrolidin-1-yl, morpholin-4-yl, piperazin-1-yl, 1,3-oxazolidin-3-yl, imidazolidinyl, oxazolyl, thiazolyl, thienyl, furanyl or pyridyl, where the radicals may also be mono- or disubstituted by A, Hal denotes F, Cl, Br or I, n denotes 1, 2, 3 or 4, p denotes 0, 1, 2, 3 or 4;

and pharmaceutically usable derivatives, salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae II and III are generally known. If they are novel, however, they can be prepared by methods known per se. The pyridazinones of the formula II used are, if not commercially available, generally prepared by the method of W. J. Coates, A. McKillop, Synthesis, 1993, 334-342.

Compounds of the formula I can preferably be obtained by reacting a compound of the formula II with a compound of the formula III.

In the compounds of the formula II, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

It is furthermore possible to convert a compound of the formula I into another compound of the formula I by converting a radical $R^2$ into another radical $R^2$, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' is an amino-protecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" is a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 300 (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of His, Asn and Gln is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-300 and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di(($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be pre-pared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base.

Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios,
and an effective amount of a further medicament active ingredient in dissolved or lyophilised form.

Use

The present compounds are suitable as pharmaceutical active ingredients for mammals, especially for humans, in the treatment of tyrosine kinaseinduced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to Claim 1 according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer, in particular fast-growing tumours.

The invention thus relates to the use of compounds of the formula I, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to Met kinase.

Preference is given to the use of compounds of the formula I, and pharmaceutically usable derivatives, solvates and stereoisomers thereof, including mixtures thereof in all ratios, for the preparation of a medicament for the treatment of diseases which are influenced by inhibition of tyrosine kinases by the compounds according to Claim 1.

Particular preference is given to the use for the preparation of a medicament for the treatment of diseases which are influenced by inhibition of met-kinase by the compounds according to Claim 1.

Especial preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myelotic leukaemia, chronic myelotic leukaemia, acute lymphatic leukaemia and/or chronic lymphatic leukaemia.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chlorambucil, busulphan and nitrosoureas); anti-metabolites (for example antifolates such as fluoropyrimidines like 5-fluorouracil and tegafur, raltitrexed, methotrexate, cytosine arabinoside, hydroxyurea and gemcitabine); anti-tumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholino-propoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokinetransfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson |
| | Tetraplatin | Matthey) |
| | Ormiplatin | BBR-3464 |
| | Iproplatin | (Hoffmann-La Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |

TABLE 1-continued

| | | |
|---|---|---|
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxo-rubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | Cemadotin (BASF) | ER-86526 (Eisai) |
| | RPR 109881A (Aventis) | Combretastatin A4 (BMS) |
| | TXD 258 (Aventis) | Isohomohalichondrin-B (PharmaMar) |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-Benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |

TABLE 1-continued

| | | |
|---|---|---|
| Pump inhibitors | CBT-1 (CBA Pharma)<br>Tariquidar (Xenova)<br>MS-209 (Schering AG) | Zosuquidar<br>trihydrochloride (Eli Lilly)<br>Biricodar dicitrate (Vertex) |
| Histone acetyl<br>transferase inhibitors | Tacedinaline (Pfizer)<br>SAHA (Aton Pharma)<br>MS-275 (Schering AG) | Pivaloyloxymethyl butyrate<br>(Titan)<br>Depsipeptide (Fujisawa) |
| Metalloproteinase<br>inhibitors | Neovastat (Aeterna Laboratories)<br>Marimastat (British Biotech) | CMT-3 (CollaGenex)<br>BMS-275291 (Celltech) |
| Ribonucleoside<br>reductase inhibitors | Gallium maltolate (Titan)<br>Triapin (Vion) | Tezacitabine (Aventis)<br>Didox (Molecules for<br>Health) |
| TNF-alpha<br>agonists/<br>antagonists | Virulizin (Lorus Therapeutics)<br>CDC-394 (Celgene) | Revimid (Celgene) |
| Endothelin-A receptor<br>antagonists | Atrasentan (Abbot)<br>ZD-4054 (AstraZeneca) | YM-598 (Yamanouchi) |
| Retinoic acid receptor<br>agonists | Fenretinide (Johnson &<br>Johnson)<br>LGD-1550 (Ligand) | Alitretinoin (Ligand) |
| Immunomodulators | Interferon<br>Oncophage (Antigenics)<br>GMK (Progenics)<br>Adenocarcinoma vaccine<br>(Biomira)<br>CTP-37 (AVI BioPharma)<br>JRX-2 (Immuno-Rx)<br>PEP-005 (Peplin Biotech)<br>Synchrovax vaccines (CTL<br>Immuno)<br>Melanoma vaccine (CTL<br>Immuno)<br>p21-RAS vaccine (Gem-<br>Vax) | Dexosome therapy (Anosys)<br>Pentrix (Australian Cancer<br>Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and<br>antihormonal<br>agents | Oestrogens<br>Conjugated oestrogens<br>Ethynyloestradiol<br>chlorotrianisene<br>Idenestrol<br>Hydroxyprogesterone<br>caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic<br>agents | Talaporfin (Light Sciences)<br>Theralux (Theratechnologies)<br>Motexafin-Gadolinium<br>(Pharmacyclics) | Pd-Bacteriopheophorbid<br>(Yeda)<br>Lutetium-Texaphyrin<br>(Pharmacyclics)<br>Hypericin |
| Tyrosine kinase<br>inhibitors | Imatinib (Novartis)<br>Leflunomide(Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmith-<br>Kline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |

TABLE 1-continued

| | | |
|---|---|---|
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | Trans-retinic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidin (apoptosis promoter, Bioniche) |
| | CDA-II (apoptosis promoter, Everlife) | Ro-31-7453 (apoptosis promoter, La Roche) |
| | SDX-101 (apoptosis promoter, Salmedix) | Brostallicin (apoptosis promoter, Pharmacia) |
| | Ceflatonin (apoptosis promoter, ChemGenex) | |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |

TABLE 1-continued

| | | |
|---|---|---|
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La |
| | Idatrexate | Roche) |
| | | Ethynylcytidine (Taiho) |
| Topoisomerase | Amsacrine | Rubitecan (SuperGen) |
| inhibitors | Epirubicin | Exatecan mesylate |
| | Etoposide | (Daiichi) |
| | Teniposide or | Quinamed (ChemGenex) |
| | mitoxantrone | Gimatecan (Sigma-Tau) |
| | Irinotecan (CPT-11) | Diflomotecan (Beaufour- |
| | 7-Ethyl-10- | Ipsen) |
| | hydroxycamptothecin | TAS-103 (Taiho) |
| | Topotecan | Elsamitrucin (Spectrum) |
| | Dexrazoxanet | J-107088 (Merck & Co) |
| | (TopoTarget) | BNP-1350 (BioNumerik) |
| | Pixantrone (Novuspharma) | CKD-602 (Chong Kun |
| | Rebeccamycin analogue | Dang) |
| | (Exelixis) | KW-2170 (Kyowa Hakko) |
| | BBR-3576 (Novuspharma) | |
| Antitumour | Dactinomycin (Actinomycin | Amonafide |
| antibiotics | D) | Azonafide |
| | Doxorubicin (Adriamycin) | Anthrapyrazole |
| | Deoxyrubicin | Oxantrazole |
| | Valrubicin | Losoxantrone |
| | Daunorubicin | Bleomycin sulfate |
| | (Daunomycin) | (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem |
| | Cyanomorpholinodoxo- | Pharmaceuticals) |
| | rubicin | |
| | Mitoxantron (Novantron) | |
| Antimitotic agents | Paclitaxel | SB 408075 |
| | Docetaxel | (GlaxoSmithKline) |
| | Colchicine | E7010 (Abbott) |
| | Vinblastine | PG-TXL (Cell |
| | Vincristine | Therapeutics) |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner- | D 24851 (ASTA Medica) |
| | Lambert) | ER-86526 (Eisai) |
| | Cemadotin (BASF) | Combretastatin A4 (BMS) |
| | RPR 109881A (Aventis) | Isohomohalichondrin-B |
| | TXD 258 (Aventis) | (PharmaMar) |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient |
| | Auristatin PE (Teikoku | NeuroPharma) |
| | Hormone) | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |
| Aromatase | Aminoglutethimide | Exemestan |
| inhibitors | Letrozole | Atamestan (BioMedicines) |
| | Anastrazole | YM-511 (Yamanouchi) |
| | Formestan | |
| Thymidylate | Pemetrexed (Eli Lilly) | Nolatrexed (Eximias) |
| synthase | ZD-9331 (BTG) | CoFactor ™ (BioKeys) |
| inhibitors | | |

TABLE 1-continued

| | | |
|---|---|---|
| DNA antagonists | Trabectedin (PharmaMar)<br>Glufosfamide (Baxter<br>International)<br>Albumin + 32P (Isotope<br>Solutions)<br>Thymectacin (NewBiotics)<br>Edotreotid (Novartis) | Mafosfamide (Baxter<br>International)<br>Apaziquone (Spectrum<br>Pharmaceuticals)<br>O6-Benzylguanine<br>(Paligent) |
| Farnesyl<br>transferase<br>inhibitors | Arglabin (NuOncology<br>Labs)<br>Ionafarnib (Schering-<br>Plough)<br>BAY-43-9006 (Bayer) | Tipifarnib (Johnson &<br>Johnson)<br>Perillyl alcohol (DOR<br>BioPharma) |
| Pump inhibitors | CBT-1 (CBA Pharma)<br>Tariquidar (Xenova)<br>MS-209 (Schering AG) | Zosuquidar<br>trihydrochloride (Eli Lilly)<br>Biricodar dicitrate (Vertex) |
| Histone acetyl<br>transferase<br>inhibitors | Tacedinaline (Pfizer)<br>SAHA (Aton Pharma)<br>MS-275 (Schering AG) | Pivaloyloxymethyl butyrate<br>(Titan)<br>Depsipeptide (Fujisawa) |
| Metalloproteinase<br>inhibitors | Neovastat (Aeterna<br>Laboratories) | CMT-3 (CollaGenex)<br>BMS-275291 (Celltech) |
| Ribonucleoside<br>reductase<br>inhibitors | Marimastat (British<br>Biotech)<br>Gallium maltolate (Titan)<br>Triapin (Vion) | Tezacitabine (Aventis)<br>Didox (Molecules for<br>Health) |
| TNF-alpha<br>agonists/<br>antagonists | Virulizin (Lorus<br>Therapeutics)<br>CDC-394 (Celgene) | Revimid (Celgene) |
| Endothelin-A<br>receptor<br>antagonists | Atrasentan (Abbot)<br>ZD-4054 (AstraZeneca) | YM-598 (Yamanouchi) |
| Retinoic acid<br>receptor agonists | Fenretinide (Johnson &<br>Johnson)<br>LGD-1550 (Ligand) | Alitretinoin (Ligand) |
| Immuno-<br>modulators | Interferon<br>Oncophage (Antigenics)<br>GMK (Progenics)<br>Adenocarcinoma vaccine<br>(Biomira)<br>CTP-37 (AVI BioPharma)<br>JRX-2 (Immuno-Rx)<br>PEP-005 (Peplin Biotech)<br>Synchrovax vaccines (CTL<br>Immuno)<br>Melanoma vaccine (CTL<br>Immuno)<br>p21-RAS vaccine<br>(GemVax) | Dexosome therapy<br>(Anosys)<br>Pentrix (Australian Cancer<br>Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and<br>antihormonal<br>agents | Oestrogens<br>Conjugated oestrogens<br>Ethynyloestradiol<br>chlorotrianisene<br>Idenestrol<br>Hydroxyprogesterone<br>caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol<br>(EntreMed)<br>Arzoxifen (Eli Lilly) |
| Photodynamic<br>agents | Talaporfin (Light Sciences)<br>Theralux<br>(Theratechnologies)<br>Motexafin-Gadolinium<br>(Pharmacyclics) | Pd-Bacteriopheophorbid<br>(Yeda)<br>Lutetium-Texaphyrin<br>(Pharmacyclics)<br>Hypericin |
| Tyrosine kinase<br>inhibitors | Imatinib (Novartis)<br>Leflunomide(Sugen/Pharmacia)<br>ZD1839 (AstraZeneca)<br>Erlotinib (Oncogene<br>Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech) |

TABLE 1-continued

| | | |
|---|---|---|
| | Vatalanib (Novartis) | MDX-447 (Medarex) |
| | PKI166 (Novartis) | ABX-EGF (Abgenix) |
| | GW2016 (GlaxoSmithKline) | IMC-1C11 (ImClone) |
| | EKB-509 (Wyeth) | |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | Trans-retinic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidin (apoptosis promoter, Bioniche) |
| | CDA-II (apoptosis promoter, Everlife) | Ro-31-7453 (apoptosis promoter, La Roche) |
| | SDX-101 (apoptosis promoter, Salmedix) | Brostallicin (apoptosis promoter, Pharmacia) |
| | Ceflatonin (apoptosis promoter, ChemGenex) | |

A combined treatment of this type can be achieved with the aid of simultaneous, consecutive or separate dispensing of the individual components of the treatment. Combination products of this type employ the compounds according to the invention.

Assays

The compounds of the formula I described in the examples were tested by the assays described below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., J. Natl. Cancer Inst. 52:413-427; Nicosia et al., *In Vitro* 18:538-549).

Measurement of Met Kinase Activity

According to the manufacturer's data (Met, active, upstate, catalogue No. 14-526), Met kinase is expressed for the purposes of protein production in insect cells (Sf21; *S. frugiperda*) and subsequent affinity-chromatographic purification as "N-terminal 6His-tagged" recombinant human protein in a baculovirus expression vector.

The kinase activity can be measured using various available measurement systems. In the scintillation proximity method (Sorg et al., J. of Biomolecular Screening, 2002, 7, 11-19), the flashplate method or the filter binding test, the radioactive phosphorylation of a protein or peptide as substrate is measured using radioactively labelled ATP ($^{32}$P-ATP, $^{33}$P-ATP). In the case of the presence of an inhibitory compound, a reduced radioactive signal, or none at all, can be detected. Furthermore, homogeneous time-resolved fluorescence resonance energy transfer (HTR-FRET) and fluorescence polarisation (FP) technologies can be used as assay methods (Sills et al., J. of Biomolecular Screening, 2002, 191-214).

Other non-radioactive ELISA assay methods use specific phospho-anti-bodies (phospho-ABs). The phospho-antibody only binds the phosphorylated substrate. This binding can be detected by chemiluminescence using a second peroxidase-conjugated antibody (Ross et al., 2002, Biochem. J.).

Flashplate Method (Met Kinase)

The test plates used are 96-well Flashplate® microtitre plates from Perkin Elmer (Cat. No. SMP200). The components of the kinase reaction described below are pipetted into the assay plate. The Met kinase and the substrate poly Ala-Glu-Lys-Tyr, (PAGLT, 6:2:5:1), are incubated for 3 hrs at room temperature with radioactively labelled $^{33}$P-ATP in the presence and absence of test substances in a total volume of 100 µl. The reaction is terminated using 150 µl of a 60 mM EDTA solution. After incubation for a further 30 min at room temperature, the supernatants are filtered off with suction, and the wells are washed three times with 200 µl of 0.9% NaCl solution each time. The measurement of the bound radioactivity is carried out by means of a scintillation measuring instrument (Topcount NXT, Perkin-Elmer).

The full value used is the inhibitor-free kinase reaction. This should be approximately in the range 6000-9000 cpm. The pharmacological zero value used is staurosporin in a final concentration of 0.1 mM. The inhibitory values (IC50) are determined using the RS1_MTS program.

Kinase reaction conditions per well:
30 µl of assay buffer
10 µl of substance to be tested in assay buffer with 10% of DMSO
10 µl of ATP (final concentration 1 µM cold, 0.35 µCi of $^{33}$P-ATP)
50 µl of Met kinase/substrate mixture in assay buffer; (10 ng of enzyme/well, 50 ng of pAGLT/well)

Solutions Used:
Assay Buffer:
50 mM HEPES
3 mM magnesium chloride
3 µM sodium orthovanadate
3 mM manganese(II) chloride
1 mM dithiothreitol (DTT)
pH=7.5 (to be set using sodium hydroxide)
Stop Solution:
60 mM Titriplex III (EDTA)
$^{33}$P-ATP: Perkin-Elmer;
Met kinase: Upstate, Cat. No. 14-526, Stock 1 µg/10 µl; spec. activity 954 U/mg;
Poly-Ala-Glu-Lys-Tyr, 6:2:5:1: Sigma Cat. No. P1152

In-vivo tests (FIG. 1/1)

Experimental procedure: Female Balb/C mice (breeder: Charles River Wiga) were 5 weeks old on arrival. They were acclimatised to our keeping conditions for 7 days. Each mouse was subsequently injected subcutaneously in the pelvic area with 4 million TPR-Met/NIH3T3 cells in 100 µl of PBS (without Ca++ and Mg++). After 5 days, the animals were randomised into 3 groups, so that each group of 9 mice had an average tumour volume of 110 µl (range: 55-165). 100 µl of vehicle (0.25% methylcellulose/100 mM acetate buffer, pH 5.5) were administered daily to the control group, and 200 mg/kg of "A56" or "A91" dissolved in the vehicle (volume likewise 100 µl/animal) were administered daily to the treatment groups, in each case by gastric tube. After 9 days, the controls had an average volume of 1530 µl and the experiment was terminated.

Measurement of the tumour volume: The length (L) and breadth (B) were measured using a Vernier calliper, and the tumour volume was calculated from the formula L×B×B/2.

Keeping conditions: 4 or 5 animals per cage, feeding with commercial mouse food (Sniff).

The compounds "A56" and "A91" have a significant antitumoural action.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

Mass spectrometry (MS): EI (electron impact ionisation) M$^+$
FAB (fast atom bombardment) (M+H)$^+$
ESI (electrospray ionisation) (M+H)$^+$
APCI-MS (atmospheric pressure chemical ionisation—mass spectrometry) (M+H)$^+$.

Retention Time R$_t$ [Min]: Determination by HPLC
Column: Chromolith SpeedROD, 50×4.6 mm$^2$ (Order No. 1.51450.0001) from Merck
Gradient: 5.0 min, t=0 min, A:B=95:5, t=4.4 min: A:B=25:75, t=4.5 min to t=5.0 min: A:B=0:100
Flow rate: 3.00 ml/min
Eluent A: water+0.1% of TFA (trifluoroacetic acid)
Eluent B: acetonitrile+0.08% of TFA
Wavelength: 220 nm

EXAMPLE 1

The preparation of N-{3-[3-(4-hydroxyphenyl)-6-oxo-6H-pyridazin-1-ylmethyl]phenyl}acetamide ("A1") is carried out analogously to the following scheme

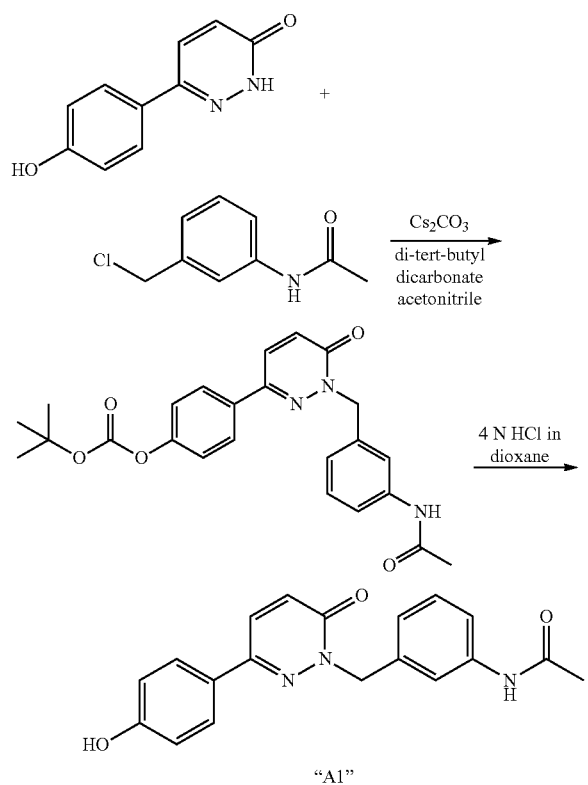

"A1"

1.1 240 mg (1.10 mmol) of di-tert-butyl dicarbonate and 358 mg (1.10 mmol) of caesium carbonate are added to a suspension of 188 mg (1.00 mmol) of 6-(4-hydroxyphenyl)-2H-pyridazin-3-one in 2 ml of acetonitrile, and the mixture is stirred at room temperature for three hours. 184 mg (1.00 mmol) of N-(3-chloromethylphenyl)acetamide are then added, and the suspension is stirred at 70° C. for 3 days. The reaction mixture is filtered, and the residue is washed with acetonitrile. The filtrate is chromatographed by means of preparative HPLC: N-{3-[3-(4-tert-butoxycarbonyloxyphenyl)-6-oxo-6H-pyridazin-1-ylmethyl]phenyl}acetamide as yellowish solid, ESI 436.

1.2 95 mg (0.22 mmol) of N-{3-[3-(4-tert-butoxycarbonyloxyphenyl)-6-oxo-6H-pyridazin-1-ylmethyl]phenyl}acetamide are dissolved in 3 ml of a 4N solution of hydrogen chloride in dioxane and left at room temperature for 18 hours. The resultant precipitate is filtered off with suction and washed with tert-butyl methyl ether and dried: N-{3-[3-(4-hydroxyphenyl)-6-oxo-6H-pyridazin-1-ylmethyl]phenyl}acetamide ("A1") as yellowish crystalline solid; ESI 336;

$^1$H-NMR (d$_6$-DMSO): δ=2.01 (s, 3H), 5.25 (s, 2H), 6.87 (d, J=9 Hz, 2H), 7.02 (m, 2H), 7.25 (t, J=7.5 Hz, 1H), 7.525 (bs, 1H), 7.56 (d, J=8 Hz, 1H), 7.72 (d, J=9 Hz, 2H), 7.99 (d, J=10 Hz, 1H), 10.0 (s, 1H).

An analogous procedure gives the compounds

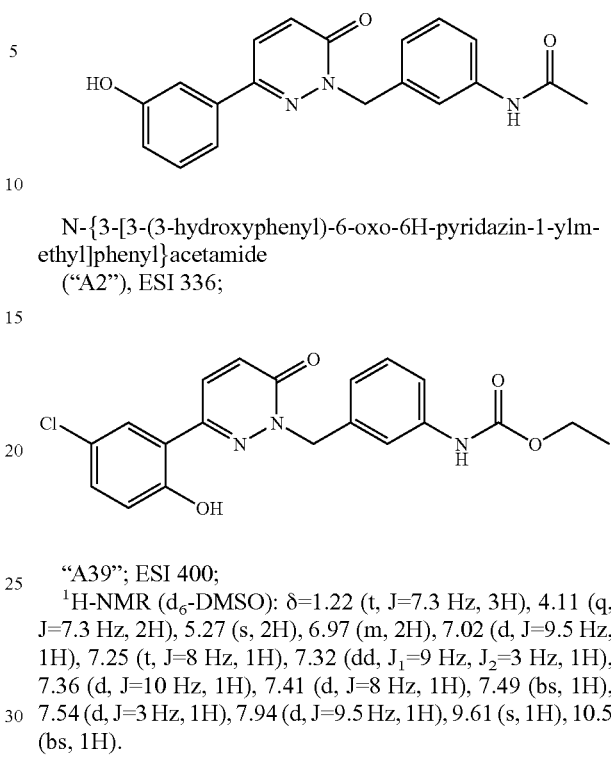

N-{3-[3-(3-hydroxyphenyl)-6-oxo-6H-pyridazin-1-ylmethyl]phenyl}acetamide ("A2"), ESI 336;

"A39"; ESI 400;
$^1$H-NMR (d$_6$-DMSO): δ=1.22 (t, J=7.3 Hz, 3H), 4.11 (q, J=7.3 Hz, 2H), 5.27 (s, 2H), 6.97 (m, 2H), 7.02 (d, J=9.5 Hz, 1H), 7.25 (t, J=8 Hz, 1H), 7.32 (dd, J$_1$=9 Hz, J$_2$=3 Hz, 1H), 7.36 (d, J=10 Hz, 1H), 7.41 (d, J=8 Hz, 1H), 7.49 (bs, 1H), 7.54 (d, J=3 Hz, 1H), 7.94 (d, J=9.5 Hz, 1H), 9.61 (s, 1H), 10.5 (bs, 1H).

EXAMPLE 2

The preparation of ethyl {3-[3-(4-chlorophenyl)-6-oxo-6H-pyridazin-1-ylmethyl]phenyl}carbaminate ("A3") is carried out analogously to the following scheme

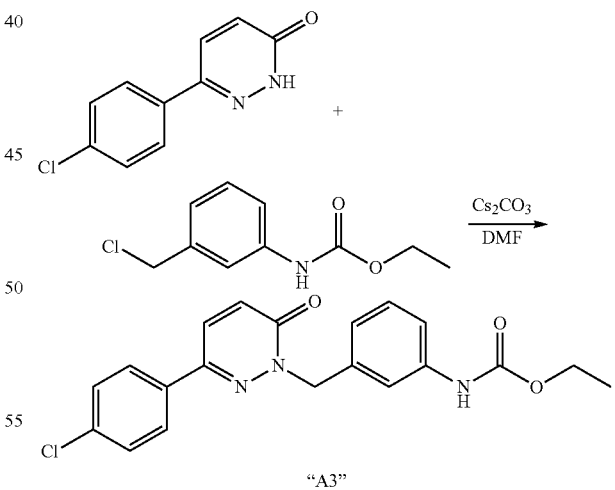

"A3"

179 mg (0.55 mmol) of caesium carbonate are added to a solution of 103 mg (0.50 mmol) of 6-(4-chlorophenyl)-2H-pyridazin-3-one and 107 mg (0.50 mmol) of ethyl (3-chloromethylphenyl)carbamate [prepared from 3-aminobenzyl alcohol by reaction with ethyl chloroformate/pyridine in dichloromethane and subsequent reaction of the resultant ethyl (3-hydroxymethylphenyl)carbamate with thionyl chloride in dichloromethane] in 1 ml of dimethylformamide, and the mixture is stirred at room temperature for 18 hours. Water is added to the reaction mixture, and the resultant pre-cipitate is filtered off with suction, washed with water and dried. The crude product is recrystallised from acetonitrile: ethyl {3-[3-(4-chlorophenyl)-6-oxo-6H-pyridazin-1-ylmethyl]phenyl}carbamate ("A3") as colourless crystals; ESI 384;

$^1$H-NMR (d$_6$-DMSO): δ=1.22 (t, J=7.3 Hz, 3H), 4.10 (q, J=7.3 Hz, 2H), 5.28 (s, 2H), 6.97 (d, J=7.8 Hz, 1H), 7.10 (d, J=10 Hz, 1H), 7.24 (t, J=8 Hz, 1H), 7.39 (d, J=9 Hz, 1H), 7.47 (bs, 1H), 7.55 (d, J=8.5 Hz, 2H), 7.93 (J=8.5 Hz, 2H), 8.08 (d, J=10 Hz, 1H), 9.58 (s, 1H).

The following compounds are obtained analogously

| No. | Structure | ESI |
|---|---|---|
| "A4" | | 380 |
| "A5" | | 368 |
| "A6" | | 428/430 |
| "A7" | | 338 |
| "A8" | | 342 |
| "A9" | | 350 |
| "A10" | | 384 |

-continued
| No. | Structure | ESI |
|---|---|---|
| "A11" | 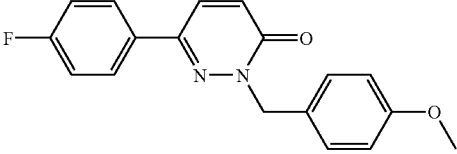 | 311 |
| "A12" | 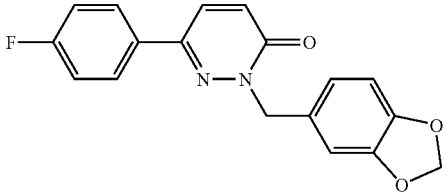 | 325 |
| "A13" | 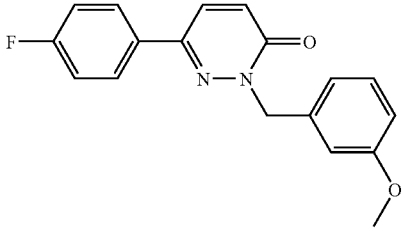 | 311 |
| "A14" | 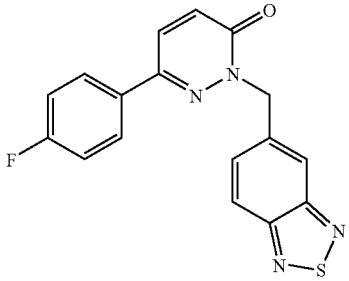 | 339 |
| "A19" | 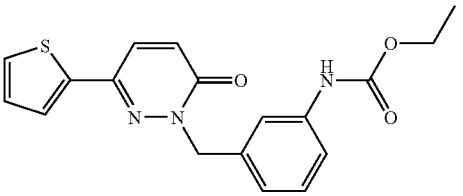 | 356 |
| "A23" | 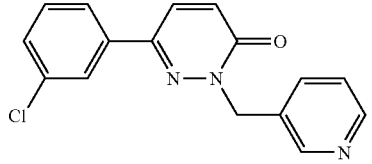 | 320 |
| "A24" | 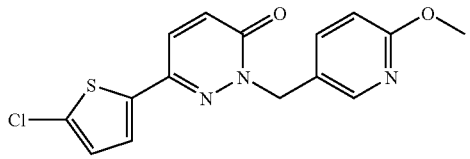 | |

| No. | Structure | ESI |
|---|---|---|
| "A25" | | |
| "A25a" | | |
| | obtainable from "A25" by treatment with BBr₃ | |
| "A38" | | 368 |
| "A42" | | |
EXAMPLE 3
The preparation of 3-dimethylaminopropyl {3-[3-(4-chlorophenyl)-6-oxo-6Hpyridazin-1-ylmethyl]phenyl}carbamate ("A15") is carried out analogously to the following scheme
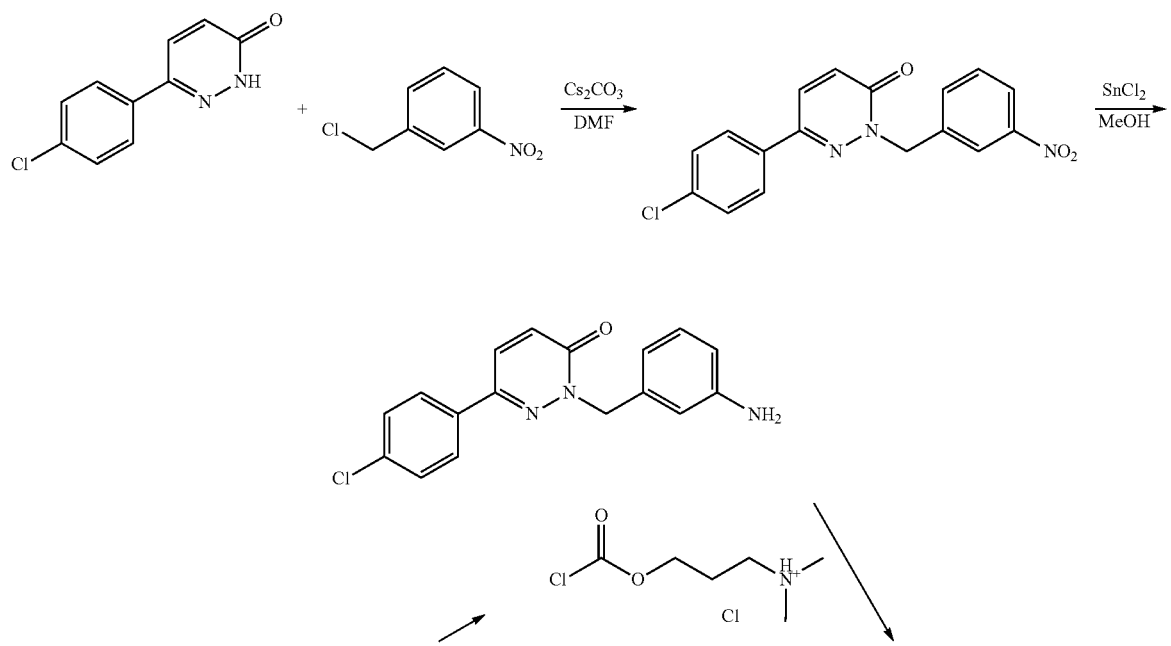

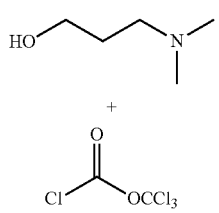 + 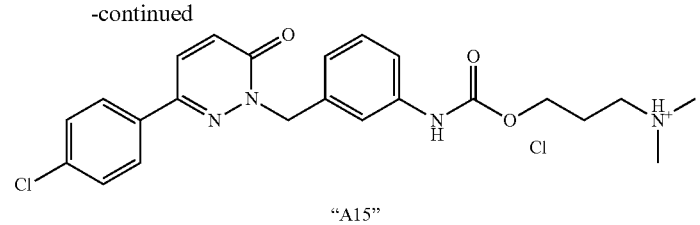

"A15"

3.1 1.56 g (4.79 mmol) of caesium carbonate are added to a solution of 900 mg (4.36 mmol) of 6-(4-chlorophenyl)-2H-pyridazin-3-one and 747 mg (4.36 mmol) of 3-nitrobenzyl chloride in 9 ml of DMF, and the resultant suspension is stirred at room temperature for 18 hours. Water is added to the reaction mixture, which is extracted three times with dichloromethane. The combined organic phases are dried over sodium sulfate and evaporated: 6-(4-chlorophenyl)-2-(3-nitrobenzyl)-2H-pyridazin-3-one as brownish solid; ESI 342.

3.2 3.00 g (15.7 mmol) of tin(II) chloride are added to a solution of 1.44 g (4.21 mmol) of 6-(4-chlorophenyl)-2-(3-nitrobenzyl)-2H-pyridazin-3-one in 25 ml of methanol. The solution is heated at the boil for three hours and left at room temperature for 18 hours. The reaction mixture is rendered alkaline using 18 ml of 2N sodium hydroxide solution and filtered through kieselguhr with suction. The residue is boiled up with a mixture of dichloromethane/methanol/water and filtered. The organic phases of the combined filtrates are evaporated under reduced pressure, and the resultant precipitate is filtered off with suction and dried under reduced pressure: 2-(3-aminobenzyl)-6-(4-chlorophenyl)-2H-pyridazin-3-one as palebrown solid; ESI 312.

3.3 23.0 ml (198 mmol) of 3-(dimethylamino)-1-propanol are dissolved in a 4N solution of hydrogen chloride in dioxane and evaporated under reduced pressure. 200 ml of acetonitrile are added to the residue, and 25.0 ml (198 mmol) of trichloromethyl chloroformate are added dropwise to the resultant suspension with external ice-cooling and stirring. The reaction mixture is stirred at room temperature for 18 hours and evaporated under reduced pressure. The residue is taken up in diethyl ether, the solution is filtered with suction, and the residue is dried under reduced pressure: (3-dimethylamino)propyl chloroformate hydrochloride as colourless solid.

3.4 0.24 ml (3.0 mmol) of pyridine and 303 mg (1.50 mmol) of (3-dimethylamino)propyl chloroformate hydrochloride are added to a solution of 312 mg (1.00 mmol) of 2-(3-aminobenzyl)-6-(4-chlorophenyl)-2H-pyridazin-3-one in 10 ml of dichloromethane, and the mixture is stirred at room temperature for one hour. The reaction solution is washed twice with saturated sodium hydrogencarbonate solution and twice with water. The organic phase is dried over sodium sulfate, evaporated and chromatographed on a silica-gel column with dichloromethane/methanol as eluent. The product-containing fractions are evaporated, and the residue is dissolved in 20 ml of a 0.1 N solution of hydrogen chloride in 2-propanol and evaporated under reduced pressure: 3-dimethylaminopropyl {3-[3-(4-chlorophenyl)-6-oxo-6H-pyridazin-1-ylmethyl]phenyl}carbamate hydrochloride ("A15") as yellowish solid; ESI 441;

$^1$H-NMR ($d_6$-DMSO): δ=2.02 (m, 2H), 2.75 (d, J=4.5 Hz, 6H), 3.12 (m, 2H), 4.13 (t, J=6 Hz, 2H), 5.26 (s, 2H), 7.00 (d, J=8 Hz, 1H), 7.11 (d, J=9.5 Hz, 1H), 7.26 (t, J=8 Hz, 1H), 7.41 (d, J=8 Hz, 1H), 7.46 (s, 1H), 7.57 (d, J=8 Hz, 2H), 7.93 (d, J=8 Hz, 2H), 8.10 (d, J=9.5 Hz, 1H), 9.73 (bs, 1H), 10.22 (bs, 1H).

The following compounds are obtained analogously

| No. | Structure | ESI |
|---|---|---|
| "A16" | 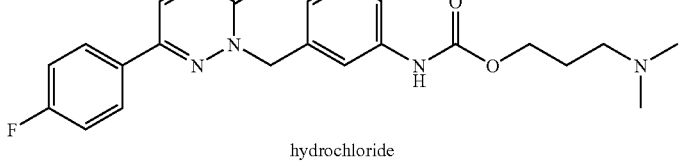<br>hydrochloride | 425 |
| | $^1$H-NMR ($d_6$-DMSO): δ = 2.02 (m, 2 H), 2.76 (d, J = 4.8 Hz, 6 H), 3.10 (m, 2 H), 4.13 (m, 2 H), 5.28 (s, 2 H), 7.00 (d, J = 7.5 Hz, 1 H), 7.10 (d, J = 10 Hz, 1 H), 7.34 (m, 5 H), 7.95 (dd, $J_1$ = 9 Hz, $J_2$ = 6.6 Hz, 2 H), 8.08 (d, J = 10 Hz, 1 H), 9.70 (s, 1 H), 10.15 (bs, 1 H) | |
| "A17" | 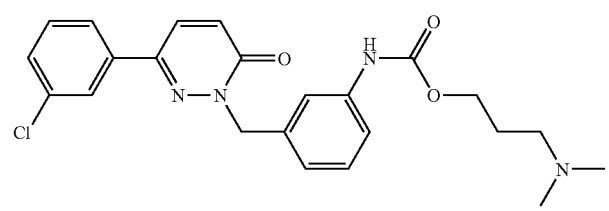<br>hydrochloride | 441 |

-continued
| No. | Structure | ESI |
|---|---|---|
| "A26" | 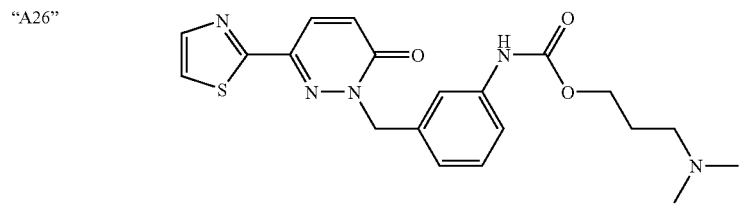 | |
| "A27" | 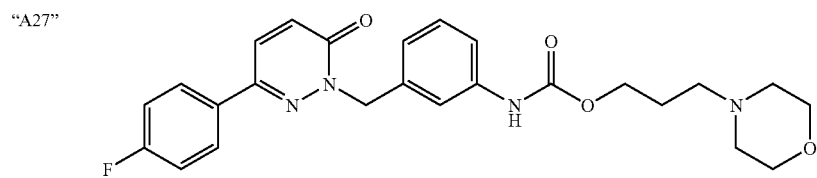 | |
| "A28" | 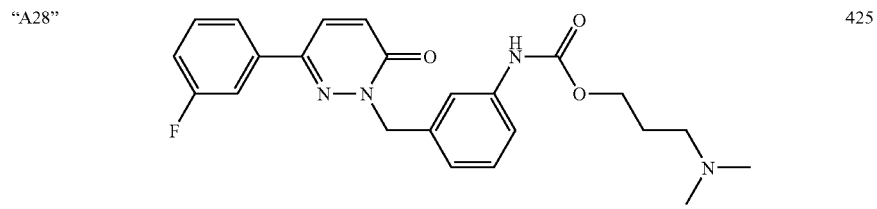 | 425 |
| "A29" | 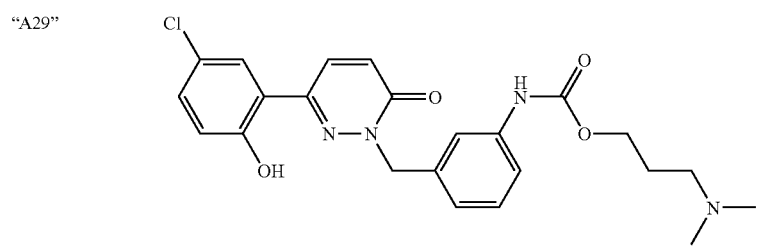 | |
| "A30" | 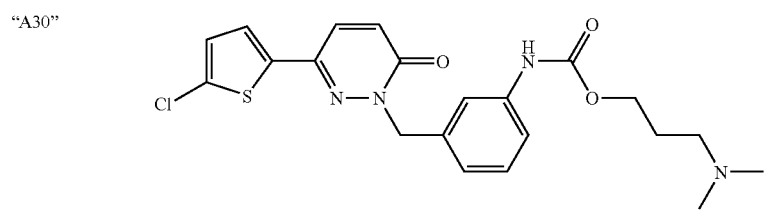 | |
| "A34" | 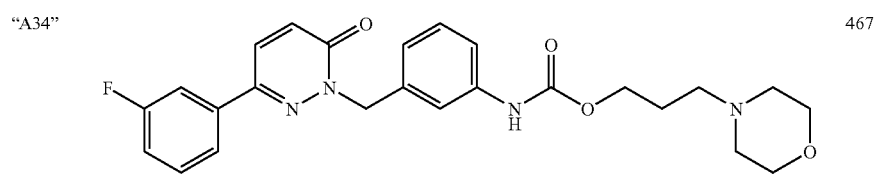 | 467 |
| "A36" | 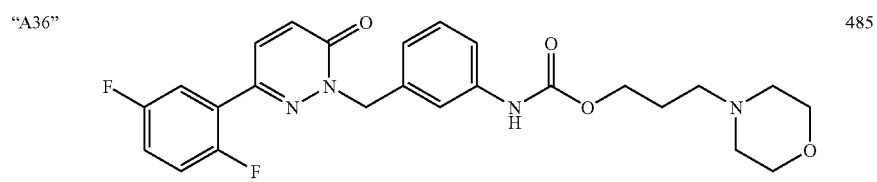 | 485 |

| No. | Structure | ESI |
|---|---|---|
| "A37" | 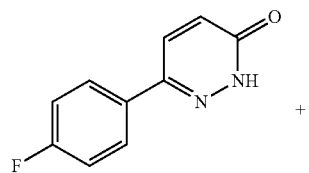 | 443 |
| "A40" | 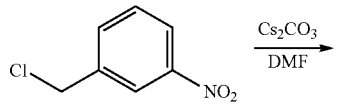  hydrochloride  $^1$H-NMR (d$_6$-DMSO): δ = 2.07 (m, 2 H), 3.06 (m, 2 H), 3.17 (m, 2 H), 3.42 (d, J = 13 Hz, 2 H), 3.75 (m, 2 H), 3.95 (d, J = 13 Hz, 2 H), 4.14 (t, J = 6 Hz, 2 H), 5.30 (s, 2 H), 7.01 (d, J = 7.5 Hz, 1 H), 7.11 (d, J = 9.5 Hz, 1 H), 7.26 (t, J = 8 Hz, 1 H), 7.40 (d, J = 7.5 Hz, 1 H), 7.47 (bs, 1 H), 7.53 (m, 2 H), 7.88 (m, 1 H), 7.96 (bs, 1 H), 8.14 (d, J = 9.5 Hz, 1 H), 9.71 (s, 1 H), 10.62 (bs, 1 H). | 483 |
| "A41" | 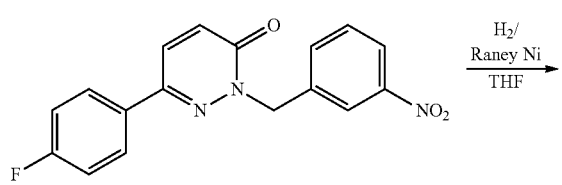 | |

EXAMPLE 4

The preparation of 1-ethyl-3-{3-[3-(4-fluorophenyl)-6-oxo-6H-pyridazin-1-ylmethyl]phenyl}urea ("A18") is carried out analogously to the following scheme

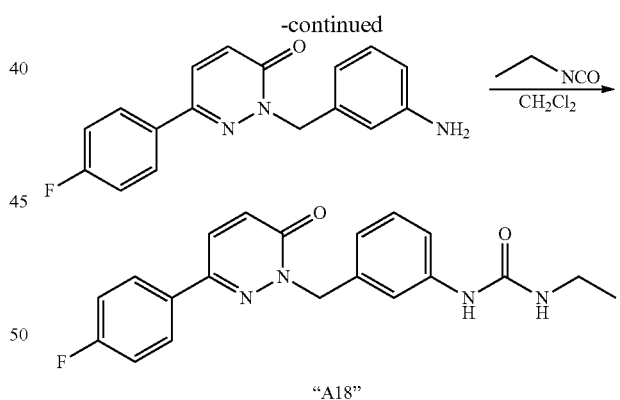

4.1 6-(4-Fluorophenyl)-2-(3-nitrobenzyl)-2H-pyridazin-3-one is obtained analogously to Example 3 as slightly brownish solid; ESI 326.

4.2 1.2 g of Raney nickel are added to a solution of 2.48 g (7.62 mmol) of 6-(4-fluorophenyl)-2-(3-nitrobenzyl)-2H-pyridazin-3-one in 25 ml of THF, and the mixture is hydrogenated at room temperature and atmospheric pressure. The catalyst is filtered off, and the filtrate is evaporated. The solid residue is stirred with petroleum ether, filtered off with suction, washed with petroleum ether and dried under reduced pressure: 2-(3-aminobenzyl)-6-(4-fluorophenyl)-2H-pyridazin-3-one as colourless solid; ESI 296.

4.3 42.6 mg (0.60 mmol) of ethyl isocyanate are added to a solution of 148 mg (0.50 mmol) of 2-(3-aminobenzyl)-6-(4-fluorophenyl)-2H-pyridazin-3-one in 1 ml of dichloromethane, and the reaction mixture is stirred at room temperature for 42 hours. The resultant precipitate is filtered off with suction, washed with tert-butyl methyl ether and dried under reduced pressure: 1-ethyl-3-{3-[3-(4-fluorophenyl)-6-oxo-6H-pyridazin-1-ylmethyl]-phenyl}urea ("A18") as colourless matted needles; ESI 367;

$^1$H-NMR ($d_6$-DMSO): δ=1.03 (t, J=7.3 Hz, 3H), 3.08 (m, 2H), 5.25 (s, 2H), 6.02 (t, J=5.3 Hz, 1H), 6.88 (d, J=7.5 Hz, 1H), 7.09 (d, J=10 Hz, 1H), 7.18 (t, J=8 Hz, 1H), 7.33 (m, 3H), 7.95 (dd, $J_1$=9 Hz, $J_2$=6.6 Hz, 2H), 8.44 (s, 1H).

The following compounds are obtained analogously

| No. | Structure | ESI |
|---|---|---|
| "A20" | 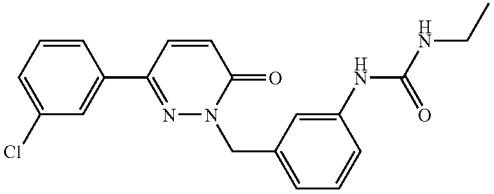 | 383 |
| "A31" | 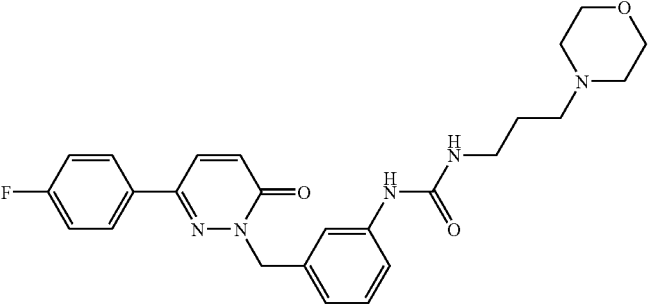 | |
| "A32" | 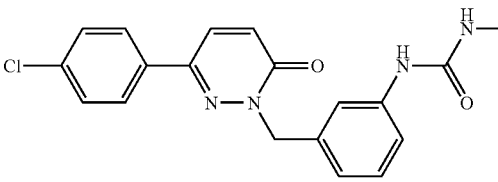 | 383 |
| "A33" | 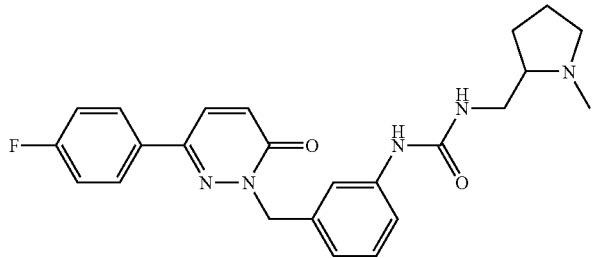 | |
| A35" | 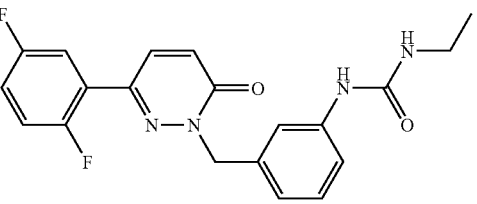 | 385 |

EXAMPLE 5

An alternative preparation of "A40" is carried out analogously to the following scheme

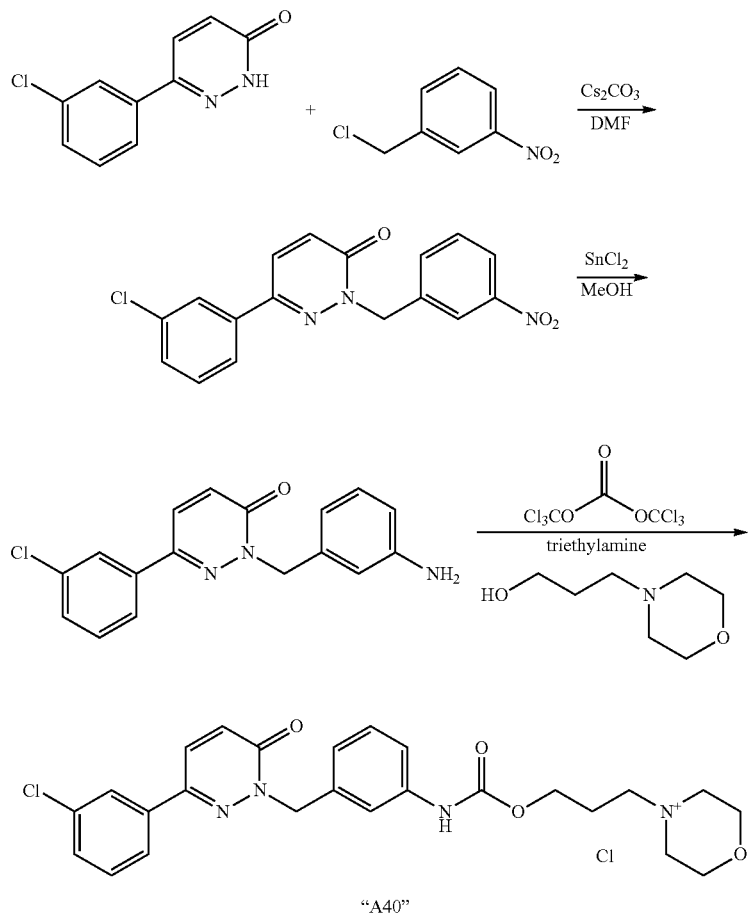

"A40"

Apart from the final reaction step, the reactions are carried out analogously to Example 3.

Final Step:

95.4 mg (0.20 mmol) of bis(trichloromethyl) carbonate are added to a suspension of 156 mg (0.50 mmol) of 2-(3-aminobenzyl)-6-(3-chlorophenyl)-2H-pyridazin-3-one in 2 ml of dichloromethane. 102 mg (1.00 mmol) of triethylamine are then added dropwise with ice-cooling, and the reaction mixture is stirred at room temperature for 10 minutes. 87.1 mg (0.6 mmol) of 3-morpholin-4-ylpropan-1-ol are then added, and the mixture is stirred at room temperature for 5 hours. Water is added to the reaction mixture. The organic phase is separated off, and the aqueous phase is extracted a number of times with dichloromethane. The combined organic phases are dried over sodium sulfate, evaporated and dried under reduced pressure. The residue is dissolved in 5 ml of a 0.1 N solution of hydrogen chloride in 2-propanol, and the solution is added dropwise to 50 ml of tert-butyl methyl ether. The resultant pre-cipitate is filtered off, washed with tert-butyl methyl ether and dried: 3-morpholin-4-ylpropyl {3-[3-(3-chlorophenyl)-6-oxo-6H-pyridazin-1-ylmethyl]phenyl}carbamate hydrochloride ("A40") as ochre-yellow solid.

EXAMPLE 6

The preparation of 1-ethyl-3-(3-{3-[3-(2-morpholin-4-ylethoxy)phenyl]-6-oxo-6H-pyridazin-1-ylmethyl}phenyl)urea ("A43"), ESI 478, and of 1-ethyl-3-{3-[3-(3-hydroxyphenyl)-6-oxo-6H-pyridazin-1-ylmethyl]-phenyl}urea ("A43a"), ESI 365, is carried out analogously to the following scheme

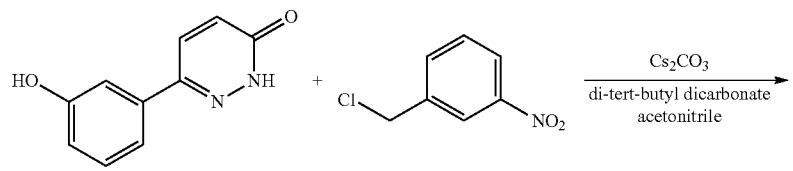

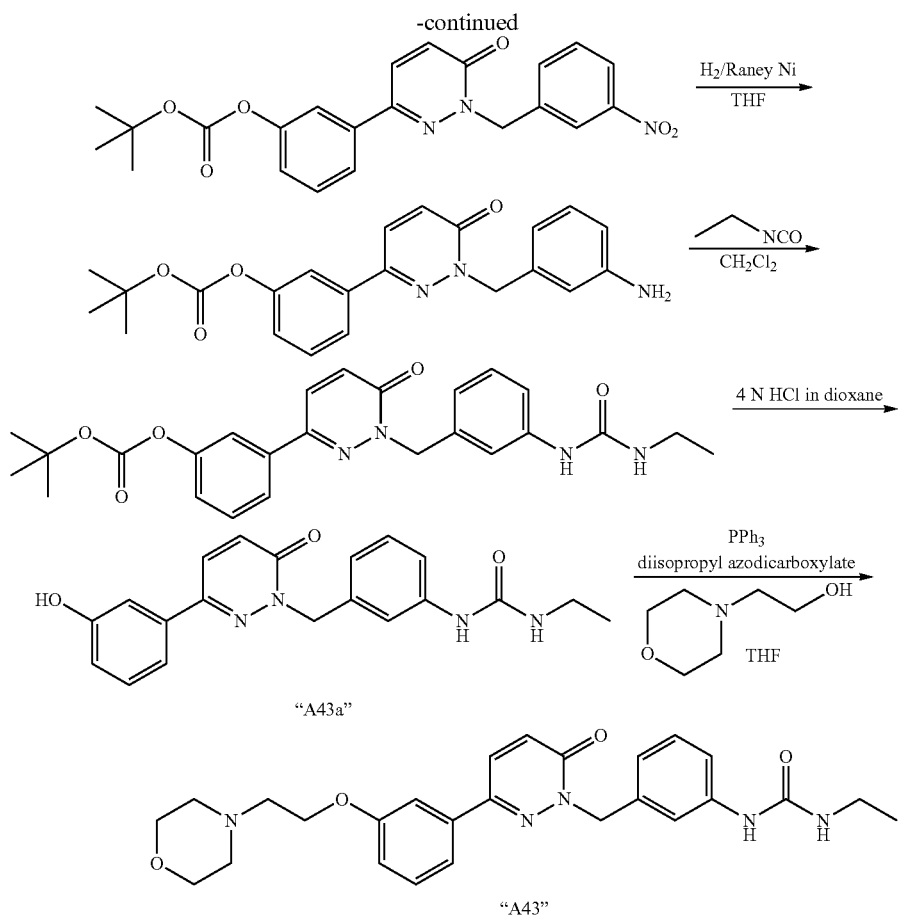
"A43a"
"A43"
The preparation of "A44" is carried out analogously
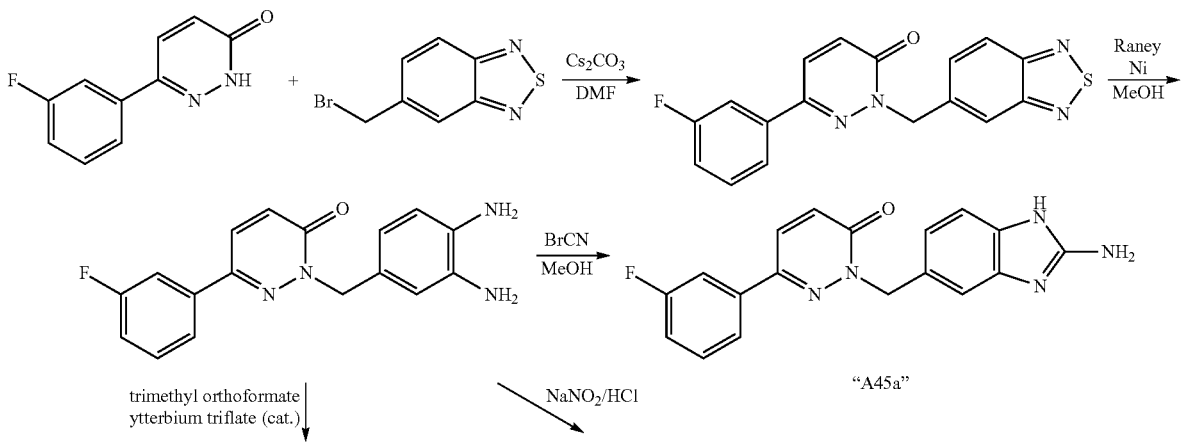
EXAMPLE 7
The preparation of
2-(1H-benzimidazol-5-ylmethyl)-6-(3-fluorophenyl)-2H-pyridazin-3-one ("A45"), ESI 321,
2-(2-amino-1H-benzimidazol-5-ylmethyl)-6-(3-fluorophenyl)-2H-pyridazin-3-one ("A45a") hydrobromide, ESI 336,
and 2-(1H-benzotriazol-5-ylmethyl)-6-(3-fluorophenyl)-2H-pyridazin-3-one ("A46")
is carried out analogously to the following scheme

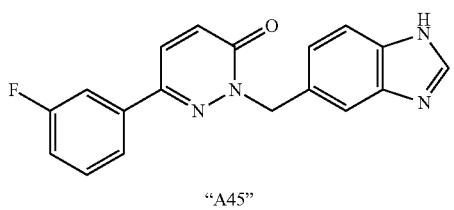

"A45"

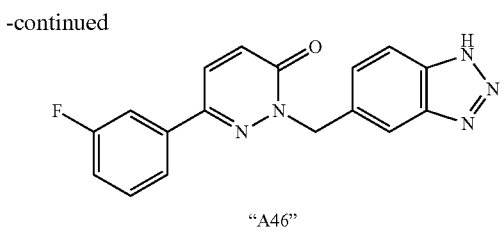

"A46"

The preparation of "A21"

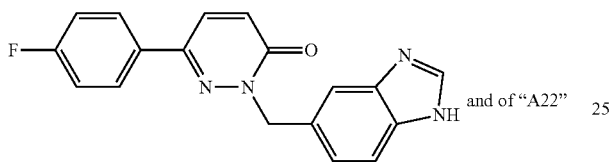

"A21"

and of "A22"

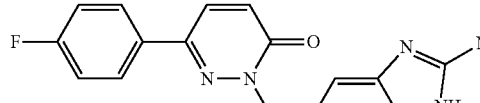

"A22"

is also carried out analogously.

EXAMPLE 8

The following compounds are obtained analogously to Example 2

| No. | Name/Structure | ESI |
|---|---|---|
| "A47" | 2-Benzo-1,2,5-thiadiazol-5-ylmethyl-6-(3-fluorophenyl)-2H-pyridazin-3-one | 339 |

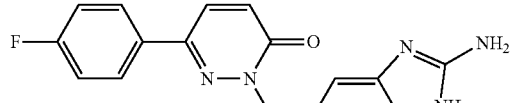

-continued

| No. | Name/Structure | ESI |
|---|---|---|
| "A48" | 6-(3,5-Difluorophenyl)-2-pyridin-3-ylmethyl-2H-pyridazin-3-one | 300 |
| "A49" | 6-(3,5-Difluorophenyl)-2-(3-cyanobenzyl)-2H-pyridazin-3-one | 324 |
| "A50" | 6-(3,5-Difluorophenyl)-2-(3-methoxycarbonylbenzyl)-2H-pyridazin-3-one | 357 |
| "A51" | 6-(3,5-Difluorophenyl)-2-quinolin-6-ylmethyl-2H-pyridazin-3-one | 350 |
| "A52" | 6-(3,4-Difluorophenyl)-2-quinolin-6-ylmethyl-2H-pyridazin-3-one | 350 |
| "A53" | 6-(4-fluorophenyl)-2-quinolin-6-ylmethyl-2H-pyridazin-3-one | 332 |
| "A54" | 6-(3,5-Difluorophenyl)-2-pyridin-4-ylmethyl-2H-pyridazin-3-one | 300 |
| "A55" | 6-(3,5-Difluorophenyl)-2-(3-acetamidobenzyl)-2H-pyridazin-3-one | 356 |

EXAMPLE 9

The following compounds are obtained analogously to Example 3

| No. | Name/Structure | ESI |
|---|---|---|
| "A56" | 3-Dimethylaminopropyl {3-[3-(3,5-difluorophenyl)-6-oxo-6H-pyridazin-1-ylmethyl]phenyl}-carbamate, hydrochloride | 443 |

$^1$H-NMR (d$_6$-DMSO): δ [ppm] 2.04 (m, 2 H), 2.75 (s, 6 H), 3.12 (m, 2 H), 4.14 (t, J = 6 Hz, 2 H), 5.29 (s, 2 H), 7.01 (m, 1 H), 7.13 (d, J = 9.5 Hz, 1 H), 7.26 (t, J = 8 Hz, 1 H), 7.37 (m, 2 H), 7.50 (m, 1 H), 7.66 (m, 2 H), 8.15 (d, J = 9.5 Hz, 1 H), 9.73 (s, 1 H), 10.42 (bs, 1 H)

| No. | Name/Structure | ESI |
|---|---|---|
| "A57" | 3-Dimethylaminopropyl [3-(6-oxo-3-thiazol-2-yl-6H-pyridazin-1-ylmethyl)phenyl]carbamate, hydrochloride | 414 |
| "A58" | 3-Dimethylaminopropyl (3-{1-[3-(3,5-difluorophenyl)-6-oxo-6H-pyridazin-1-yl]ethyl}phenyl)-carbamate, hydrochloride | 457 |
| "A59" | 3-Dimethylaminopropyl {3-[3-(3,4-difluorophenyl)-6-oxo-6H-pyridazin-1-ylmethyl]phenyl}-carbamate, hydrochloride | 443 |
| "A60" | 3-Dimethylaminopropyl {3-[3-(3,4,5-trifluorophenyl)-6-oxo-6H-pyridazin-1-ylmethyl]phenyl}-carbamate, hydrochloride | 461 |
| "A61" | 3-Dimethylaminopropyl {3-[3-(3-cyanophenyl)-6-oxo-6H-pyridazin-1-ylmethyl]phenyl}carbamate, hydrochloride | 432 |
| "A62" | 3-Dimethylaminopropyl {3-[3-(2,3-difluorophenyl)-6-oxo-6H-pyridazin-1-ylmethyl]phenyl}-carbamate, hydrochloride | 443 |
| "A63" | 3-Dimethylaminopropyl {3-[3-(2,4-difluorophenyl)-6-oxo-6H-pyridazin-1-ylmethyl]phenyl}-carbamate, hydrochloride | 443 |

-continued

| No. | Name/Structure | ESI |
|---|---|---|
| "A64" | 3-Dimethylaminopropyl {3-[3-(3,5-dichloro-phenyl)-6-oxo-6H-pyridazin-1-ylmethyl]phenyl}-carbamate, hydrochloride | 475 |
| "A65" | 3-Dimethylaminopropyl [3-(6-oxo-3-pyridin-3-yl-6H-pyridazin-1-ylmethyl)phenyl]carbamate, formate | 408 |

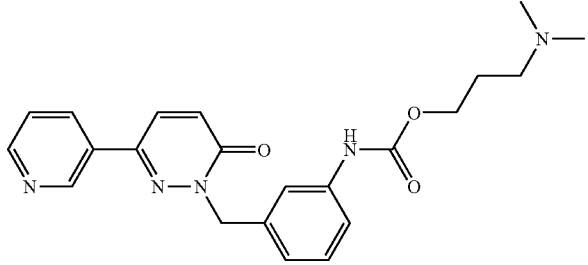

| No. | Name/Structure | ESI |
|---|---|---|
| "A66" | 3-Dimethylaminopropyl {3-[3-(4-cyanophenyl)-6-oxo-6H-pyridazin-1-ylmethyl]phenyl}carbamate, hydrochloride | 432 |

EXAMPLE 10

The following compounds are obtained analogously to Example 5

| No. | Name/Structure | ESI |
|---|---|---|
| "A67" | 3-Morpholin-4-ylpropyl {3-[3-(3,5-difluorophenyl)-6-oxo-6H-pyridazin-1-ylmethyl]phenyl}carbamate, hydrochloride | 485 |

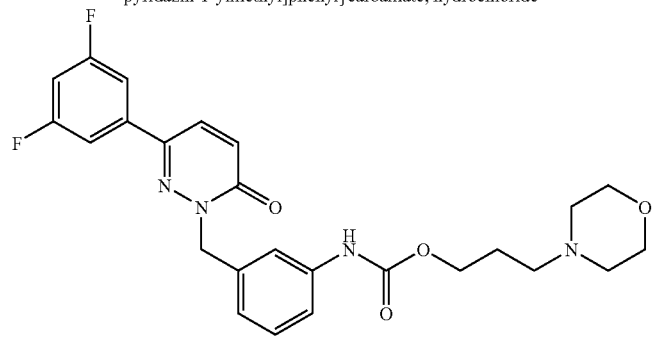

$^1$H-NMR (d$_6$-DMSO): δ [ppm] 2.08 (m, 2 H), 3.05 (m, 2 H), 3.16 (m, 2 H), 3.42 (m, 2 H), 3.75 (m, 2 H), 3.95 (m, 2 H), 4.14 (t, J = 6.3 Hz, 2 H), 5.29 (s, 2 H), 7.02 (m, 1 H), 7.13 (d, J = 9.5 Hz, 1 H), 7.26 (t, J = 8 Hz, 1 H), 7.39 (m, 2 H), 7.49 (m, 1 H), 7.67 (m, 2 H), 8.16 (d, J = 9.5 Hz, 1 H), 9.72 (s, 1 H), 10.7 (bs, 1 H)

| No. | Name/Structure | ESI |
|---|---|---|
| "A68" | 3-Morpholin-4-ylpropyl {3-[3-(3,4-difluorophenyl)-6-oxo-6H-pyridazin-1-ylmethyl]phenyl}carbamate, hydrochloride | 485 |
| "A69" | 3-Morpholin-4-ylpropyl{3-[3-(4-fluorophenyl)-6-oxo-6H-pyridazin-1-ylmethyl]phenyl}carbamate, hydrochloride | 467 |
| "A70" | 3-Morpholin-4-ylpropyl[3-(6-oxo-3-thiazol-2-yl-6H-pyridazin-1-ylmethyl)phenyl]carbamate, hydrochloride | 456 |

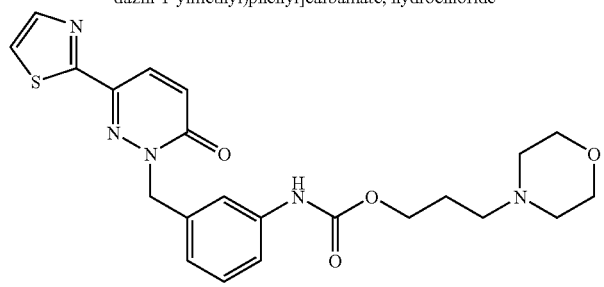

| No. | Name/Structure | ESI |
|---|---|---|
| "A71" | 3-Morpholin-4-ylpropyl [3-(6-oxo-3-thiophen-2-yl-6H-pyridazin-1-ylmethyl)phenyl]carbamate, hydrochloride | 455 |
| "A72" | 3-Morpholin-4-ylpropyl (3-{1-[3-(3,5-difluorophenyl)-6-oxo-6H-pyridazin-1-yl]ethyl}phenyl)carbamate, hydrochloride | 499 |
| "A73" | 3-Pyrrolidin-1-ylpropyl {3-[3-(3,4-difluorophenyl)-6-oxo-6H-pyridazin-1-ylmethyl]phenyl}carbamate, hydrochloride | 469 |
| "A73a" | 2-Pyrrolidin-1-ylethyl {3-[3-(3,4-difluorophenyl)-6-oxo-6H-pyridazin-1-ylmethyl]phenyl}carbamate, hydrochloride | 455 |
| "A74" | 3-Pyrrolidin-1-ylpropyl {3-[3-(3,5-difluorophenyl)-6-oxo-6H-pyridazin-1-ylmethyl]phenyl}carbamate, hydrochloride | 469 |
| "A75" | 3-Methoxypropyl {3-[3-(3,5-difluorophenyl)-6-oxo-6H-pyridazin-1-ylmethyl]phenyl}carbamate | 430 |
| "A76" | 3-Methoxypropyl {3-[3-(3,4-difluorophenyl)-6-oxo-6H-pyridazin-1-ylmethyl]phenyl}carbamate | 430 |
| "A77" | 2-Morpholin-4-ylethyl {3-[3-(3,5-difluorophenyl)-6-oxo-6H-pyridazin-1-ylmethyl]phenyl}carbamate, hydrochloride | 471 |

-continued

| No. | Name/Structure | ESI |
|---|---|---|
| "A78" | 3-Morpholin-4-ylpropyl {3-[6-oxo-3-(3,4,5-trifluorophenyl)-6H-pyridazin-1-ylmethyl]phenyl}carbamate, hydrochloride 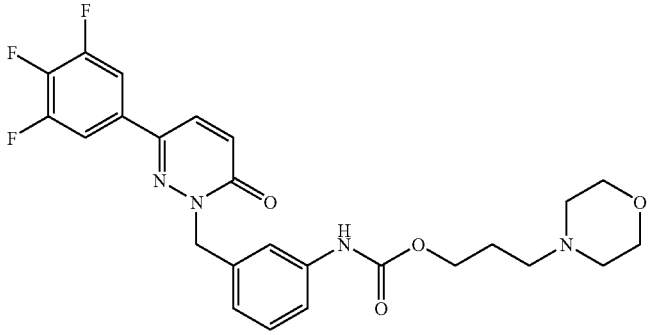 | 503 |
| "A79" | 3-Pyrrolidin-1-ylpropyl {3-[6-oxo-3-(3,4,5-trifluorophenyl)-6H-pyridazin-1-ylmethyl]phenyl}carbamate, hydrochloride 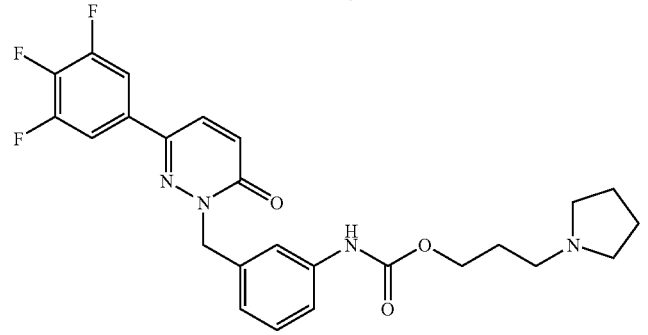 | 487 |
| "A80" | 2-Dimethylaminoethyl {3-[3-(3,5-difluorophenyl)-6-oxo-6H-pyridazin-1-ylmethyl]phenyl}carbamate, hydrochloride 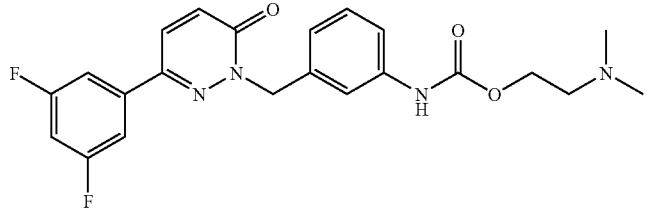 | 429 |
| "A81" | 2-Morpholin-4-ylethyl {3-[3-(3,4-difluorophenyl)-6-oxo-6H-pyridazin-1-ylmethyl]phenyl}carbamate, formate 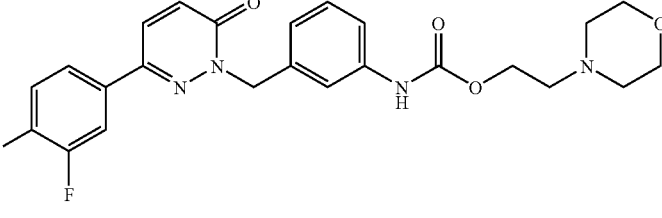 | 471 |
| "A82" | 2-Dimethylaminoethyl {3-[3-(3,4-difluorophenyl)-6-oxo-6H-pyridazin-1-ylmethyl]phenyl}carbamate, hydrochloride 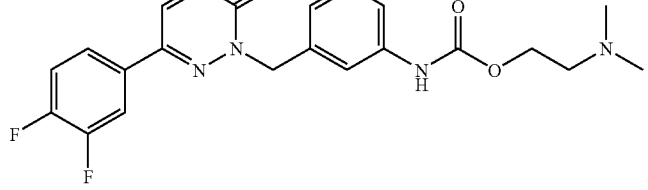 | 429 |

| No. | Name/Structure | ESI |
|---|---|---|
| "A83" | 2-Pyrrolidin-1-ylethyl {3-[3-(3,5-difluorophenyl)-6-oxo-6H-pyridazin-1-ylmethyl]phenyl}carbamate, hydrochloride | 455 |
| "A84" | 2-Methoxyethyl {3-[3-(3,5-difluorophenyl)-6-oxo-6H-pyridazin-1-ylmethyl]phenyl}carbamate | 416 |
| "A85" | 2-Methoxyethyl {3-[3-(3,4-difluorophenyl)-6-oxo-6H-pyridazin-1-ylmethyl]phenyl}carbamate | 416 |
| "A86" | 3-Morpholin-4-ylpropyl{3-[3-(2,4-difluorophenyl)-6-oxo-6H-pyridazin-1-ylmethyl]phenyl}carbamate, hydrochloride | 485 |
| "A87" | 3-Morpholin-4-ylpropyl {3-[3-(2,3-difluorophenyl)-6-oxo-6H-pyridazin-1-ylmethyl]phenyl}carbamate, hydrochloride | 485 |
| "A88" | 3-Morpholin-4-ylpropyl{3-[3-(3-cyanophenyl)-6-oxo-6H-pyridazin-1-ylmethyl]phenyl}carbamate, hydrochloride | 474 |
| "A89" | 2-Morpholin-4-ylethyl {3-[3-(3,4-difluorophenyl)-6-oxo-6H-pyridazin-1-ylmethyl]phenyl}carbamate, hydrochloride | 471 |

| No. | Name/Structure | ESI |
|---|---|---|
| "A90" | 3-(4-Methylpiperazin-1-yl)propyl {3-[3-(3,4-difluorophenyl)-6-oxo-6H-pyridazin-1-ylmethyl]phenyl}carbamate, dihydrochloride 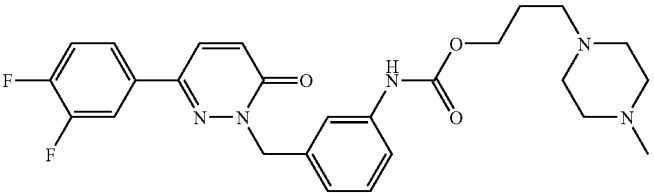 | 498 |
| "A91" | 3-(4-Methylpiperazin-1-yl)propyl {3-[3-(3,5-difluorophenyl)-6-oxo-6H-pyridazin-1-ylmethyl]phenyl}carbamate, dihydrochloride, hydrochloride | 498 |

$^1$H-NMR (d$_6$-DMSO): δ [ppm] 2.11 (m, 2 H), 2.83 (s, 3 H), 3.14-3.81 (m, 10 H), 4.15 (t, J = 6 Hz, 2 H), 5.30 (s, 2 H), 7.02 (m, 1 H), 7.13 (d, J = 9.5 Hz, 1 H), 7.35 (t, J = 8 Hz, 1 H), 7.36 (m, 1 H), 7.42 (m, 1 H), 7.50 (m, 1 H), 7.66 (m, 2 H), 8.15 (d, J = 9.5 Hz, 1 H), 9.75 (s, 1 H), 12.0 (bs, 2 H)

| No. | Name/Structure | ESI |
|---|---|---|
| "A92" | 2-(4-Methylpiperazin-1-yl)ethyl {3-[3-(3,4-difluorophenyl)-6-oxo-6H-pyridazin-1-ylmethyl]phenyl}carbamate, dihydrochloride 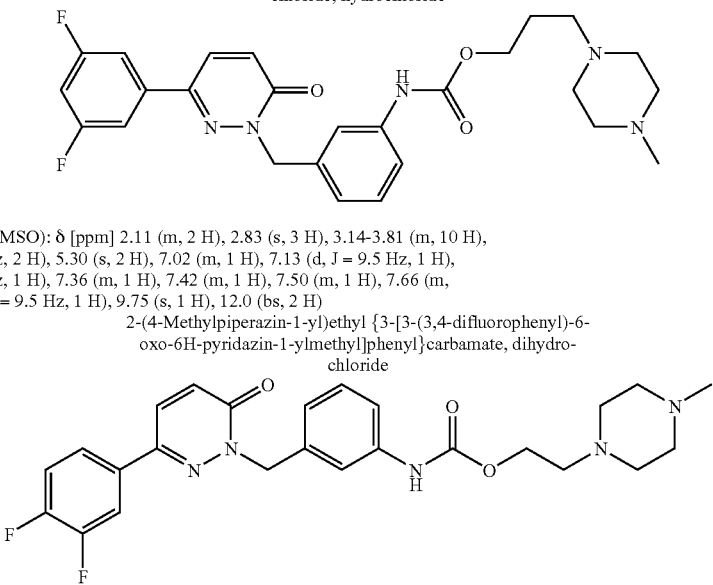 | 484 |
| "A93" | 2-(4-Methylpiperazin-1-yl)ethyl {3-[3-(3,5-difluorophenyl)-6-oxo-6H-pyridazin-1-ylmethyl]phenyl}carbamate, dihydrochloride | 484 |
| "A94" | 2-(2-Methoxyethoxy)ethyl {3-[3-(3,5-difluorophenyl)-6-oxo-6H-pyridazin-1-ylmethyl]phenyl}carbamate | 460 |
| "A95" | 2-Morpholin-4-ylethyl {3-[6-oxo-3-(3,4,5-trifluorophenyl)-6H-pyridazin-1-ylmethyl]phenyl}carbamate, hydrochloride 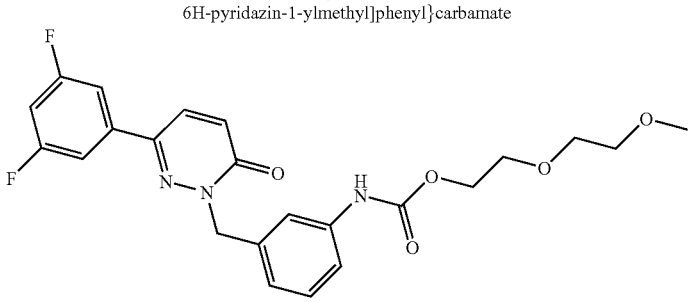 | 489 |

-continued

| No. | Name/Structure | ESI |
|---|---|---|
| "A96" | 3-Morpholin-4-ylpropyl {3-[3-(3,5-dichlorophenyl)-6-oxo-6H-pyridazin-1-ylmethyl]phenyl}carbamate, hydrochloride | 517 |
| "A97" | 2-(2-Methoxyethoxy)ethyl {3-[3-(3,4-difluorophenyl)-6-oxo-6H-pyridazin-1-ylmethyl]phenyl}carbamate | 460 |
| "A98" | 1-Methylpiperidin-4-yl {3-[3-(3,5-difluorophenyl)-6-oxo-6H-pyridazin-1-ylmethyl]phenyl}carbamate, hydrochloride | 455 |
| "A99" | 1-Methylpiperidin-4-yl {3-[3-(3,4-difluorophenyl)-6-oxo-6H-pyridazin-1-ylmethyl]phenyl}carbamate, hydrochloride | 455 |
| "A100" | 2-Morpholin-4-ylethyl {3-[3-(4-cyanophenyl)-6-oxo-6H-pyridazin-1-ylmethyl]phenyl}carbamate, hydrochloride | 460 |
| "A101" | 3-(4-Methylpiperazin-1-yl)propyl {3-[6-oxo-3-(3,4,5-trifluorophenyl)-6H-pyridazin-1-ylmethyl]phenyl}carbamate, dihydrochloride, hydrochloride | 516 |

| No. | Name/Structure | ESI |
|---|---|---|
| "A102" | 4-Dimethylaminobutyl {3-[3-(3,5-difluorophenyl)-6-oxo-6H-pyridazin-1-ylmethyl]phenyl}carbamate 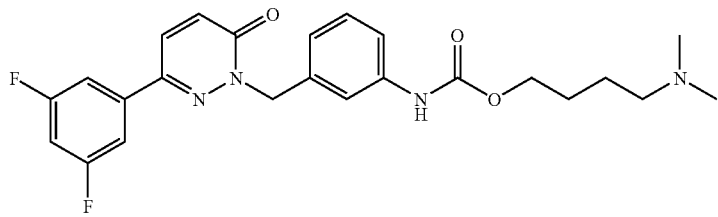 | 457 |
| "A103" | 4-(4-Methylpiperazin-1-yl)butyl {3-[3-(3,5-difluorophenyl)-6-oxo-6H-pyridazin-1-ylmethyl]phenyl}carbamate, dihydrochloride 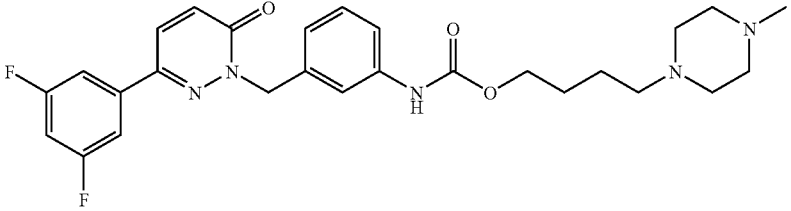 | 512 |
| "A104" | 1-Methylpiperidin-4-ylmethyl {3-[3-(3,5-difluorophenyl)-6-oxo-6H-pyridazin-1-ylmethyl]phenyl}carbamate, hydrochloride 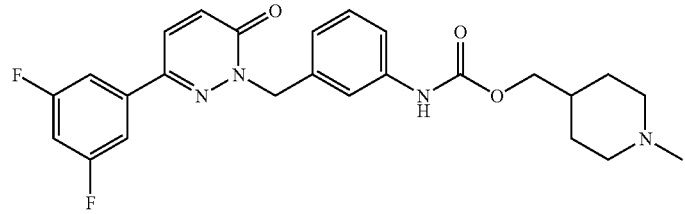 | 469 |
| "A105" | 2-(1-Methylpyrrolidin-2-yl)ethyl {3-[3-(3,5-difluorophenyl)-6-oxo-6H-pyridazin-1-ylmethyl]phenyl}carbamate, hydrochloride 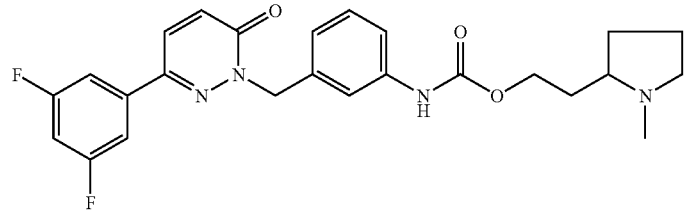 | 469 |
| "A106" | 1-Methylpiperidin-3-ylmethyl {3-[3-(3,5-difluorophenyl)-6-oxo-6H-pyridazin-1-ylmethyl]phenyl}carbamate, hydrochloride 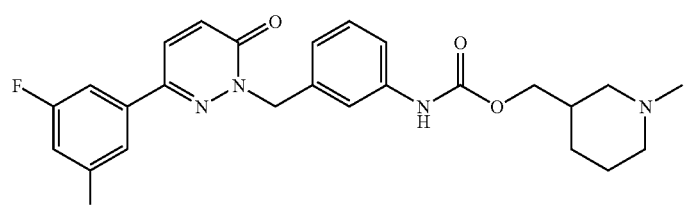 | 469 |

-continued

| No. | Name/Structure | ESI |
|---|---|---|
| "A107" | 3-(4-Methylpiperazin-1-yl)propyl {3-[3-(3-cyanophenyl)-6-oxo-6H-pyridazin-1-ylmethyl]phenyl}carbamate, dihydrochloride 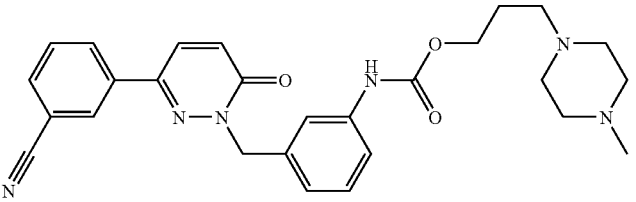 | 487 |

$^1$H-NMR (d$_6$-DMSO): δ [ppm] 2.08 (m, 2 H), 2.82 (s, 3 H), 3.08-3.89 (m, 10 H), 4.15 (t, J = 6 Hz, 2 H), 5.30 (s, 2 H), 7.01 (d, J = 7.5 Hz, 1 H), 7.14 (d, J = 9.5 Hz, 1 H), 7.26 (t, J = 8 Hz, 1 H), 7.40 (d, J = 8 Hz, 1 H), 7.52 (s, 1 H), 7.72 (t, J = 8 Hz, 1 H), 7.93 (d, J = 8 Hz, 1 H), 8.17 (d, J = 9.5 Hz, 1 H), 8.25 (d, J = 8 Hz, 1 H), 8.37 (s, 1 H), 9.72 (s, 1 H), 11.7 (bs, 2 H)

| No. | Name/Structure | ESI |
|---|---|---|
| "A108" | 3-(2-Methoxyethoxy)propyl {3-[3-(3,5-difluorophenyl)-6-oxo-6H-pyridazin-1-ylmethyl]phenyl}carbamate 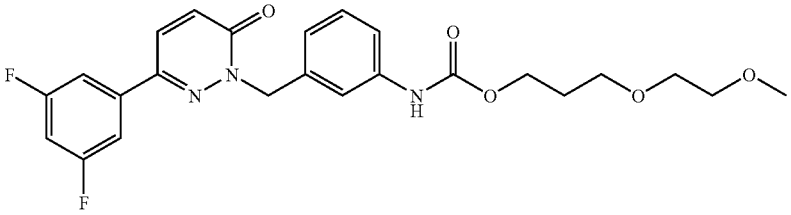 | 474 |
| "A109" | 3-Diethylaminopropyl {3-[3-(3,5-difluorophenyl)-6-oxo-6H-pyridazin-1-ylmethyl]phenyl}carbamate, hydrochloride 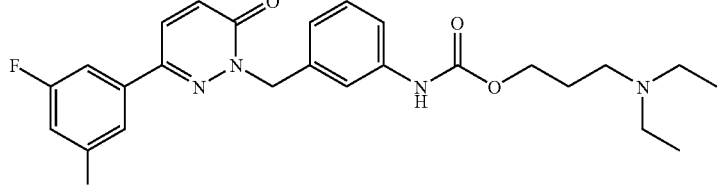 | 471 |
| "A110" | 4-Dimethylaminobutyl {3-[3-(3,5-difluorophenyl)-6-oxo-6H-pyridazin-1-ylmethyl]phenyl}carbamate, hydrochloride 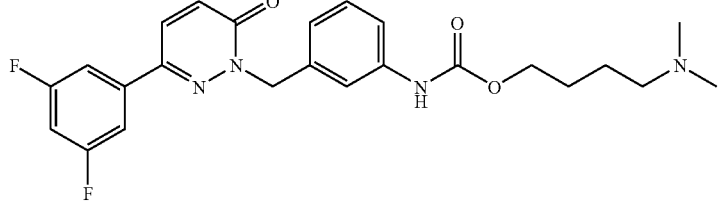 | 457 |
| "A111" | 3-(2-Methoxyethoxy)propyl {3-[3-(3,4-difluorophenyl)-6-oxo-6H-pyridazin-1-ylmethyl]phenyl}carbamate 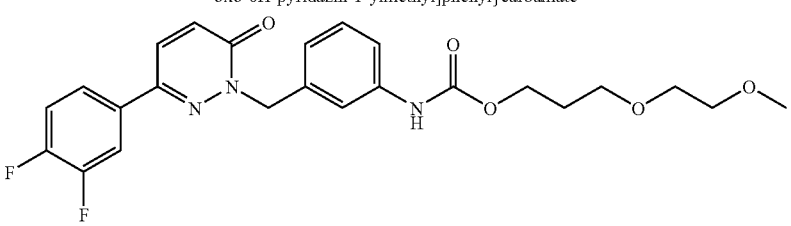 | 474 |

-continued

| No. | Name/Structure | ESI |
|---|---|---|
| "A112" | 4-Dimethylaminobutyl {3-[3-(3,4-difluorophenyl)-6-oxo-6H-pyridazin-1-ylmethyl]phenyl}carbamate, hydrochloride | 457 |
| "A113" | 2-(4-Methylpiperazin-1-yl)ethyl {3-[6-oxo-3-(3,4,5-trifluoro-phenyl)-6H-pyridazin-1-ylmethyl]phenyl}carbamate, di-hydrochloride | 502 |

EXAMPLE 11

The following compounds are obtained analogously to Example 4 by alkylation and hydrogenation

| No. | Name/structure | ESI |
|---|---|---|
| "A114" | 2-(3-Aminobenzyl)-6-(3,5-difluorophenyl)-2H-pyridazin-3-one | 314 |
| "A115" | 2-(3-Aminobenzyl)-6-(3,4-difluorophenyl)-2H-pyridazin-3-one | 314 |
| "A116" | 2-(3-Aminobenzyl)-6-(3,4,5-trifluorophenyl)-2H-pyridazin-3-one | 332 |
| "A117" | 2-(3-Aminobenzyl)-6-(4-fluorophenyl)-2H-pyridazin-3-one | 296 |

EXAMPLE 12

The compound is obtained analogously to Example 3 by alkylation and subsequent reduction using SnCl$_2$

| No. | Name/structure | ESI |
|---|---|---|
| "A118" | 3-[1-(3-Aminobenzyl)-6-oxo-1,6-dihydropyridazin-3-yl]-benzonitrile | 303 |

EXAMPLE 13

The preparation of 2-hydroxyethyl {3-[3-(3,5-difluo-rophenyl)-6-oxo-6Hpyridazin-1-ylmethyl]phenyl}carbamate ("A119"), ESI 402, is carried out analogously to the following scheme

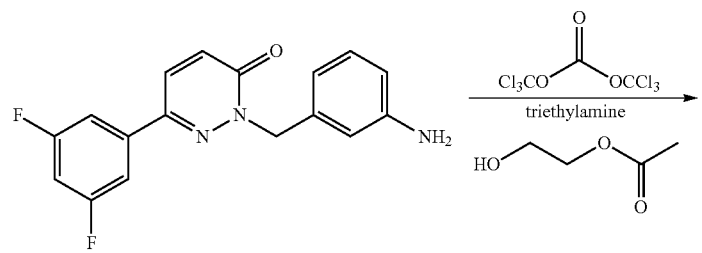

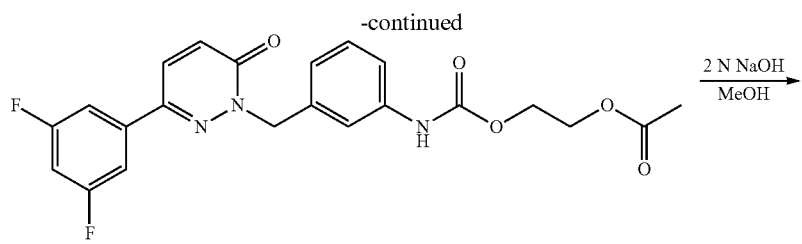

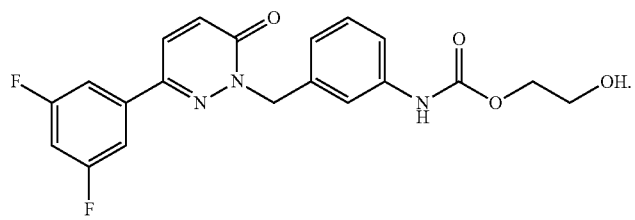

"A119"

An analogous procedure gives 2-hydroxyethyl {3-[3-(3,4-difluorophenyl)-6-oxo-6H-pyridazin-1-ylmethyl]phenyl}carbamate ("A120"), ESI 402.

EXAMPLE 14

The preparation of 3-[3-(3,5-difluorophenyl)-6-oxo-6H-pyridazin-1-ylmethyl]benzoic acid ("A121"), ESI 343, is carried out analogously to the following scheme

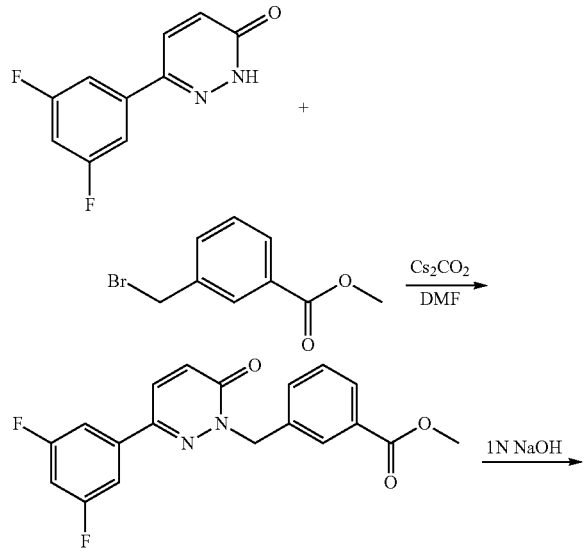

"A121"

The compounds are obtained analogously

| No. | Name/structure | ESI |
|---|---|---|
| "A122" | 6-(3,5-Difluorophenyl)-2-[3-(5-methyloxazol-2-yl)benzyl]-2H-pyridazin-3-one | |
| "A123" | 6-(3,5-Difluorophenyl)-2-[3-(5-oxo-4,5-dihydro-1,3,4-oxadiazol-2-yl)benzyl]-2H-pyridazin-3-one | |

EXAMPLE 15

The preparation of the compounds 2-benzo-1,2,5-thiadiazol-5-ylmethyl-6-(3-fluorophenyl)-2H-pyridazin-3-one ("A124"), 2-(2-amino-1H-benzimidazol-5-ylmethyl)-6-(3-fluorophenyl)-2H-pyridazin-3-one ("A125"), 2-(1H-benzimidazol-5-ylmethyl)-6-(3-fluorophenyl)-2H-pyridazin-3-one ("A126") and 5-[3-(3-fluorophenyl)-6-oxo-6H-pyridazin-1-ylmethyl]-1,3-dihydrobenzimidazol-2-one ("A127")

is carried out analogously to the following scheme

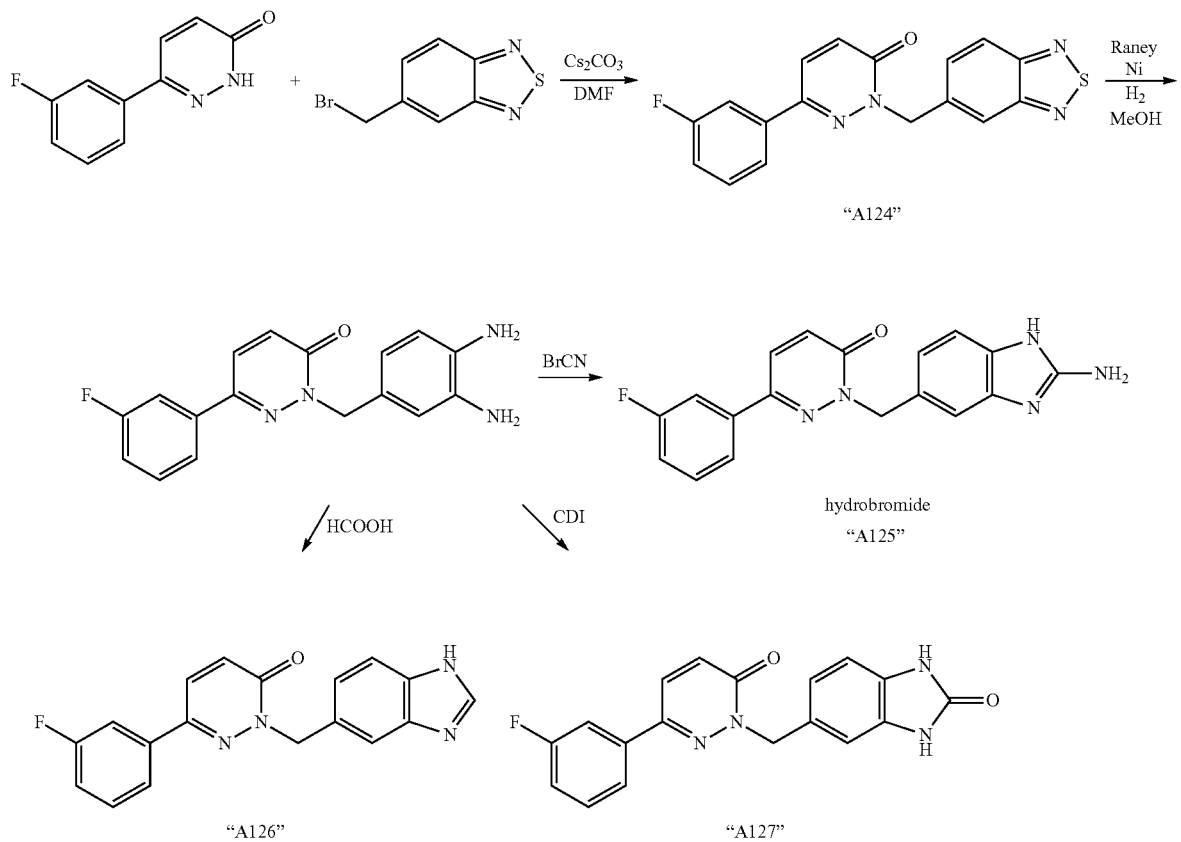

"A124"

"A125"

"A126"

"A127"

15.1 1.64 g (5.04 mmol) of caesium carbonate are added to a solution of 872 mg (4.58 mmol) of 6-(3-fluorophenyl)-2H-pyridazin-3-one and 1.05 g (4.58 mmol) of 5-(bromomethyl)-2,1,3-benzothiadiazole in 9 ml of DMF, and the resultant suspension is stirred at room temperature for 18 hours. Water is added to the reaction mixture, and the resultant precipitate is filtered off, washed with water and dried: 2-benzo-1,2,5-thiadiazol-5-ylmethyl-6-(3-fluorophenyl)-2H-pyridazin-3-one ("A124") as colourless crystals; ESI 339.

15.2 2.0 g of Raney nickel are added to a solution of 1.30 g (3.84 mmol) of 2-benzo-1,2,5-thiadiazol-5-ylmethyl-6-(3-fluorophenyl)-2H-pyridazin-3-one in 100 ml of methanol, and the mixture is shaken for 17 hours at 45° C. under a 2 bar hydrogen atmosphere. The reaction mixture is filtered, and the filtrate is evaporated: 2-(3,4-diaminobenzyl)-6-(3-fluorophenyl)-2H-pyridazin-3-one as brown solid; ESI 311.

15.3 A solution of 155 mg (0.50 mmol) of 2-(3,4-diaminobenzyl)-6-(3-fluorophenyl)-2H-pyridazin-3-one in 1 ml of formic acid is heated at 80° C. for 1 h. The reaction solution is diluted with dichloromethane and washed three times with 2N NaOH. The organic phase is dried over sodium sulfate and evaporated: 2-(1H-benzimidazol-5-ylmethyl)-6-(3-fluorophenyl)-2H-pyridazin-3-one ("A126") as colourless foam; ESI 321.

15.4 63.6 mg (0.60 mmol) of cyanogen bromide are added to a solution of 155 mg (0.50 mmol) of 2-(3,4-diaminobenzyl)-6-(3-fluorophenyl)-2H-pyridazin-3-one in 1 ml of methanol, and the mixture is stirred at room temperature for 17 hours. The reaction mixture is evaporated. The solid residue is digested with tert-butyl methyl ether, filtered, and the residue is dried under reduced pressure: 2-(2-amino-1H-benzimidazol-5-ylmethyl)-6-(3-fluorophenyl)-2H-pyridazin-3-one hydrobromide ("A125") as ochre-yellow solid; ESI 336.

15.5 89.2 mg (0.505 mmol) of 1,1'-carbonyldiimidazole are added to a solution of 155 mg (0.50 mmol) of 2-(3,4-diaminobenzyl)-6-(3-fluorophenyl)-2H-pyridazin-3-one in 1 ml of THF, and the mixture is stirred at room temperature for 48 hours. Water is added to the reaction mixture. The resultant precipitates is filtered off with suction, washed with water and dried under reduced pressure: 5-[3-(3-fluorophenyl)-6-oxo-6H-pyridazin-1-ylmethyl]-1,3-dihydrobenzimidazol-2-one ("A127") as palebrown solid; ESI 337;

$^1$H-NMR ($d_6$-DMSO): δ [ppm] 5.25 (s, 2H), 6.88 (d, J=7.5 Hz, 1H), 7.01 (m, 2H), 7.08 (d, J=9.5 Hz, 1H), 7.30 (dt, $J_1$ =9 Hz, $J_2$=2 Hz, 1H), 7.55 (m, 1H), 7.23 (m, 2H), 8.08 (d, J=9.5 Hz, 1H), 10.52 (s, 1H), 10.57 (s, 1H) ppm.

The following compounds are obtained analogously to the preparation of compounds "A125" and "A126"

2-(2-amino-1H-benzimidazol-5-ylmethyl)-6-(3,5-difluorophenyl)-2H-pyridazin-3-one hydrobromide ("A125a"), ESI 354 and 2-(1H-benzimidazol-5-ylmethyl)-6-(3,5-difluorophenyl)-2H-pyridazin-3-one ("A126a"), ESI 339.

EXAMPLE 16

The preparation of 6-(3,5-difluorophenyl)-2-(3-hydroxybenzyl)-2H-pyridazin-3-one ("A128") is carried out analogously to the following scheme:

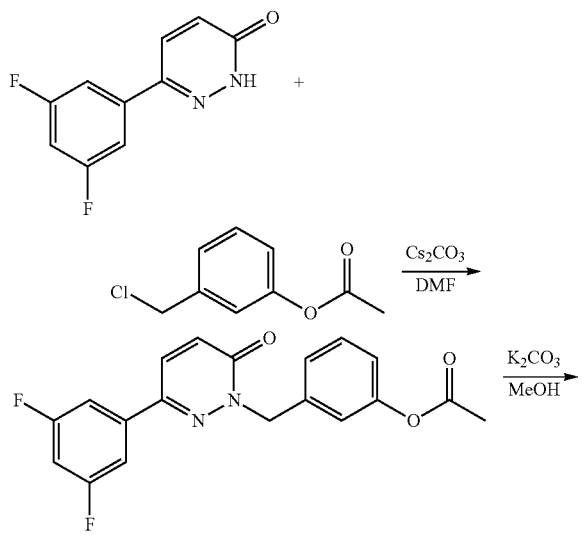

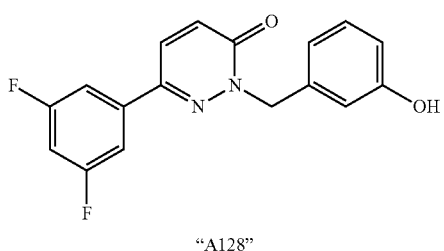

"A128"

16.1 1.63 g (5.00 mmol) of caesium carbonate are added to a solution of 1.04 g (5.00 mmol) of 6-(3,5-difluorophenyl)-2H-pyridazin-3-one and 923 mg (5.00 mmol) of 3-acetoxybenzyl chloride in 10 ml of DMF, and the resultant suspension is stirred at room temperature for 18 hours. Water is added to the reaction mixture, and the resultant precipitate is filtered off, washed with water and dried: 3-[3-(3,5-difluorophenyl)-6-oxo-6H-pyridazin-1-ylmethyl]phenyl acetate as slightly yellowish crystals; ESI 357.

16.2 688 mg (4.98 mmol) of potassium carbonate are added to a solution of 1.68 g (4.73 mmol) of 3-[3-(3,5-difluorophenyl)-6-oxo-6H-pyridazin-1-ylmethyl]phenyl acetate in 10 ml of methanol, and the mixture is stirred at room temperature for 18 hours. The reaction mixture is partitioned between dichloromethane and saturated aqueous potassium hydrogensulfate solution. The organic phase is dried over sodium sulfate and evaporated. The crystalline residue is digested with tert-butyl methyl ether and dried under reduced pressure: 6-(3,5-difluorophenyl)-2-(3-hydroxybenzyl)-2H-pyridazin-3-one as colourless crystals; ESI 315.

EXAMPLE 17

The preparation of 1-{3-[3-(3,5-difluorophenyl)-6-oxo-6H-pyridazin-1-ylmethyl]phenyl}-3-(3-morpholin-4-ylpropyl)urea ("A129") is carried out analogously to the following scheme

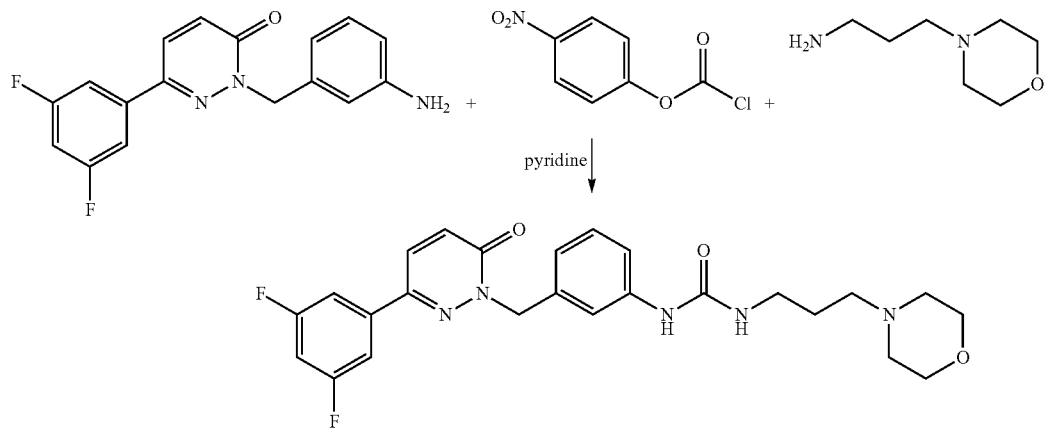

"A129"

111 mg (0.55 mmol) of 4-nitrophenyl chloroformate and 44 µl (0.55 mmol) of pyridine are added to a suspension of 156 mg (0.50 mmol) of 2-(3-aminobenzyl)-6-(3,5-difluorophenyl)-2H-pyridazin-3-one in 3 ml of dichloromethane, and the mixture is stirred at room temperature for 1 hour. 80.1 µl (0.55 mmol) of 3-morpholinopropylamine are then added, and the reaction mixture is stirred at room temperature for 18 hours. The reaction mixture is partitioned between dichloromethane and 2N NaOH. The organic phase is washed with water, dried over sodium sulfate and evaporated. The solid residue is boiled up in tert-butyl methyl ether and, after cooling to room temperature, filtered off with suction. The residue is dried, dissolved in 5 ml of a 0.1 N solution of hydrogen chloride in 2-propanol, and the solution is added dropwise to 50 ml of tert-butyl methyl ether. The resultant precipitate is filtered off, washed with tert-butyl methyl ether and dried: 1-{3-[3-(3,5-difluorophenyl)-6-oxo-6H-pyridazin-1-ylmethyl]phenyl}-3-(3-morpholin-4-ylpropyl)urea hydrochloride ("A129") as colourless solid; ESI 484.

The following compounds are obtained analogously

| No. | Name/structure | ESI |
|---|---|---|
| "A130" | 1-{3-[3-(4-Fluorophenyl)-6-oxo-6H-pyridazin-1-ylmethyl]-phenyl}-3-(1-methylpyrrolidin-3-ylmethyl)urea, hydrochloride | 436 |
| "A131" | 1-{3-[3-(3,5-Difluorophenyl)-6-oxo-6H-pyridazin-1-ylmethyl]phenyl}-3-(3-pyrrolidin-1-ylpropyl)urea, hydrochloride | 468 |
| "A132" | 1-{3-[3-(3,4-Difluorophenyl)-6-oxo-6H-pyridazin-1-ylmethyl]phenyl}-3-(3-pyrrolidin-1-ylpropyl)urea, formate | 468 |
| "A133" | 3-[3-(3,5-Difluorophenyl)-6-oxo-6H-pyridazin-1-ylmethyl]-phenyl (3-dimethylaminopropyl)carbamate, hydrochloride | 443 |

-continued

| No. | Name/structure | ESI |
|---|---|---|
| "A134" | 1-{3-[3-(3,5-Difluorophenyl)-6-oxo-6H-pyridazin-1-yl-methyl]phenyl}-3-(3-dimethylaminopropyl)urea, hydrochloride 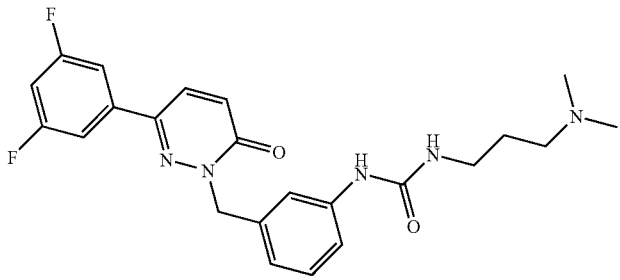 | 442 |
| "A135" | 1-{3-[3-(3,5-Difluorophenyl)-6-oxo-6H-pyridazin-1-yl-methyl]phenyl}-3-(2-morpholin-4-ylethyl)urea, hydrochloride 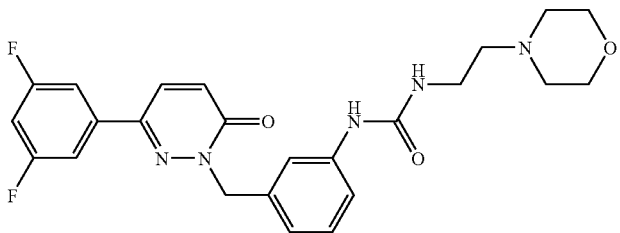 | 470 |
| "A136" | 1-{3-[3-(3,5-Difluorophenyl)-6-oxo-6H-pyridazin-1-yl-methyl]phenyl}-3-[3-(4-methylpiperazin-1-yl)propyl]urea, hydrochloride 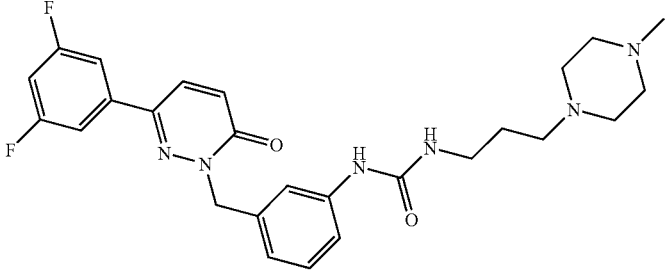 | 497 |
| "A137" | 1-{3-[3-(3,4-Difluorophenyl)-6-oxo-6H-pyridazin-1-yl-methyl]phenyl}-3-(3-dimethylaminopropyl)urea, hydrochloride 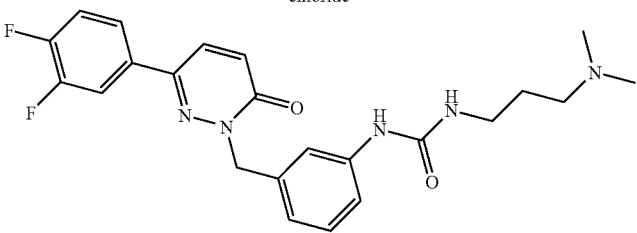 | 442 |
| "A138" | 1-{3-[3-(3,4-Difluorophenyl)-6-oxo-6H-pyridazin-1-yl-methyl]phenyl}-3-(3-morpholin-4-ylpropyl)urea, hydrochloride 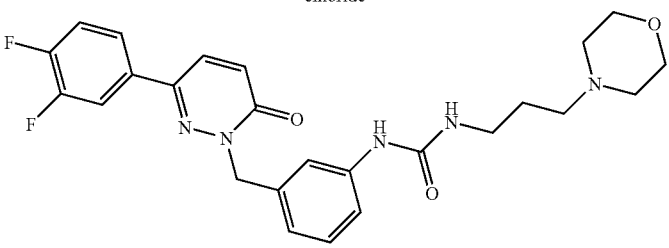 | 484 |

| No. | Name/structure | ESI |
|---|---|---|
| "A139" | 1-{3-[3-(3,4-Difluorophenyl)-6-oxo-6H-pyridazin-1-yl-methyl]phenyl}-3-(2-morpholin-4-ylethyl)urea, hydrochloride | 470 |
| "A140" | 1-{3-[3-(3,4-Difluorophenyl)-6-oxo-6H-pyridazin-1-yl-methyl]phenyl}-3-[3-(4-methylpiperazin-1-yl)propyl]urea, dihydrochloride | 497 |
| "A141" | {3-[3-(3,5-Difluorophenyl)-6-oxo-6H-pyridazin-1-ylmethyl]-phenyl}urea | 357 |

EXAMPLE 18

The preparation of 3-methylaminopropyl {3-[3-(3,5-difluorophenyl)-6-oxo-6H-pyridazin-1-ylmethyl]phenyl}carbamate ("A142") is carried out analogously to the following scheme

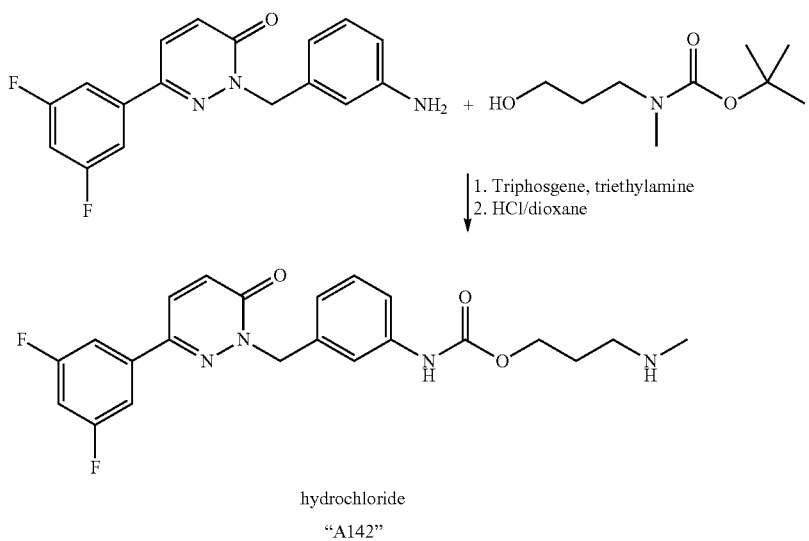

hydrochloride
"A142"

119 mg (0.40 mmol) of bis(trichloromethyl)carbonate are added to a suspension of 316 mg (1.00 mmol) of 2-(3-aminobenzyl)-6-(3-chlorophenyl)-2H-pyridazin-3-one in 4 ml of dichloromethane. 416 µl (3.00 mmol) of triethylamine are then added dropwise with ice-cooling, and the reaction mixture is stirred at room temperature for 10 minutes. 208 mg (1.10 mmol) of tert-butyl 3-(hydroxypropyl)methylcarbamate are then added, and the mixture is stirred at room temperature for 18 hours. The reaction mixture is filtered through sodium sulfate, and the filtrate is chromatographed on a silica-gel column with dichloromethane/methanol as eluent. The product-containing fractions are combined and evaporated, and the residue is dissolved in 2 ml of a 4N solution of hydrogen chloride in dioxane and left at room temperature overnight. The resultant suspension is diluted with tert-butyl methyl ether and filtered with suction, and the residue is dried under reduced pressure: 3-methylaminopropyl {3-[3-(3,5-difluorophenyl)-6-oxo-6H-pyridazin-1-ylmethyl]-phenyl}carbamate hydrochloride ("A142") as colourless crystals; ESI 429.

The following compounds are obtained analogously

| No. | Name/structure | ESI |
|---|---|---|
| "A143" | 2-Piperazin-1-ylethyl {3-[3-(3,5-difluorophenyl)-6-oxo-6H-pyridazin-1-ylmethyl]phenyl}carbamate, dihydrochloride | 470 |

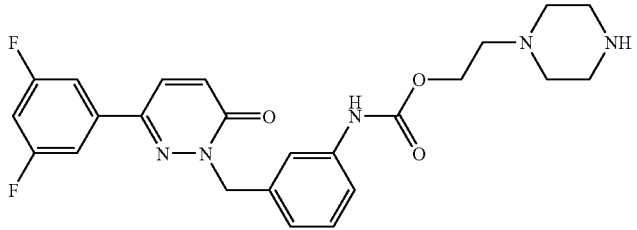

| "A144" | 3-Piperazin-1-ylpropyl {3-[3-(3,4-difluorophenyl)-6-oxo-6H-pyridazin-1-ylmethyl]phenyl}carbamate, dihydro-chloride | 484 |

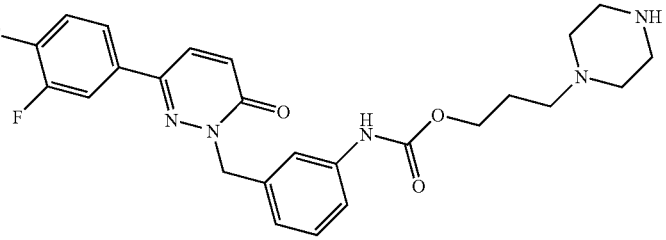

| "A145" | 3-Piperazin-1-ylpropyl {3-[3-(3,5-difluorophenyl)-6-oxo-6H-pyridazin-1-ylmethyl]phenyl}carbamate, dihydro-chloride | 484 |
| "A146" | 2-Piperazin-1-ylethyl {3-[3-(3,4-difluorophenyl)-6-oxo-6H-pyridazin-1-ylmethyl]phenyl}carbamate, dihydrochloride | 470 |

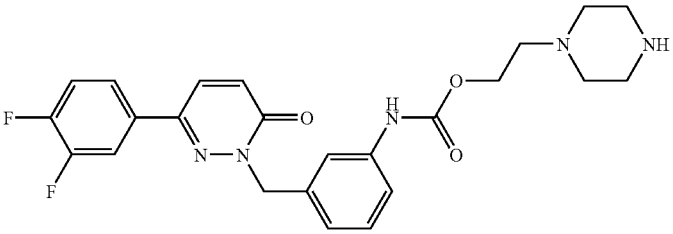

| "A147" | 3-Methylaminopropyl {3-[3-(3,4-difluorophenyl)-6-oxo-6H-pyridazin-1-ylmethyl]phenyl}carbamate, hydrochloride | 429 |

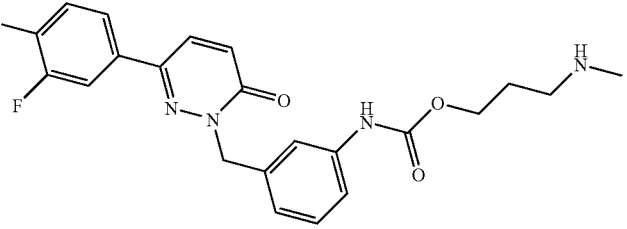

-continued

| No. | Name/structure | ESI |
|---|---|---|
| "A148" | 2-Isopropylaminoethyl {3-[3-(3,4-difluorophenyl)-6-oxo-6H-pyridazin-1-ylmethyl]phenyl}carbamate, hydrochloride 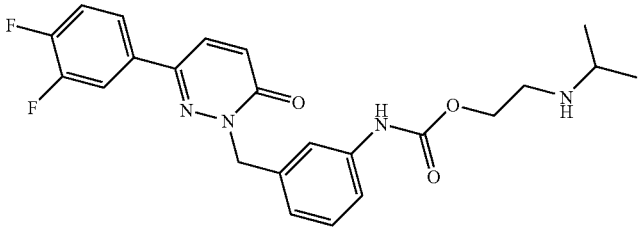 | 443 |
| "A149" | 3-Isopropylaminopropyl {3-[3-(3,4-difluorophenyl)-6-oxo-6H-pyridazin-1-ylmethyl]phenyl}carbamate, hydrochloride 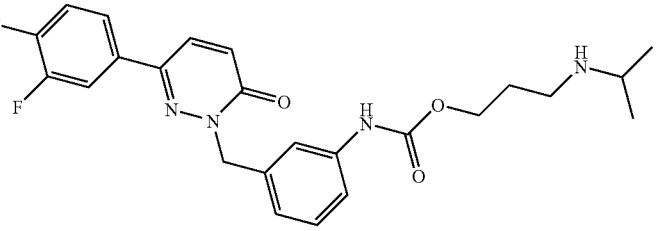 | 457 |
| "A150" | 3-Isopropylaminopropyl {3-[3-(3,5-difluorophenyl)-6-oxo-6H-pyridazin-1-ylmethyl]phenyl}carbamate, hydrochloride 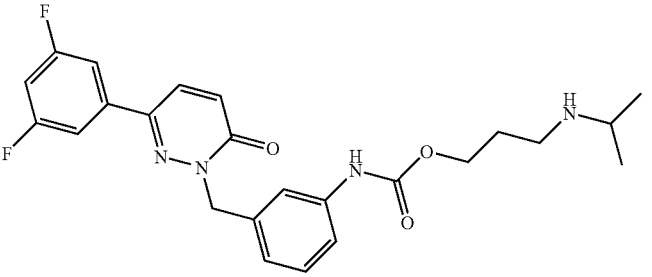 | 457 |
| "A151" | 2-Methylaminoethyl {3-[3-(3,4-difluorophenyl)-6-oxo-6H-pyridazin-1-ylmethyl]phenyl}carbamate, hydrochloride 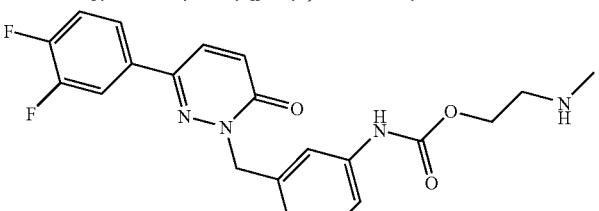 | 415 |
| "A152" | 2-Methylaminoethyl {3-[3-(3,5-difluorophenyl)-6-oxo-6H-pyridazin-1-ylmethyl]phenyl}carbamate, hydrochloride 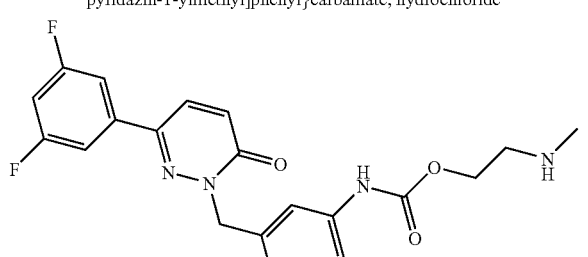 | 415 |

-continued

| No. | Name/structure | ESI |
|---|---|---|
| "A153" | 2-Isopropylaminoethyl {3-[3-(3,5-difluorophenyl)-6-oxo-6H-pyridazin-1-ylmethyl]phenyl}carbamate, hydrochloride 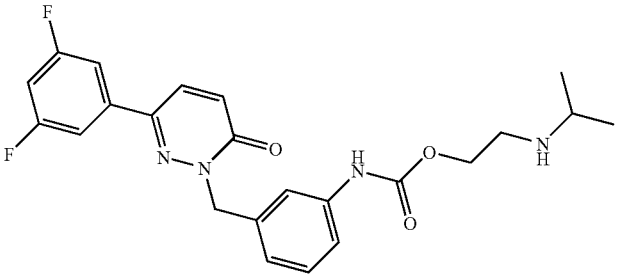 | 443 |
| "A154" | 3-Methylaminopropyl {3-[3-(4-cyanophenyl)-6-oxo-6H-pyridazin-1-ylmethyl]phenyl}carbamate, hydrochloride 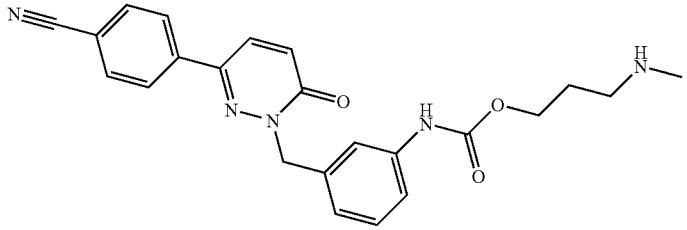 | 418 |
| "A155" | 4-Methylaminobutyl {3-[3-(3,5-difluorophenyl)-6-oxo-6H-pyridazin-1-ylmethyl]phenyl}carbamate, hydrochloride 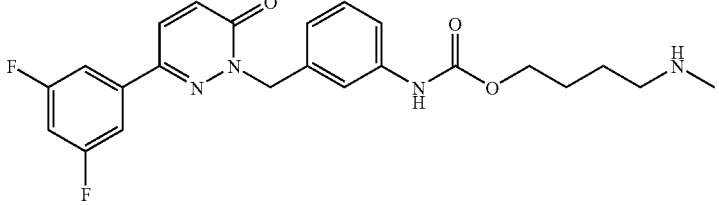 | 443 |
| "A156" | Piperidin-4-ylmethyl {3-[3-(3,5-difluorophenyl)-6-oxo-6H-pyridazin-1-ylmethyl]phenyl}carbamate, hydrochloride 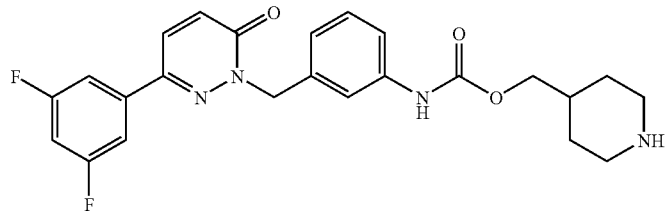 | 455 |
| "A157" | Piperidin-3-ylmethyl {3-[3-(3,5-difluorophenyl)-6-oxo-6H-pyridazin-1-ylmethyl]phenyl}carbamate, hydrochloride 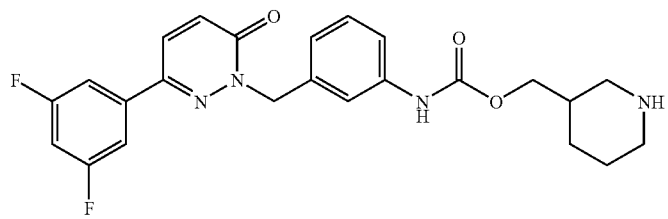 | 455 |

EXAMPLE 19

The preparation of 6-[3-(3,5-difluorophenyl)-6-oxo-6H-pyridazin-1-yl-methyl]-1-(3-dimethylaminopropyl)-1,3-dihydrobenzimidazol-2-one ("A158") is carried out analogously to the following scheme:

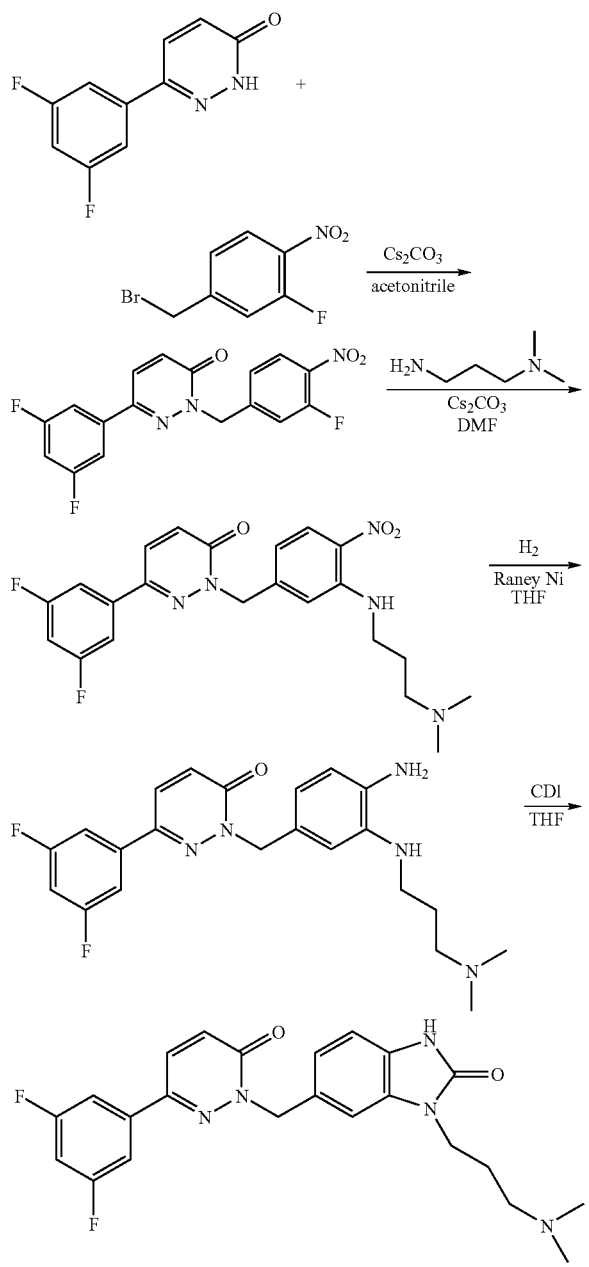

19.1 2.00 g (0.61 mmol) of caesium carbonate are added to a solution of 2.08 g (10.0 mmol) of 6-(3,5-difluorophenyl)-2H-pyridazin-3-one and 2.34 g (10.0 mmol) of 3-fluoro-4-nitrobenzyl bromide in 20 ml of acetonitrile, and the resultant suspension is stirred at room temperature for 18 hours. Water is added to the reaction mixture, and the resultant precipitate is filtered off, washed with water and dried: 6-(3,5-difluorophenyl)-2-(3-fluoro-4-nitrobenzyl)-2H-pyridazin-3-one as colourless crystals; ESI 362.

19.2 326 mg (1.00 mmol) of caesium carbonate and 143 mg (1.40 mmol) of N,N-dimethyltrimethylene diamine are added to a solution of 361 mg (1.00 mmol) of 6-(3,5-difluorophenyl)-2-(3-fluoro-4-nitrobenzyl)-2H-pyridazin-3-one in 2 ml of DMF, and the resultant suspension is stirred at room temperature for 3 hours. Water is added to the reaction mixture. A highly viscous red precipitate forms. This is separated off, washed a number of times with water and dried under reduced pressure. This material is digested with petroleum ether, whereupon crystallisation commences. The solid formed is filtered off with suction, washed with petroleum ether and dried under reduced pressure: 6-(3,5-difluorophenyl)-2-[3-(3-dimethylaminopropylamino)-4-nitrobenzyl]-2H-pyridazin-3-one as yellow-orange crystals; ESI 444.

19.3 400 mg of Raney nickel are added to a solution of 360 mg (0.81 mmol) of 6-(3,5-difluorophenyl)-2-[3-(3-dimethylaminopropylamino)-4-nitrobenzyl]-2H-pyridazin-3-one in 10 ml of THF, and the mixture is hydrogenated. The reaction mixture is filtered, and the filtrate is evaporated: 2-[4-amino-3-(3-dimethylaminopropylamino)benzyl]-6-(3,5-difluorophenyl)-2H-pyridazin-3-one as yellow highly viscous oil; ESI 414.

19.4 142 mg (0.88 mmol) of 1,1'-carbonyldiimidazole are added to a solution of 330 mg (0.80 mmol) of 2-[4-amino-3-(3-dimethylaminopropylamino)benzyl]-6-(3,5-difluorophenyl)-2H-pyridazin-3-one in 2 ml of THF, and the mixture is stirred at room temperature overnight. The reaction mixture is partitioned between dichloromethane and water. The organic phase is dried over sodium sulfate and evaporated. The residue is purified by preparative HPLC: 6-[3-(3,5-difluorophenyl)-6-oxo-6Hpyridazin-1-ylmethyl]-1-(3-dimethylaminopropyl)-1,3-dihydrobenzimidazol-2-one formate ("A158") as colourless solid; ESI 440.

The following compounds are obtained analogously

| No. | Name/structure | ESI |
|---|---|---|
| "A159" | 6-[3-(3,5-Difluorophenyl)-6-oxo-6H-pyridazin-1-ylmethyl]-1-(2-dimethylaminoethyl)-1,3-dihydrobenzimidazol-2-one, hydrochloride | 426 |
| "A160" | 6-[3-(3,5-Difluorophenyl)-6-oxo-6H-pyridazin-1-ylmethyl]-1-(4-dimethylaminobutyl)-1,3-dihydrobenzimidazol-2-one, hydrochloride | 454 |

EXAMPLE 20

The preparation of 6-(3,5-difluorophenyl)-2-(1H-indazol-5-ylmethyl)-2H-pyridazin-3-one ("A161") is carried out analogously to the following scheme:

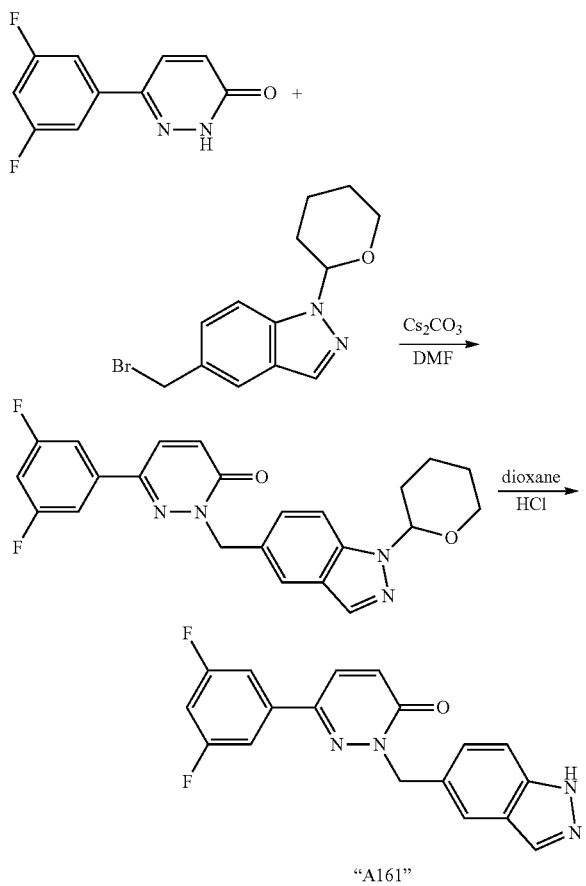

"A161"

20.1 162 mg (0.50 mmol) of caesium carbonate are added to a solution of 104 mg (0.50 mmol) of 6-(3,5-difluorophenyl)-2H-pyridazin-3-one and 147 mg (0.50 mmol) of 5-bromomethyl-1-(tetrahydropyran-2-yl)indazole (prepared by the method of J.-H. Sun et al., J. Org. Chem. 1997, 62, 5627-5629) in 1 ml of DMF, and the resultant suspension is stirred at room temperature for 18 hours. The reaction mixture is partitioned between water and dichloromethane. The organic phase is dried over sodium sulfate and evaporated, and the residue is chromatographed on a silica-gel column with dichloromethane/methanol as eluent: 6-(3,5-difluorophenyl)-2-[1-(tetrahydropyran-2-yl)-1H-indazol-5-ylmethyl]-2H-pyridazin-2-one as colourless solid; ESI 423.

20.2 1 ml of 25% aqueous hydrochloric acid is added to a solution of 95 mg of 6-(3,5-difluorophenyl)-2-[1-(tetrahydropyran-2-yl)-1H-indazol-5-ylmethyl]-2H-pyridazin-2-one in 2 ml of dioxane, and the mixture is left at room temperature overnight. The reaction mixture is evaporated, and the precipitate is filtered off with suction, washed with tert-butyl methyl ether and dried under reduced pressure: 6-(3,5-difluorophenyl)-2-(1H-indazol-5-ylmethyl)-2H-pyridazin-3-one ("A161") as colourless solid; ESI 339.

The following compounds are obtained analogously

| No. | Name/structure | ESI |
|---|---|---|
| "A162" | 4-[1-(1H-Indazol-5-ylmethyl)-6-oxo-1,6-dihydropyridazin-3-yl]benzonitrile | 328 |
| "A169" | 5-[3-(3,5-Difluorophenyl)-6-oxo-6H-pyridazin-1-ylmethyl]-1,3-dihydrobenzimidazol-2-one | 355 |

EXAMPLE 21

The preparation of
6-(3,5-difluorophenyl)-2-quinolin-6-ylmethyl-2H-pyridazin-3-one ("A51"),
6-(3,5-difluorophenyl)-2-(1-oxyquinolin-6-ylmethyl)-2H-pyridazin-3-one ("A163") and
6-[3-(3,5-difluorophenyl)-6-oxo-6H-pyridazin-1-ylmethyl]-1H-quinolin-2-one ("A164")
is carried out analogously to the following scheme:

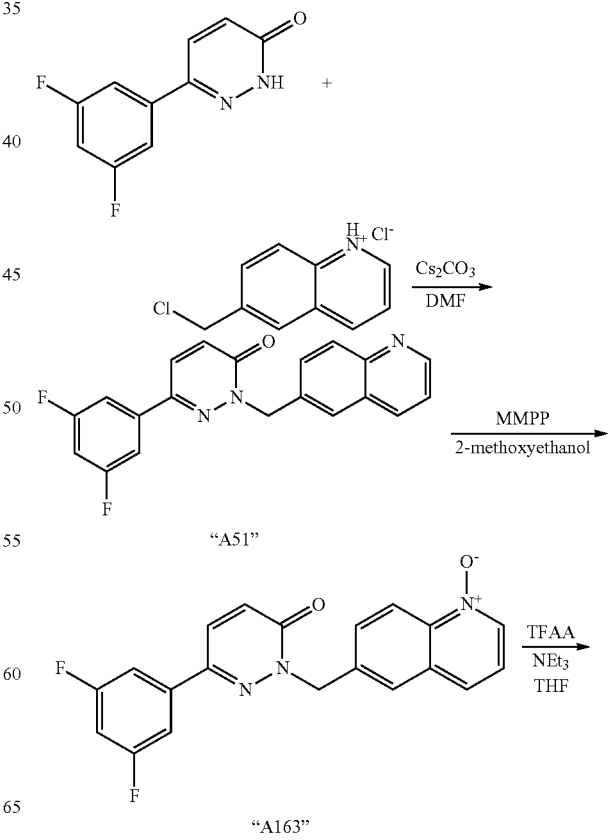

"A163"

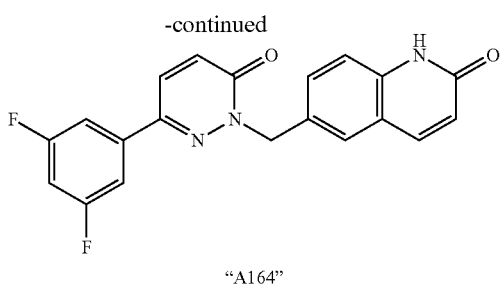

"A164"

21.1 214 mg (1.00 mmol) of 6-chloromethylquinolinium chloride and 489 mg (1.50 mmol) of caesium carbonate are added successively to a solution of 208 mg (1.00 mmol) of 6-(3,5-difluorophenyl)-2H-pyridazin-3-one in 4 ml of DMF, and the resultant suspension is stirred at room temperature for 18 hours. Water is added to the reaction mixture, and the resultant precipitate is filtered off with suction, washed with water and dried under reduced pressure: 6-(3,5-difluorophenyl)-2-quinolin-6-ylmethyl-2H-pyridazin-3-one ("A51") as colourless crystals; ESI 350.

21.2 542 mg of magnesium monoperoxyphthalate hexahydrate are added to a solution of 306 mg (0.876 mmol) of 6-(3,5-difluorophenyl)-2-quinolin-6-ylmethyl-2H-pyridazin-3-one in 4 ml of 2-methoxyethanol, and the resultant suspension is stirred at room temperature for 40 hours. Water is added to the reaction mixture, and the resultant precipitate is filtered off with suction, washed with water and dried under reduced pressure: 6-(3,5-difluorophenyl)-2-(1-oxyquinolin-6-ylmethyl)-2H-pyridazin-3-one ("A163") as colourless solid; ESI 366.

21.3 75 mg (0.75 mmol) of triethylamine and 521 mg (2.48 mmol) of trifluoroacetic anhydride are added to a solution of 91 mg (0.25 mmol) of 6-(3,5-difluorophenyl)-2-(1-oxyquinolin-6-ylmethyl)-2H-pyridazin-3-one in 1 ml of THF, and the reaction mixture is stirred at room temperature for 30 minutes. The reaction mixture is partitioned between 5% aqueous sodium hydrogencarbonate solution and ethyl acetate. The organic phase is dried, dried over sodium sulfate and evaporated. The residue is purified by preparative HPLC: 6-[3-(3,5-difluorophenyl)-6-oxo-6Hpyridazin-1-ylmethyl]-1H-quinolin-2-one ("A164") as colourless solid; ESI 366.

EXAMPLE 22

The preparation of 2-(3-amino-1H-indazol-5-ylmethyl)-6-(3,5-difluorophenyl)-2H-pyridazin-3-one ("A165") is carried out analogously to the following scheme:

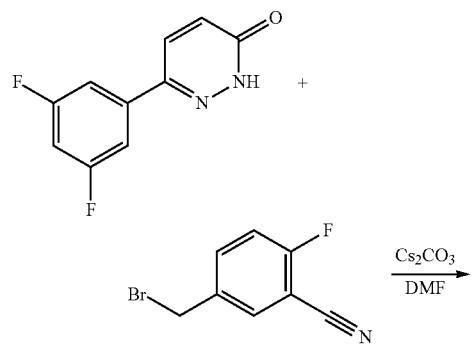

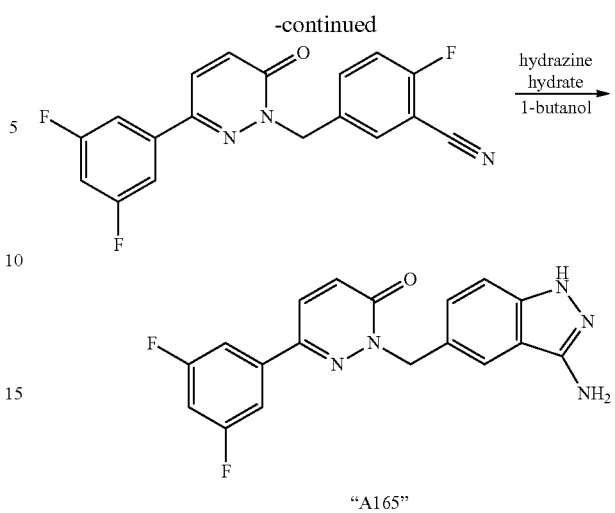

"A165"

22.1 326 mg (1.00 mmol) of caesium carbonate are added to a solution of 208 mg (1.00 mmol) of 6-(3,5-difluorophenyl)-2H-pyridazin-3-one and 214 mg (1.00 mmol) of 5-bromomethyl-2-fluorobenzonitrile in 2 ml of DMF, and the resultant suspension is stirred at room temperature for 18 hours. Water is added to the reaction mixture, and the resultant precipitate is filtered off with suction, washed with water and dried under reduced pressure. The crude product is chromatographed on a silica-gel column with dichloromethane/methanol as eluent: 5-[3-(3,5-difluorophenyl)-6-oxo-6Hpyridazin-1-ylmethyl]-2-fluorobenzonitrile as colourless solid; ESI 342.

22.2 0.14 ml (2.8 mmol) of hydrazine hydrate is added to a solution of 239 mg (0.7 mmol) of 5-[3-(3,5-difluorophenyl)-6-oxo-6H-pyridazin-1-ylmethyl]-2-fluorobenzonitrile in 2.5 ml of butanol, and the mixture is stirred at 100° C. for 18 hours. The reaction mixture is evaporated. The residue is dissolved in 1 ml of a 0.1 N solution of hydrogen chloride in 2-propanol at elevated temperature and cooled to room temperature. The resultant precipitate is filtered off with suction, washed with tert-butyl methyl ether and dried under reduced pressure: 2-(3-amino-1H-indazol-5-ylmethyl)-6-(3,5-difluorophenyl)-2H-pyridazin-3-one hydrochloride ("A165") as colourless crystals; ESI 390.

EXAMPLE 23

Hydrolysis of "A107" using 2N HCl in methanol gives 3-(4-methylpiperazin-1-yl)propyl {3-[3-(3-carbamoylphenyl)-6-oxo-6H-pyridazin-1-ylmethyl]phenyl}carbamate ("A166"), dihydrochloride, ESI 505

"A166"

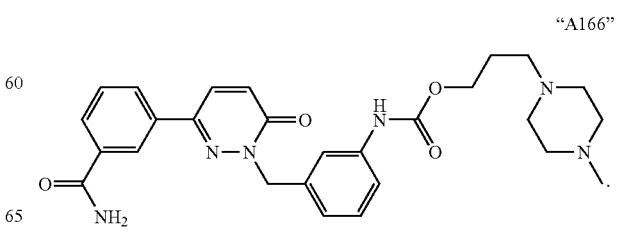

EXAMPLE 24

The following compounds are obtained analogously to Example 10

| No. | Name/structure | ESI |
|---|---|---|
| "A167" | | |
| "A168" | | |

EXAMPLE 25

270 mg of diisopropyl azodicarboxylate are added dropwise to a suspension of 160 mg of "A43a", 116 mg of 2-(dimethylamino)ethanol and 440 mg of triphenylphosphine (polymer-bound) in 4 ml of dichloromethane/THF (1:1), and the mixture is stirred at room temperature for a further 16 hours. Conventional work-up gives 26 mg of 1-(3-{3-[3-(2-dimethylaminoethoxy)phenyl]-6-oxo-6H-pyridazin-1-ylmethyl}phenyl)-3-ethylurea hydrochloride ("A43b"), ESI 436

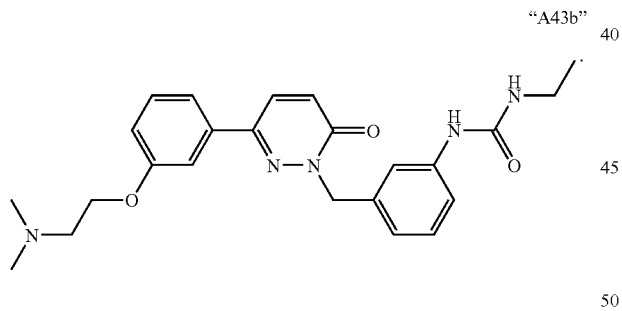

"A43b"

Pharmacological Data
Met kinase inhibition (enzyme assay)

TABLE 1

| Compound No. | $IC_{50}$ |
|---|---|
| "A2" | A |
| "A3" | A |
| "A4" | A |
| "A5" | A |
| "A6" | A |
| "A7" | A |
| "A9" | A |
| "A10" | A |
| "A12" | A |
| "A14" | A |
| "A15" | A |

TABLE 1-continued

| | |
|---|---|
| "A16" | A |
| "A17" | A |
| "A18" | A |
| "A19" | A |
| "A20" | A |
| "A38" | A |
| "A56" | A |
| "A61" | A |
| "A67" | A |
| "A71" | A |
| "A74" | A |
| "A75" | A |
| "A78" | A |
| "A81" | A |
| "A88" | A |
| "A91" | A |
| "A92" | A |
| "A95" | A |
| "A101" | A |
| "A103" | A |
| "A105" | A |
| "A106" | A |
| "A107" | A |
| "A109" | A |
| "A110" | A |
| "A127" | A |
| "A142" | A |
| "A143" | A |
| "A145" | A |
| "A155" | A |
| "A156" | A |
| "A161" | A |
| "A169" | A |

$IC_{50}$: 10 nM-1 µM = A
1 µM-10 µM = B
>10 mM = C

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound selected from the following compounds:

| No. | Structure and/or name |
|---|---|
| "A1" | |
| "A2" | |
| "A3" | |
| "A4" | |
| "A5" | |
| "A6" | |
| "A7" | |
| "A8" | |
| "A9" | |

| No. | Structure and/or name |
|---|---|
| "A10" | (structure) |
| "A11" | (structure) |
| "A12" | (structure) |
| "A13" | (structure) |
| "A14" | (structure) |
| "A15" | (structure) |
| "A16" | (structure) |
| "A17" | (structure) |

| No. | Structure and/or name |
|---|---|
| "A18" | (structure) |
| "A19" | (structure) |
| "A20" | (structure) |
| "A21" | (structure) |
| "A22" | (structure) |
| "A23" | (structure) |
| "A24" | (structure) |
| "A25" | (structure) |
| "A25a" | (structure) |

| No. | Structure and/or name |
|---|---|
| "A26" | |
| "A27" | |
| "A28" | |
| "A29" | |
| "A30" | |
| "A31" | |
| "A32" | |
| "A33" | |

| No. | Structure and/or name |
|---|---|
| "A34" | |
| "A35" | |
| "A36" | |
| "A37" | |
| "A38" | |
| "A39" | |
| "A40" | |
| "A41" | |
| "A42" | |

-continued

| No. | Structure and/or name |
|---|---|
| "A43" | 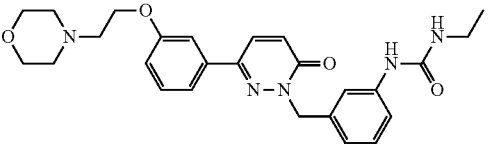 |
| "A43a" | 1-Ethyl-3-{3-[3-(3-hydroxyphenyl)-6-oxo-6H-pyridazin-1-yl-methyl]phenyl}urea |
| "A43b" | 1-(3-{3-[3-(2-Dimethylaminoethoxy)phenyl]-6-oxo-6H-pyridazin-1-ylmethyl}phenyl)-3-ethylurea |
| "A44" | 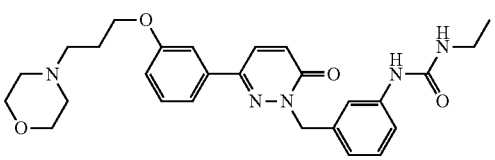 |
| "A45" | 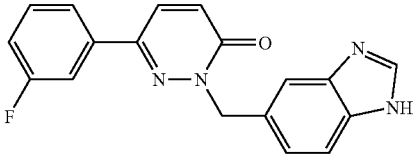 |
| "A45a" | 2-(2-Amino-1H-benzimidazol-5-ylmethyl)-6-(3-fluoropheny)-2H-pyridazin-3-one |
| "A46" | 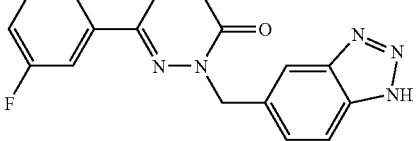 |
| "A47" | 2-Benzo-1,2,5-thiadiazol-5-ylmethyl-6-(3-fluorophenyl)-2H-pyridazin-3-one 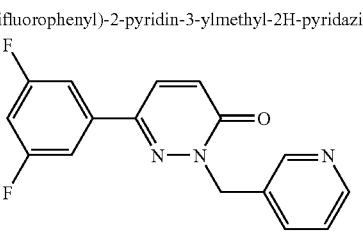 |
| "A48" | 6-(3,5-Difluorophenyl)-2-pyridin-3-ylmethyl-2H-pyridazin-3-one 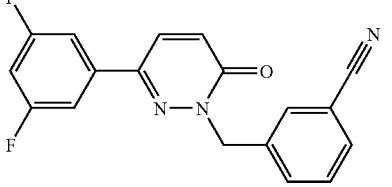 |
| "A49" | 6-(3,5-Difluorophenyl)-2-(3-cyanobenzyl)-2H-pyridazin-3-one 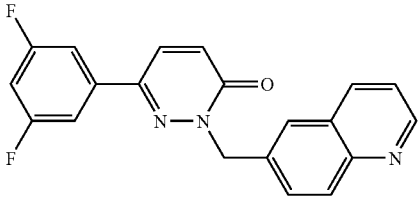 |
| "A50" | 6-(3,5-Difluorophenyl)-2-(3-methoxycarbonylbenzyl)-2H-pyridazin-3-one |

-continued

| No. | Structure and/or name |
|---|---|
| "A51" | 6-(3,5-Difluorophenyl)-2-quinolin-6-ylmethyl-2H-pyridazin-3-one 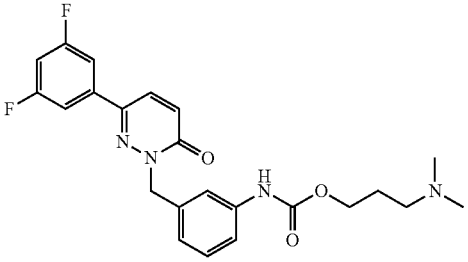 |
| "A52" | 6-(3,4-Difluorophenyl)-2-quinolin-6-ylmethyl-2H-pyridazin-3-one |
| "A53" | 6-(4-Fluorophenyl)-2-quinolin-6-ylmethyl-2H-pyridazin-3-one |
| "A54" | 6-(3,5-Difluorophenyl)-2-pyridin-4-ylmethyl-2H-pyridazin-3-one |
| "A55" | 6-(3,5-Difluorophenyl)-2-(3-acetamidobenzyl)-2H-pyridazin-3-one |
| "A56" | 3-Dimethylaminopropyl {3-[3-(3,5-difluorophenyl)-6-oxo-6H-pyridazin-1-ylmethyl]phenyl}carbamate 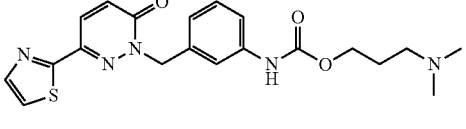 |
| "A57" | 3-Dimethylaminopropyl [3-(6-oxo-3-thiazol-2-yl-6H-pyridazin-1-ylmethyl)phenyl]carbamate 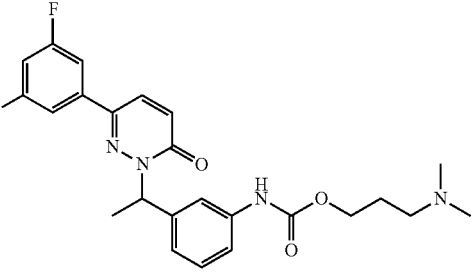 |
| "A58" | 3-Dimethylaminopropyl (3-{1-[3-(3,5-difluorophenyl)-6-oxo-6H-pyridazin-1-yl]ethyl}phenyl)carbamate |
| "A59" | 3-Dimethylaminopropyl {3-[3-(3,4-difluorophenyl)-6-oxo-6H-pyridazin-1-ylmethyl]phenyl}carbamate |
| "A60" | 3-Dimethylaminopropyl {3-[3-(3,4,5-trifluorophenyl)-6-oxo-6H-pyridazin-1-ylmethyl]phenyl}carbamate |
| "A61" | 3-Dimethylaminopropyl {3-[3-(3-cyanophenyl)-6-oxo-6H-pyridazin-1-ylmethyl]phenyl}carbamate |
| "A62" | 3-Dimethylaminopropyl {3-[3-(2,3-difluorophenyl)-6-oxo-6H-pyridazin-1-ylmethyl]phenyl}carbamate |
| "A63" | 3-Dimethylaminopropyl {3-[3-(2,4-difluorophenyl)-6-oxo-6H-pyridazin-1-ylmethyl]phenyl}carbamate |
| "A64" | 3-Dimethylaminopropyl {3-[3-(3,5-dichlorophenyl)-6-oxo-6H-pyridazin-1-ylmethyl]phenyl}carbamate |

-continued

| No. | Structure and/or name |
|---|---|
| "A65" | 3-Dimethylaminopropyl [3-(6-oxo-3-pyridin-3-yl-6H-pyridazin-1-ylmethyl)phenyl]carbamate 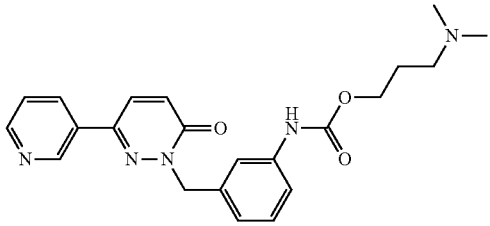 |
| "A66" | 3-Dimethylaminopropyl {3-[3-(4-cyanophenyl)-6-oxo-6H-pyridazin-1-ylmethyl]phenyl}carbamate |
| "A67" | 3-Morpholin-4-ylpropyl {3-[3-(3,5-difluorophenyl)-6-oxo-6H-pyridazin-1-ylmethyl]phenyl}carbamate 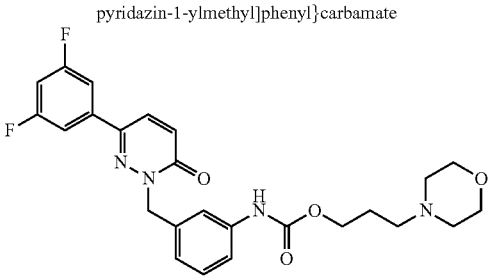 |
| "A68" | 3-Morpholin-4-ylpropyl {3-[3-(3,4-difluorophenyl)-6-oxo-6H-pyridazin-1-ylmethyl]phenyl}carbamate |
| "A69" | 3-Morpholin-4-ylpropyl {3-[3-(4-fluorophenyl)-6-oxo-6H-pyridazin-1-ylmethyl]phenyl}carbamate |
| "A70" | 3-Morpholin-4-ylpropyl [3-(6-oxo-3-thiazol-2-yl-6H-pyridazin-1-ylmethyl)phenyl]carbamate 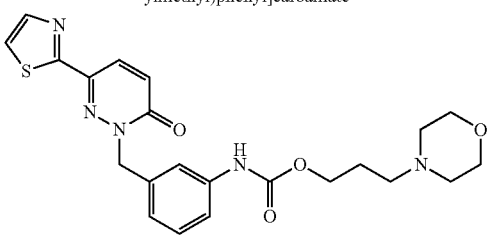 |
| "A71" | 3-Morpholin-4-ylpropyl [3-(6-oxo-3-thiophen-2-yl-6H-pyridazin-1-ylmethyl)phenyl]carbamate 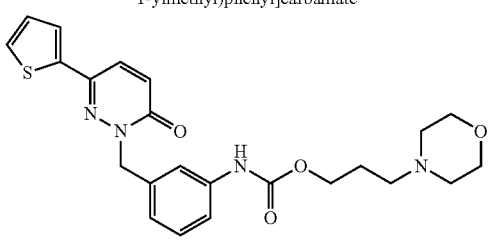 |
| "A72" | 3-Morpholin-4-ylpropyl (3-{1-[3-(3,5-difluorophenyl)-6-oxo-6H-pyridazin-1-yl]ethyl}phenyl)carbamate 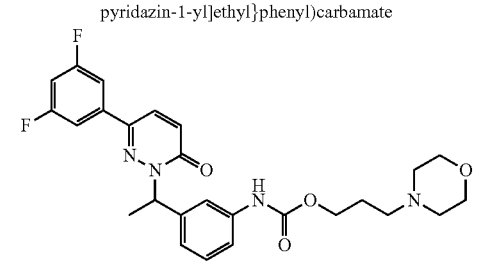 |

-continued

| No. | Structure and/or name |
|---|---|
| "A73" | 3-Pyrrolidin-1-ylpropyl {3-[3-(3,4-difluorophenyl)-6-oxo-6H-pyridazin-1-ylmethyl]phenyl}carbamate 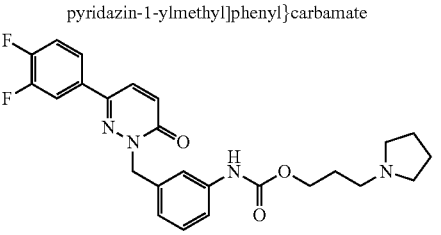 |
| "A73a" | 2-Pyrrolidin-1-ylethyl {3-[3-(3,4-difluorophenyl)-6-oxo-6H-pyridazin-1-ylmethyl]phenyl}carbamate |
| "A74" | 3-Pyrrolidin-1-ylpropyl {3-[3-(3,5-difluorophenyl)-6-oxo-6H-pyridazin-1-ylmethyl]phenyl}carbamate |
| "A75" | 3-Methoxypropyl {3-[3-(3,5-difluorophenyl)-6-oxo-6H-pyridazin-1-ylmethyl]phenyl}carbamate 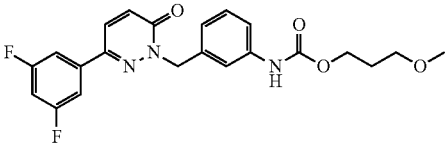 |
| "A76" | 3-Methoxypropyl {3-[3-(3,4-difluorophenyl)-6-oxo-6H-pyridazin-1-ylmethyl]phenyl}carbamate |
| "A77" | 2-Morpholin-4-ylethyl {3-[3-(3,5-difluorophenyl)-6-oxo-6H-pyridazin-1-ylmethyl]phenyl}carbamate |
| "A78" | 3-Morpholin-4-ylpropyl {3-[6-oxo-3-(3,4,5-trifluorophenyl)-6H-pyridazin-1-ylmethyl]phenyl}carbamate |
| "A79" | 3-Pyrrolidin-1-ylpropyl {3-[6-oxo-3-(3,4,5-trifluorophenyl)-6H-pyridazin-1-ylmethyl]phenyl}carbamate |
| "A80" | 2-Dimethylaminoethyl {3-[3-(3,5-difluorophenyl)-6-oxo-6H-pyridazin-1-ylmethyl]phenyl}carbamate |

| No. | Structure and/or name |
|---|---|
| "A81" | 2-Morpholin-4-ylethyl {3-[3-(3,4-difluorophenyl)-6-oxo-6H-pyridazin-1-ylmethyl]phenyl}carbamate |
| "A82" | 2-Dimethylaminoethyl {3-[3-(3,4-difluorophenyl)-6-oxo-6H-pyridazin-1-ylmethyl]phenyl}carbamate |
| "A83" | 2-Pyrrolidin-1-ylethyl {3-[3-(3,5-difluorophenyl)-6-oxo-6H-pyridazin-1-ylmethyl]phenyl}carbamate |
| "A84" | 2-Methoxyethyl {3-[3-(3,5-difluorophenyl)-6-oxo-6H-pyridazin-1-ylmethyl]phenyl}carbamate |
| "A85" | 2-Methoxyethyl {3-[3-(3,4-difluorophenyl)-6-oxo-6H-pyridazin-1-ylmethyl]phenyl}carbamate |
| "A86" | 3-Morpholin-4-ylpropyl {3-[3-(2,4-difluorophenyl)-6-oxo-6H-pyridazin-1-ylmethyl]phenyl}carbamate |
| "A87" | 3-Morpholin-4-ylpropyl {3-[3-(2,3-difluorophenyl)-6-oxo-6H-pyridazin-1-ylmethyl]phenyl}carbamate |
| "A88" | 3-Morpholin-4-ylpropyl {3-[3-(3-cyanophenyl)-6-oxo-6H-pyridazin-1-ylmethyl]phenyl}carbamate |
| "A89" | 2-Morpholin-4-ylethyl {3-[3-(3,4-difluorophenyl)-6-oxo-6H-pyridazin-1-ylmethyl]phenyl}carbamate |
| "A90" | 3-(4-Methylpiperazin-1-yl)propyl {3-[3-(3,4-difluorophenyl)-6-oxo-6H-pyridazin-1-ylmethyl]phenyl}carbamate |
| "A91" | 3-(4-Methylpiperazin-1-yl)propyl {3-[3-(3,5-difluorophenyl)-6-oxo-6H-pyridazin-1-ylmethyl]phenyl}carbamate |
| "A92" | 2-(4-Methylpiperazin-1-yl)ethyl {3-[3-(3,4-difluorophenyl)-6-oxo-6H-pyridazin-1-ylmethyl]phenyl}carbamate |
| "A93" | 2-(4-Methylpiperazin-1-yl)ethyl {3-[3-(3,5-difluorophenyl)-6-oxo-6H-pyridazin-1-ylmethyl]phenyl}carbamate |
| "A94" | 2-(2-Methoxyethoxy)ethyl {3-[3-(3,5-difluorophenyl)-6-oxo-6H-pyridazin-1-ylmethyl]phenyl}carbamate |
| "A95" | 2-Morpholin-4-ylethyl {3-[6-oxo-3-(3,4,5-trifluorophenyl)-6H-pyridazin-1-ylmethyl]phenyl}carbamate |
| "A96" | 3-Morpholin-4-ylpropyl {3-[3-(3,5-dichlorophenyl)-6-oxo-6H-pyridazin-1-ylmethyl]phenyl}carbamate |

-continued

| No. | Structure and/or name |
|---|---|
| "A97" | 2-(2-Methoxyethoxy)ethyl {3-[3-(3,4-difluorophenyl)-6-oxo-6H-pyridazin-1-ylmethyl]phenyl}carbamate |
| "A98" | 1-Methylpiperidin-4-yl {3-[3-(3,5-difluorophenyl)-6-oxo-6H-pyridazin-1-ylmethyl]phenyl}carbamate |
| "A99" | 1-Methylpiperidin-4-yl {3-[3-(3,4-difluorophenyl)-6-oxo-6H-pyridazin-1-ylmethyl]phenyl}carbamate |
| "A100" | 2-Morpholin-4-ylethyl {3-[3-(4-cyanophenyl)-6-oxo-6H-pyridazin-1-ylmethyl]phenyl}carbamate |
| "A101" | 3-(4-Methylpiperazin-1-yl)propyl {3-[6-oxo-3-(3,4,5-trifluorophenyl)-6H-pyridazin-1-ylmethyl]phenyl}carbamate |
| "A102" | 4-Dimethylaminobutyl {3-[3-(3,5-difluorophenyl)-6-oxo-6H-pyridazin-1-ylmethyl]phenyl}carbamate |
| "A103" | 4-(4-Methylpiperazin-1-yl)butyl {3-[3-(3,5-difluorophenyl)-6-oxo-6H-pyridazin-1-ylmethyl]phenyl}carbamate |
| "A104" | 1-Methylpiperidin-4-ylmethyl {3-[3-(3,5-difluorophenyl)-6-oxo-6H-pyridazin-1-ylmethyl]phenyl}carbamate |
| "A105" | 2-(1-Methylpyrrolidin-2-yl)ethyl {3-[3-(3,5-difluorophenyl)-6-oxo-6H-pyridazin-1-ylmethyl]phenyl}carbamate |
| "A106" | 1-Methylpiperidin-3-ylmethyl {3-[3-(3,5-difluorophenyl)-6-oxo-6H-pyridazin-1-ylmethyl]phenyl}carbamate |
| "A107" | 3-(4-Methylpiperazin-1-yl)propyl {3-[3-(3-cyanophenyl)-6-oxo-6H-pyridazin-1-ylmethyl]phenyl}carbamate |
| "A108" | 3-(2-Methoxyethoxy)propyl {3-[3-(3,5-difluorophenyl)-6-oxo-6H-pyridazin-1-ylmethyl]phenyl}carbamate |
| "A109" | 3-Diethylaminopropyl {3-[3-(3,5-difluorophenyl)-6-oxo-6H-pyridazin-1-ylmethyl]phenyl}carbamate |
| "A110" | 4-Dimethylaminobutyl {3-[3-(3,5-difluorophenyl)-6-oxo-6H-pyridazin-1-ylmethyl]phenyl}carbamate |
| "A111" | 3-(2-Methoxyethoxy)propyl {3-[3-(3,4-difluorophenyl)-6-oxo-6H-pyridazin-1-ylmethyl]phenyl}carbamate |

| No. | Structure and/or name |
|---|---|
| "A112" | 4-Dimethylaminobutyl {3-[3-(3,4-difluorophenyl)-6-oxo-6H-pyridazin-1-ylmethyl]phenyl}carbamate |
| "A113" | 2-(4-Methylpiperazin-1-yl)ethyl {3-[6-oxo-3-(3,4,5-trifluoro-phenyl)-6H-pyridazin-1-ylmethyl]phenyl}carbamate |
| "A114" | 2-(3-Aminobenzyl)-6-(3,5-difluorophenyl)-2H-pyridazin-3-one |
| "A115" | 2-(3-Aminobenzyl)-6-(3,4-difluorophenyl)-2H-pyridazin-3-one |
| "A116" | 2-(3-Aminobenzyl)-6-(3,4,5-trifluorophenyl)-2H-pyridazin-3-one |
| "A117" | 2-(3-Aminobenzyl)-6-(4-fluorophenyl)-2H-pyridazin-3-one |
| "A118" | 3-[1-(3-Aminobenzyl)-6-oxo-1,6-dihydropyridazin-3-yl]-benzonitrile |
| "A119" | 2-Hydroxyethyl {3-[3-(3,5-difluorophenyl)-6-oxo-6H-pyridazin-1-ylmethyl]phenyl}carbamate |
| "A120" | 2-Hydroxyethyl {3-[3-(3,4-difluorophenyl)-6-oxo-6H-pyridazin-1-ylmethyl]phenyl}carbamate |
| "A121" | 3-[3-(3,5-Difluorophenyl)-6-oxo-6H-pyridazin-1-ylmethyl]benzoic acid |
| "A122" | 6-(3,5-Difluorophenyl)-2-[3-(5-methyloxazol-2-yl)benzyl]-2H-pyridazin-3-one |
| "A123" | 6-(3,5-Difluorophenyl)-2-[3-(5-oxo-4,5-dihydro-1,3,4-oxadiazol-2-yl)benzyl]-2H-pyridazin-3-one |
| "A124" | 2-Benzo-1,2,5-thiadiazol-5-ylmethyl-6-(3-fluorophenyl)-2H-pyridazin-3-one |
| "A125" | 2-(2-Amino-1H-benzimidazol-5-ylmethyl)-6-(3-fluorophenyl)-2H-pyridazin-3-one |
| "A126" | 2-(1H-Benzimidazol-5-ylmethyl)-6-(3-fluorophenyl)-2H-pyridazin-3-one |
| "A127" | 5-[3-(3-Fluorophenyl)-6-oxo-6H-pyridazin-1-ylmethyl]-1,3-dihydrobenzimidazol-2-one |
| "A128" | 6-(3,5-Difluorophenyl)-2-(3-hydroxybenzyl)-2H-pyridazin-3-one |
| "A129" | 1-{3-[3-(3,5-Difluorophenyl)-6-oxo-6H-pyridazin-1-ylmethyl]-phenyl}-3-(morpholin-4-ylpropyl)urea |
| "A130" | 1-{3-[3-(4-Fluorophenyl)-6-oxo-6H-pyridazin-1-ylmethyl]-phenyl}-3-(1-methylpyrrolidin-3-ylmethyl)urea |
| "A131" | 1-{3-[3-(3,5-Difluorophenyl)-6-oxo-6H-pyridazin-1-ylmethyl]-phenyl}-3-(3-pyrrolidin-1-ylpropyl)urea |
| "A132" | 1-{3-[3-(3,4-Difluorophenyl)-6-oxo-6H-pyridazin-1-ylmethyl]-phenyl}-3-(3-pyrrolidin-1-ylpropyl)urea |
| "A133" | 3-[3-(3,5-Difluorophenyl)-6-oxo-6H-pyridazin-1-ylmethyl]phenyl (3-dimethylaminopropyl)carbamate |
| "A134" | 1-{3-[3-(3,5-Difluorophenyl)-6-oxo-6H-pyridazin-1-ylmethyl]-phenyl}-3-(3-dimethylaminopropyl)urea |

| No. | Structure and/or name |
|---|---|
| "A135" | 1-{3-[3-(3,5-Difluorophenyl)-6-oxo-6H-pyridazin-1-ylmethyl]-phenyl}-3-(2-morpholin-4-ylethyl)urea |
| "A136" | 1-{3-[3-(3,5-Difluorophenyl)-6-oxo-6H-pyridazin-1-ylmethyl]-phenyl}-3-[3-(4-methylpiperazin-1-yl)propyl]urea |
| "A137" | 1-{3-[3-(3,4-Difluorophenyl)-6-oxo-6H-pyridazin-1-ylmethyl]-phenyl}-3-(3-dimethylaminopropyl)urea |
| "A138" | 1-{3-[3-(3,4-Difluorophenyl)-6-oxo-6H-pyridazin-1-ylmethyl]-phenyl}-3-(3-morpholin-4-ylpropyl)urea |
| "A139" | 1-{3-[3-(3,4-Difluorophenyl)-6-oxo-6H-pyridazin-1-ylmethyl]-phenyl}-3-(2-morpholin-4-ylethyl)urea |
| "A140" | 1-{3-[3-(3,4-Difluorophenyl)-6-oxo-6H-pyridazin-1-ylmethyl]-phenyl}-3-[3-(4-methylpiperazin-1-yl)propyl]urea |
| "A141" | {3-[3-(3,5-Difluorophenyl)-6-oxo-6H-pyridazin-1-ylmethyl]-phenyl}urea |
| "A142" | 3-Methylaminopropyl {3-[3-(3,5-difluorophenyl)-6-oxo-6H-pyridazin-1-ylmethyl]phenyl}carbamate |
| "A143" | 2-Piperazin-1-ylethyl {3-[3-(3,5-difluorophenyl)-6-oxo-6H-pyridazin-1-ylmethyl]phenyl}carbamate |
| "A144" | 3-Piperazin-1-ylpropyl {3-[3-(3,4-difluorophenyl)-6-oxo-6H-pyridazin-1-ylmethyl]phenyl}carbamate |
| "A145" | 3-Piperazin-1-ylpropyl {3-[3-(3,5-difluorophenyl)-6-oxo-6H-pyridazin-1-ylmethyl]phenyl}carbamate |
| "A146" | 2-Piperazin-1-ylethyl {3-[3-(3,4-difluorophenyl)-6-oxo-6H-pyridazin-1-ylmethyl]phenyl}carbamate |
| "A147" | 3-Methylaminopropyl {3-[3-(3,4-difluorophenyl)-6-oxo-6H-pyridazin-1-ylmethyl]phenyl}carbamate |
| "A148" | 2-Isopropylaminoethyl {3-[3-(3,4-difluorophenyl)-6-oxo-6H-pyridazin-1-ylmethyl]phenyl}carbamate |

-continued

| No. | Structure and/or name |
|---|---|
| "A149" | 3-Isopropylaminopropyl {3-[3-(3,4-difluorophenyl)-6-oxo-6H-pyridazin-1-ylmethyl]phenyl}carbamate |
| "A150" | 3-Isopropylaminopropyl {3-[3-(3,5-difluorophenyl)-6-oxo-6H-pyridazin-1-ylmethyl]phenyl}carbamate |
| "A151" | 2-Methylaminoethyl {3-[3-(3,4-difluorophenyl)-6-oxo-6H-pyridazin-1-ylmethyl]phenyl}carbamate |
| "A152" | 2-Methylaminoethyl {3-[3-(3,5-difluorophenyl)-6-oxo-6H-pyridazin-1-ylmethyl]phenyl}carbamate |
| "A153" | 2-Isopropylaminoethyl {3-[3-(3,5-difluorophenyl)-6-oxo-6H-pyridazin-1-ylmethyl]phenyl}carbamate |
| "A154" | 3-Methylaminopropyl {3-[3-(4-cyanophenyl)-6-oxo-6H-pyridazin-1-ylmethyl]phenyl}carbamate |

-continued

| No. | Structure and/or name |
|---|---|
| "A155" | 4-Methylaminobutyl {3-[3-(3,5-difluorophenyl)-6-oxo-6H-pyridazin-1-ylmethyl]phenyl}carbamate |
| "A156" | Piperidin-4-ylmethyl {3-[3-(3,5-difluorophenyl)-6-oxo-6H-pyridazin-1-ylmethyl]phenyl}carbamate |
| "A157" | Piperidin-3-ylmethyl {3-[3-(3,5-difluorophenyl)-6-oxo-6H-pyridazin-1-ylmethyl]phenyl}carbamate |
| "A158" | 6-[3-(3,5-Difluorophenyl)-6-oxo-6H-pyridazin-1-ylmethyl]-1-(3-dimethylaminopropyl)-1,3-dihydrobenzimidazol-2-one |
| "A159" | 6-[3-(3,5-Difluorophenyl)-6-oxo-6H-pyridazin-1-ylmethyl]-1-(2-dimethylaminoethyl)-1,3-dihydrobenzimidazol-2-one |
| "A160" | 6-[3-(3,5-Difluorophenyl)-6-oxo-6H-pyridazin-1-ylmethyl]-1-(4-dimethylaminobutyl)-1,3-dihydrobenzimidazol-2-one |
| "A161" | 6-(3,5-Difluorophenyl)-2-(1H-indazol-5-ylmethyl)-2H-pyridazin-3-one |
| "A162" | 4-[1-(1H-Indazol-5-ylmethyl)-6-oxo-1,6-dihydropyridazin-3-yl]-benzonitrile |
| "A163" | 6-(3,5-Difluorophenyl)-2-(1-oxyquinolin-6-ylmethyl)-2H-pyridazin-3-one |

| No. | Structure and/or name |
|---|---|
| "A164" | 6-[3-(3,5-Difluorophenyl)-6-oxo-6H-pyridazin-1-ylmethyl]-1H-quinolin-2-one |
| "A165" | 2-(3-Amino-1H-indazol-5-ylmethyl)-6-(3,5-difluorophenyl)-2H-pyridazin-3-one |
| "A166" | 3-(4-Methylpiperazin-1-yl)propyl {3-[3-(3-carbamoylphenyl)-6-oxo-6H-pyridazin-1-ylmethyl]phenyl}carbamate |
| "A167" | [structure] |
| "A168" | [structure] |
| "A169" | 5-[3-(3,5-Difluorophenyl)-6-oxo-6H-pyridazin-1-ylmethyl]-1,3-dihydrobenzimidazol-2-one [structure] | and pharmaceutically usable salts, tautomers and stereoisomers thereof, including mixtures thereof in all ratios.

2. A compound according to claim 1, selected from the following compounds:

| Structure and/or name |
|---|
| 1-(3-{3-[3-(2-Dimethylaminoethoxy)phenyl]-6-oxo-6H-pyridazin-1-ylmethyl}phenyl)-3-ethylurea, hydrochloride |
| 3-Dimethylaminopropyl {3-[3-(3,5-difluorophenyl)-6-oxo-6H-pyridazin-1-ylmethyl]phenyl}carbamate, hydrochloride |
| 3-Dimethylaminopropyl [3-(6-oxo-3-thiazol-2-yl-6H-pyridazin-1-ylmethyl)phenyl]carbamate, hydrochloride |
| 3-Dimethylaminopropyl (3-{1-[3-(3,5-difluorophenyl)-6-oxo-6H-pyridazin-1-yl]ethyl}phenyl)carbamate, hydrochloride |
| 3-Dimethylaminopropyl {3-[3-(3,4-difluorophenyl)-6-oxo-6H-pyridazin-1-ylmethyl]phenyl}carbamate, hydrochloride |
| 3-Dimethylaminopropyl {3-[3-(3,4,5-trifluorophenyl)-6-oxo-6H-pyridazin-1-ylmethyl]phenyl}carbamate, hydrochloride |
| 3-Dimethylaminopropyl {3-[3-(3-cyanophenyl)-6-oxo-6H-pyridazin-1-ylmethyl]phenyl}carbamate, hydrochloride |
| 3-Dimethylaminopropyl {3-[3-(2,3-difluorophenyl)-6-oxo-6H-pyridazin-1-ylmethyl]phenyl}carbamate, hydrochloride |
| 3-Dimethylaminopropyl {3-[3-(2,4-difluorophenyl)-6-oxo-6H-pyridazin-1-ylmethyl]phenyl}carbamate, hydrochloride |
| 3-Dimethylaminopropyl {3-[3-(3,5-dichlorophenyl)-6-oxo-6H-pyridazin-1-ylmethyl]phenyl}carbamate, hydrochloride |
| 3-Dimethylaminopropyl [3-(6-oxo-3-pyridin-3-yl-6H-pyridazin-1-ylmethyl)phenyl]carbamate, formate |
| 3-Dimethylaminopropyl {3-[3-(4-cyanophenyl)-6-oxo-6H-pyridazin-1-ylmethyl]phenyl}carbamate, hydrochloride |
| 3-Morpholin-4-ylpropyl {3-[3-(3,5-difluorophenyl)-6-oxo-6H-pyridazin-1-ylmethyl]phenyl}carbamate, hydrochloride |
| 3-Morpholin-4-ylpropyl {3-[3-(3,4-difluorophenyl)-6-oxo-6H-pyridazin-1-ylmethyl]phenyl}carbamate, hydrochloride |
| 3-Morpholin-4-ylpropyl {3-[3-(4-fluorophenyl)-6-oxo-6H-pyridazin-1-ylmethyl]phenyl}carbamate, hydrochloride |
| 3-Morpholin-4-ylpropyl [3-(6-oxo-3-thiazol-2-yl-6H-pyridazin-1-ylmethyl)phenyl]carbamate, hydrochloride |
| 3-Morpholin-4-ylpropyl [3-(6-oxo-3-thiophen-2-yl-6H-pyridazin-1-ylmethyl)phenyl]carbamate, hydrochloride |
| 3-Morpholin-4-ylpropyl (3-{1-[3-(3,5-difluorophenyl)-6-oxo-6H-pyridazin-1-yl]ethyl}phenyl)carbamate, hydrochloride |
| 3-Pyrrolidin-1-ylpropyl {3-[3-(3,4-difluorophenyl)-6-oxo-6H-pyridazin-1-ylmethyl]phenyl}carbamate, hydrochloride |
| 2-Pyrrolidin-1-ylethyl {3-[3-(3,4-difluorophenyl)-6-oxo-6H-pyridazin-1-ylmethyl]phenyl}carbamate, hydrochloride |
| 3-Pyrrolidin-1-ylpropyl {3-[3-(3,5-difluorophenyl)-6-oxo-6H-pyridazin-1-ylmethyl]phenyl}carbamate, hydrochloride |
| 2-Morpholin-4-ylethyl {3-[3-(3,5-difluorophenyl)-6-oxo-6H-pyridazin-1-ylmethyl]phenyl}carbamate, hydrochloride |
| 3-Morpholin-4-ylpropyl {3-[6-oxo-3-(3,4,5-trifluorophenyl)-6H-pyridazin-1-ylmethyl]phenyl}carbamate, hydrochloride |
| 3-Pyrrolidin-1-ylpropyl {3-[6-oxo-3-(3,4,5-trifluorophenyl)-6H-pyridazin-1-ylmethyl]phenyl}carbamate, hydrochloride |
| 2-Dimethylaminoethyl {3-[3-(3,5-difluorophenyl)-6-oxo-6H-pyridazin-1-ylmethyl]phenyl}carbamate, hydrochloride |
| 2-Morpholin-4-ylethyl {3-[3-(3,4-difluorophenyl)-6-oxo-6H-pyridazin-1-ylmethyl]phenyl}carbamate, formate |
| 2-Dimethylaminoethyl {3-[3-(3,4-difluorophenyl)-6-oxo-6H-pyridazin-1-ylmethyl]phenyl}carbamate, hydrochloride |
| 2-Pyrrolidin-1-ylethyl {3-[3-(3,5-difluorophenyl)-6-oxo-6H-pyridazin-1-ylmethyl]phenyl}carbamate, hydrochloride |
| 3-Morpholin-4-ylpropyl {3-[3-(2,4-difluorophenyl)-6-oxo-6H-pyridazin-1-ylmethyl]phenyl}carbamate, hydrochloride |
| 3-Morpholin-4-ylpropyl {3-[3-(2,3-difluorophenyl)-6-oxo-6H-pyridazin-1-ylmethyl]phenyl}carbamate, hydrochloride |
| 3-Morpholin-4-ylpropyl {3-[3-(3-cyanophenyl)-6-oxo-6H-pyridazin-1-ylmethyl]phenyl}carbamate, hydrochloride |
| 2-Morpholin-4-ylethyl {3-[3-(3,4-difluorophenyl)-6-oxo-6H-pyridazin-1-ylmethyl]phenyl}carbamate, hydrochloride |
| 3-(4-Methylpiperazin-1-yl)propyl {3-[3-(3,4-difluorophenyl)-6-oxo-6H-pyridazin-1-ylmethyl]phenyl}carbamate, dihydrochloride |
| 3-(4-Methylpiperazin-1-yl)propyl {3-[3-(3,5-difluorophenyl)-6-oxo-6H-pyridazin-1-ylmethyl]phenyl}carbamate, dihydrochloride, hydrochloride |
| 2-(4-Methylpiperazin-1-yl)ethyl {3-[3-(3,4-difluorophenyl)-6-oxo-6H-pyridazin-1-ylmethyl]phenyl}carbamate, dihydrochloride |
| 2-(4-Methylpiperazin-1-yl)ethyl {3-[3-(3,5-difluorophenyl)-6-oxo-6H-pyridazin-1-ylmethyl]phenyl}carbamate, dihydrochloride |
| 2-Morpholin-4-ylethyl }3-[6-oxo-3-(3,4,5-trifluorophenyl)-6H-pyridazin-1-ylmethyl]phenyl}carbamate, hydrochloride |
| 3-Morpholin-4-ylpropyl {3-[3-(3,5-dichlorophenyl)-6-oxo-6H-pyridazin-1-ylmethyl]phenyl}carbamate, hydrochloride |
| 1-Methylpiperidin-4-yl {3-[3-(3,5-difluorophenyl)-6-oxo-6H-pyridazin-1-ylmethyl]phenyl}carbamate, hydrochloride |
| 1-Methylpiperidin-4-yl {3-[3-(3,4-difluorophenyl)-6-oxo-6H-pyridazin-1-ylmethyl]phenyl}carbamate, hydrochloride |
| 2-Morpholin-4-ylethyl {3-[3-(4-cyanophenyl)-6-oxo-6H-pyridazin-1-ylmethyl]phenyl}carbamate, hydrochloride |
| 3-(4-Methylpiperazin-1-yl)propyl {3-[6-oxo-3-(3,4,5-trifluorophenyl)-6H-pyridazin-1-ylmethyl]phenyl}carbamate, dihydrochloride, hydrochloride |
| 4-(4-Methylpiperazin-1-yl)butyl {3-[3-(3,5-difluorophenyl)-6-oxo-6H-pyridazin-1-ylmethyl]phenyl}carbamate, dihydrochloride |
| 1-Methylpiperidin-4-ylmethyl {3-[3-(3,5-difluorophenyl)-6-oxo-6H-pyridazin-1-ylmethyl]phenyl}carbamate, hydrochloride |
| 2-(1-Methylpyrrolidin-2-yl)ethyl {3-[3-(3,5-difluorophenyl)-6-oxo-6H-pyridazin-1-ylmethyl]phenyl}carbamate, hydrochloride |
| 1-Methylpiperidin-3-ylmethyl {3-[3-(3,5-difluorophenyl)-6-oxo-6H-pyridazin-1-ylmethyl]phenyl}carbamate, hydrochloride |
| 3-(4-Methylpiperazin-1-yl)propyl }3-[3-(3-cyanophenyl)-6-oxo-6H-pyridazin-1-ylmethyl]phenyl}carbamate, dihydrochloride |
| 3-Diethylaminopropyl {3-[3-(3,5-difluorophenyl)-6-oxo-6H-pyridazin-1-ylmethyl]phenyl}carbamate, hydrochloride |
| 4-Dimethylaminobutyl {3-[3-(3,5-difluorophenyl)-6-oxo-6H-pyridazin-1-ylmethyl]phenyl}carbamate, hydrochloride |
| 4-Dimethylaminobutyl {3-[3-(3,4-difluorophenyl)-6-oxo-6H-pyridazin-1-ylmethyl]phenyl}carbamate, hydrochloride |
| 2-(4-Methylpiperazin-1-yl)ethyl {3-[6-oxo-3-(3,4,5-trifluorophenyl)-6H-pyridazin-1-ylmethyl]phenyl}carbamate, dihydrochloride |
| 1-{3-[3-(4-Fluorophenyl)-6-oxo-6H-pyridazin-1-ylmethyl]phenyl}-3-(1-methylpyrrolidin-3-ylmethyl)urea, hydrochloride |

| Structure and/or name |
|---|
| 1-{3-[3-(3,5-Difluorophenyl)-6-oxo-6H-pyridazin-1-ylmethyl]-phenyl}-3-(3-pyrrolidin-1-ylpropyl)urea, hydrochloride |
| 1-{3-[3-(3,4-Difluorophenyl)-6-oxo-6H-pyridazin-1-ylmethyl]-phenyl}-3-(3-pyrrolidin-1-ylpropyl)urea, formate |
| 3-[3-(3,5-Difluorophenyl)-6-oxo-6H-pyridazin-1-ylmethyl]phenyl (3-dimethylaminopropyl)carbamate |
| 1-{3-[3-(3,5-Difluorophenyl)-6-oxo-6H-pyridazin-1-ylmethyl]-phenyl}-3-(3-dimethylaminopropyl)urea, hydrochloride |
| 1-{3-[3-(3,5-Difluorophenyl)-6-oxo-6H-pyridazin-1-ylmethyl]-phenyl}-3-(2-morpholin-4-ylethyl)urea, hydrochloride |
| 1-{3-[3-(3,5-Difluorophenyl)-6-oxo-6H-pyridazin-1-ylmethyl]-phenyl}-3-[3-(4-methylpiperazin-1-yl)propyl]urea, hydrochloride |
| 1-{3-[3-(3,4-Difluorophenyl)-6-oxo-6H-pyridazin-1-ylmethyl]-phenyl}-3-(3-dimethylaminopropyl)urea, hydrochloride |
| 1-{3-[3-(3,4-Difluorophenyl)-6-oxo-6H-pyridazin-1-ylmethyl]-phenyl}-3-(3-morpholin-4-ylpropyl)urea, hydrochloride |
| 1-{3-[3-(3,4-Difluorophenyl)-6-oxo-6H-pyridazin-1-ylmethyl]-phenyl}-3-(2-morpholin-4-ylethyl)urea, hydrochloride |
| 1-{3-[3-(3,4-Difluorophenyl)-6-oxo-6H-pyridazin-1-ylmethyl]-phenyl}-3-[3-(4-methylpiperazin-1-yl)propyl]urea, dihydrochloride |
| 2-Piperazin-1-ylethyl {3-[3-(3,5-difluorophenyl)-6-oxo-6H-pyridazin-1-ylmethyl]phenyl}carbamate, dihydrochloride |
| 3-Piperazin-1-ylpropyl {3-[3-(3,4-difluorophenyl)-6-oxo-6H-pyridazin-1-ylmethyl]phenyl}carbamate, dihydrochloride |
| 3-Piperazin-1-ylpropyl {3-[3-(3,5-difluorophenyl)-6-oxo-6H-pyridazin-1-ylmethyl]phenyl}carbamate, dihydrochloride |
| 2-Piperazin-1-ylethyl {3-[3-(3,4-difluorophenyl)-6-oxo-6H-pyridazin-1-ylmethyl]phenyl}carbamate, dihydrochloride |
| 3-Methylaminopropyl {3-[3-(3,4-difluorophenyl)-6-oxo-6H-pyridazin-1-ylmethyl]phenyl}carbamate, hydrochloride |
| 2-Isopropylaminoethyl {3-[3-(3,4-difluorophenyl)-6-oxo-6H-pyridazin-1-ylmethyl]phenyl}carbamate, hydrochloride |
| 3-Isopropylaminopropyl {3-[3-(3,4-difluorophenyl)-6-oxo-6H-pyridazin-1-ylmethyl]phenyl}carbamate, hydrochloride |
| 3-Isopropylaminopropyl {3-[3-(3,5-difluorophenyl)-6-oxo-6H-pyridazin-1-ylmethyl]phenyl}carbamate, hydrochloride |
| 2-Methylaminoethyl {3-[3-(3,4-difluorophenyl)-6-oxo-6H-pyridazin-1-ylmethyl]phenyl}carbamate, hydrochloride |
| 2-Methylaminoethyl {3-[3-(3,5-difluorophenyl)-6-oxo-6H-pyridazin-1-ylmethyl]phenyl}carbamate, hydrochloride |
| 2-Isopropylaminoethyl {3-[3-(3,5-difluorophenyl)-6-oxo-6H-pyridazin-1-ylmethyl]phenyl}carbamate, hydrochloride |
| 3-Methylaminopropyl {3-[3-(4-cyanophenyl)-6-oxo-6H-pyridazin-1-ylmethyl]phenyl}carbamate, hydrochloride |
| 4-Methylaminobutyl {3-[3-(3,5-difluorophenyl)-6-oxo-6H-pyridazin-1-ylmethyl]phenyl}carbamate, hydrochloride |
| Piperidin-4-ylmethyl {3-[3-(3,5-difluorophenyl)-6-oxo-6H-pyridazin-1-ylmethyl]phenyl}carbamate, hydrochloride |
| Piperidin-3-ylmethyl {3-[3-(3,5-difluorophenyl)-6-oxo-6H-pyridazin-1-ylmethyl]phenyl}carbamate, hydrochloride |
| 6-[3-(3,5-Difluorophenyl)-6-oxo-6H-pyridazin-1-ylmethyl]-1-(2-dimethylaminoethyl)-1,3-dihydrobenzimidazol-2-one, hydrochloride |
| 6-[3-(3,5-Difluorophenyl)-6-oxo-6H-pyridazin-1-ylmethyl]-1-(4-dimethylaminobutyl)-1,3-dihydrobenzimidazol-2-one, hydrochloride | and pharmaceutically usable tautomers and stereoisomers thereof, including mixtures thereof in all ratios.

3. A compound according to claim 1, selected from the following compounds:

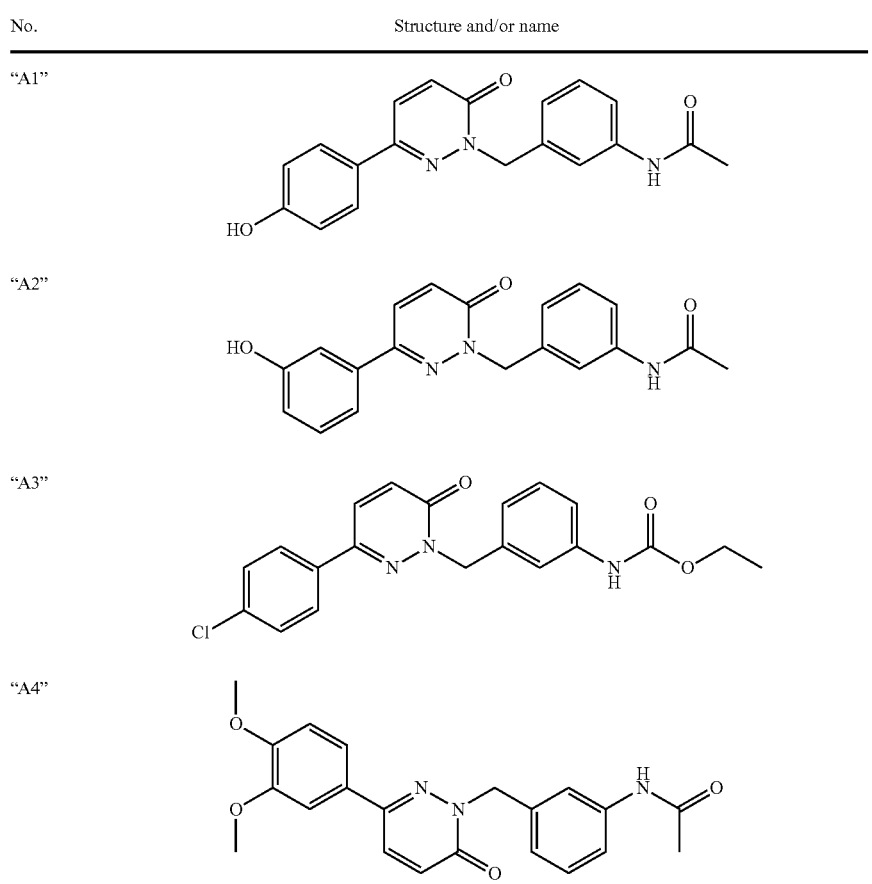

| No. | Structure and/or name |
|---|---|
| "A1" | |
| "A2" | |
| "A3" | |
| "A4" | |

-continued
| No. | Structure and/or name |
|---|---|
| "A5" | 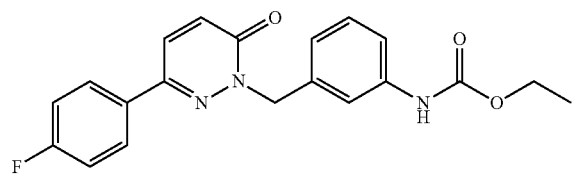 |
| "A6" | 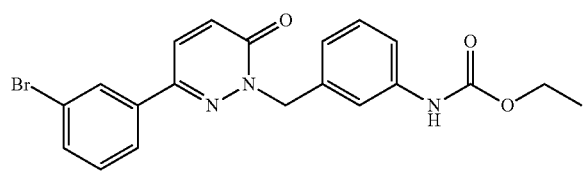 |
| "A7" | 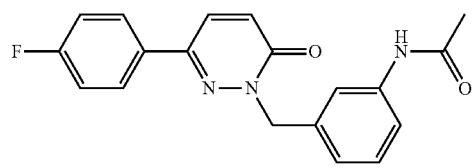 |
| "A8" | 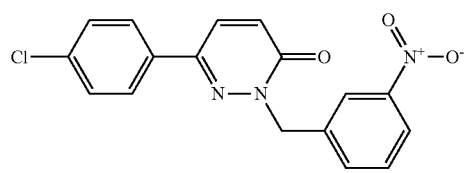 |
| "A9" | 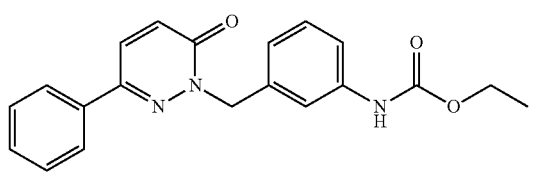 |
| "A10" | 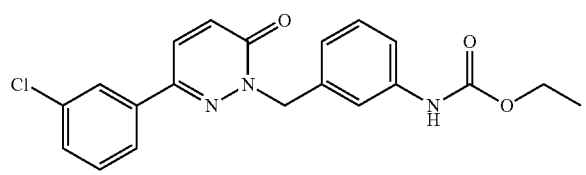 |
| "A11" | 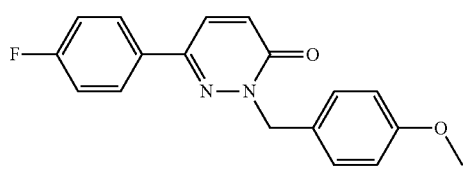 |
| "A12" | 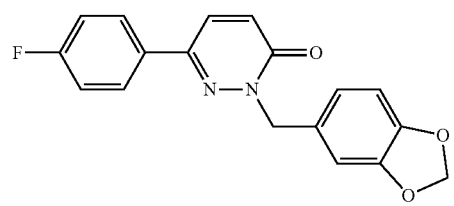 |

-continued
| No. | Structure and/or name |
|---|---|
| "A13" | 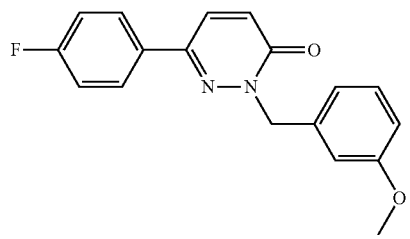 |
| "A14" | 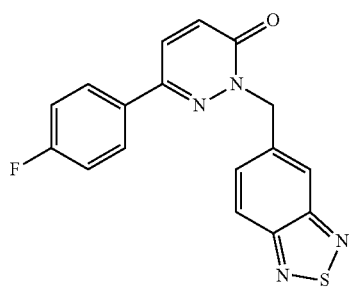 |
| "A15" | 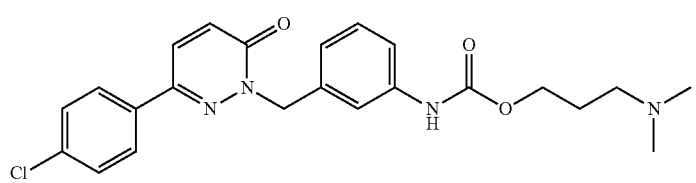 |
| "A16" | 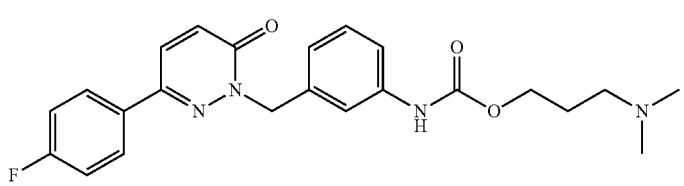 |
| "A17" | 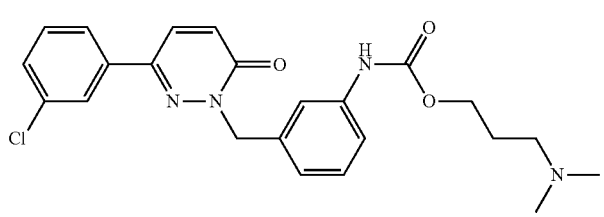 |
| "A18" | 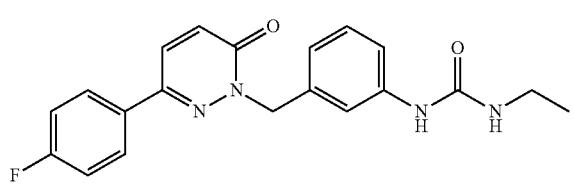 |
| "A19" | 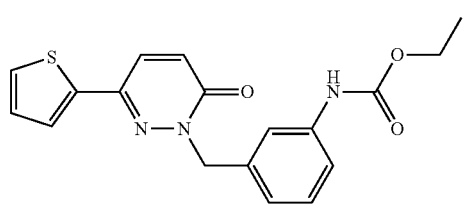 |

| No. | Structure and/or name |
|---|---|
| "A20" | 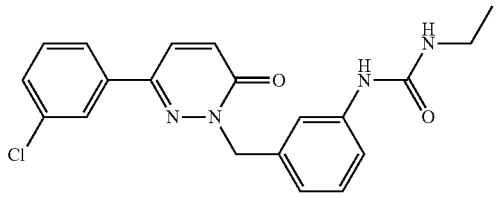 |
| "A21" | 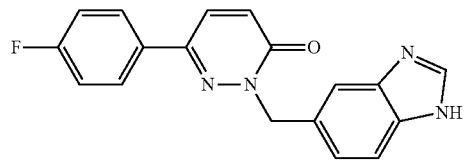 |
| "A22" | 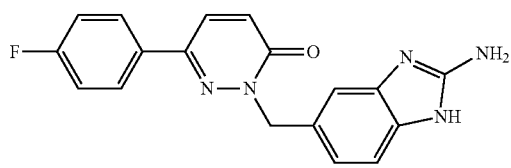 |
| "A23" | 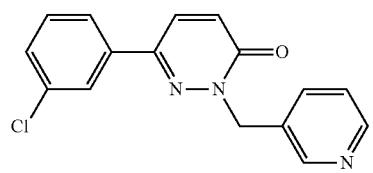 |
| "A24" | 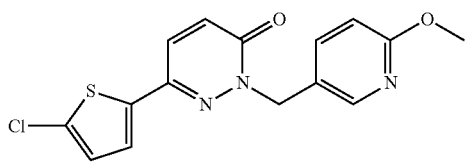 |
| "A25" | 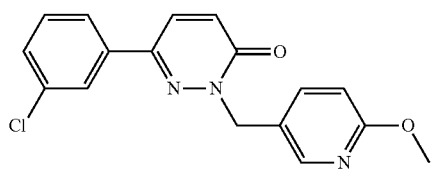 |
| "A25a" | 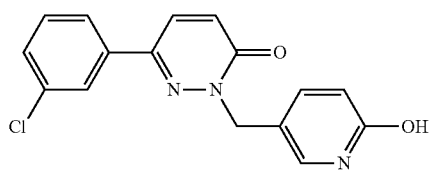 |
| "A26" | 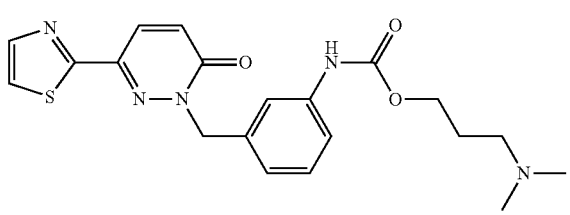 |

| No. | Structure and/or name |
|---|---|
| "A27" | 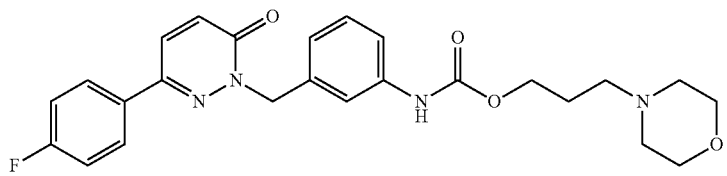 |
| "A28" | 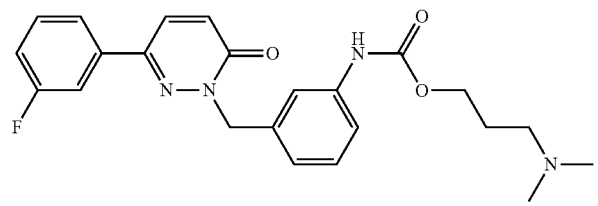 |
| "A29" | 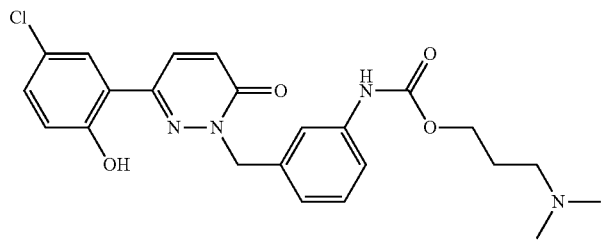 |
| "A30" | 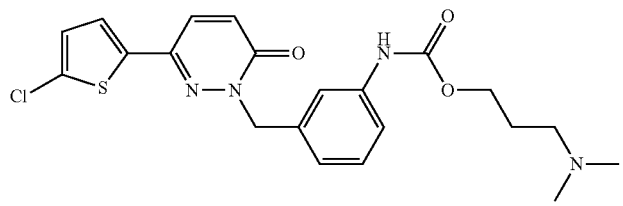 |
| "A31" | 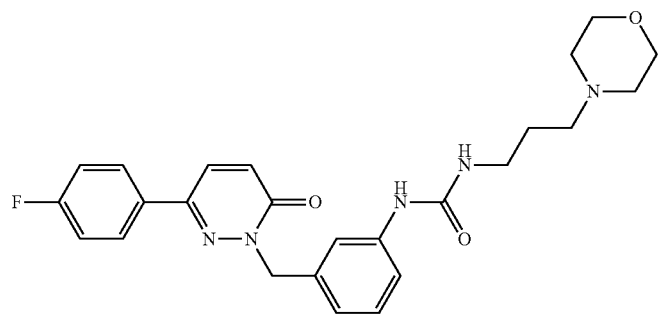 |
| "A32" | 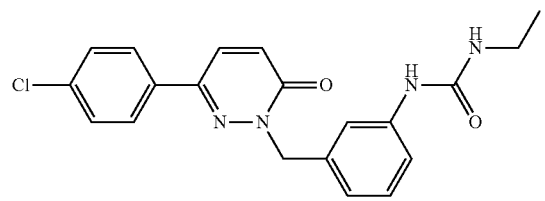 |

| No. | Structure and/or name |
|---|---|
| "A33" | 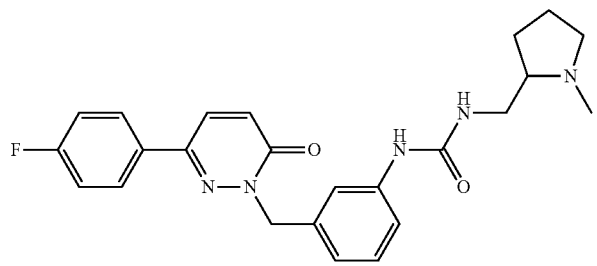 |
| "A34" | 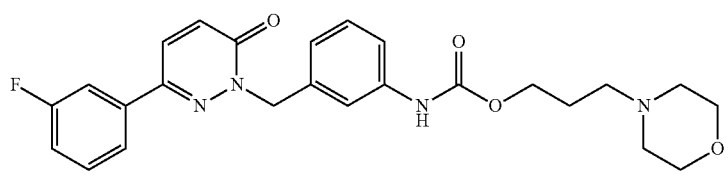 |
| "A35" | 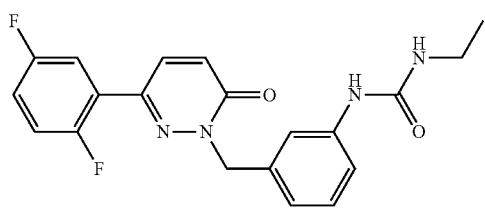 |
| "A36" | 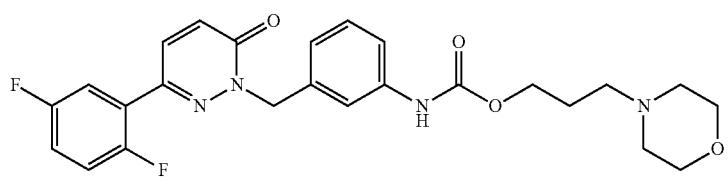 |
| "A37" | 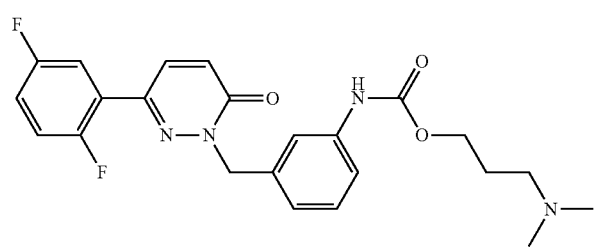 |
| "A38" | 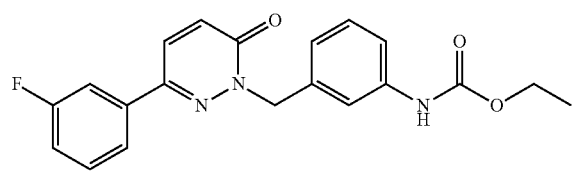 |
| "A39" | 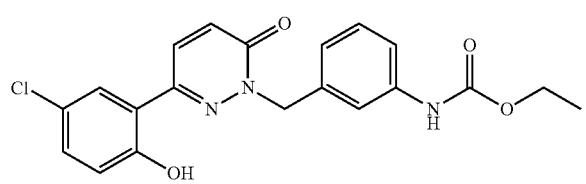 |

| No. | Structure and/or name |
|---|---|
| "A40" | [structure: 3-(3-chlorophenyl)-6-oxopyridazin-1-yl methylene linked to phenyl carbamate of 3-morpholinopropanol] |
| "A41" | [structure: 3-(3-cyanophenyl)-6-oxopyridazin-1-yl methylene linked to phenyl carbamate of 3-(dimethylamino)propanol] |
| "A42" | [structure: 3-(3-chlorophenyl)-6-oxopyridazin-1-yl methylene linked to 6-methoxypyridin-3-yl] |
| "A43" | [structure: 3-[3-(2-morpholinoethoxy)phenyl]-6-oxopyridazin-1-yl methylene linked to 3-(3-ethylureido)phenyl] |
| "A43a" | 1-Ethyl-3-{3-[3-(3-hydroxyphenyl)-6-oxo-6H-pyridazin-1-yl-methyl]phenyl}urea |
| "A44" | [structure: 3-[3-(3-morpholinopropoxy)phenyl]-6-oxopyridazin-1-yl methylene linked to 3-(3-ethylureido)phenyl] |
| "A45" | [structure: 3-(3-fluorophenyl)-6-oxopyridazin-1-yl methylene linked to 1H-benzimidazol-5-yl] |
| "A45a" | 2-(2-Amino-1H-benzimidazol-5-ylmethyl)-6-(3-fluorophenyl)-2H-pyridazin-3-one |
| "A46" | [structure: 3-(3-fluorophenyl)-6-oxopyridazin-1-yl methylene linked to 1H-benzotriazol-5-yl] |

-continued

| No. | Structure and/or name |
|---|---|
| "A47" | 2-Benzo-1,2,5-thiadiazol-5-ylmethyl-6-(3-fluorophenyl)-2H-pyridazin-3-one 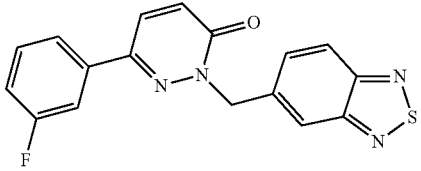 |
| "A48" | 6-(3,5-Difluorophenyl)-2-pyridin-3-ylmethyl-2H-pyridazin-3-one 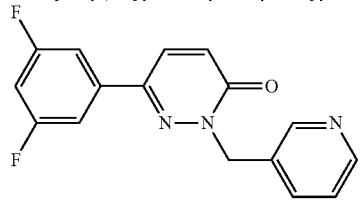 |
| "A49" | 6-(3,5-Difluorophenyl)-2-(3-cyanobenzyl)-2H-pyridazin-3-one 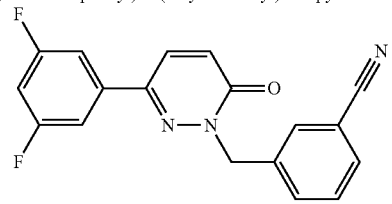 |
| "A50" | 6-(3,5-Difluorophenyl)-2-(3-methoxycarbonylbenzyl)-2H-pyridazin-3-one |
| "A51" | 6-(3,5-Difluorophenyl)-2-quinolin-6-ylmethyl-2H-pyridazin-3-one 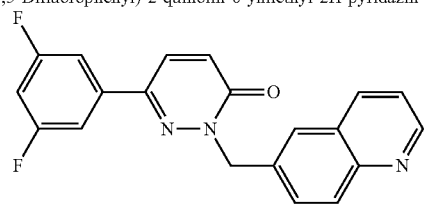 |
| "A52" | 6-(3,4-Difluorophenyl)-2-quinolin-6-ylmethyl-2H-pyridazin-3-one |
| "A53" | 6-(4-Fluorophenyl)-2-quinolin-6-ylmethyl-2H-pyridazin-3-one |
| "A54" | 6-(3,5-Difluorophenyl)-2-pyridin-4-ylmethyl-2H-pyridazin-3-one |
| "A55" | 6-(3,5-Difluorophenyl)-2-(3-acetamidobenzyl)-2H-pyridazin-3-one |
| "A60" | 3-Dimethylaminopropyl {3-[3-(3,4,5-trifluorophenyl)-6-oxo-6H-pyridazin-1-ylmethyl]phenyl}carbamate |
| "A61" | 3-Dimethylaminopropyl {3-[3-(3-cyanophenyl)-6-oxo-6H-pyridazin-1-ylmethyl]phenyl}carbamate |
| "A75" | 3-Methoxypropyl {3-[3-(3,5-difluorophenyl)-6-oxo-6H-pyridazin-1-ylmethyl]phenyl}carbamate 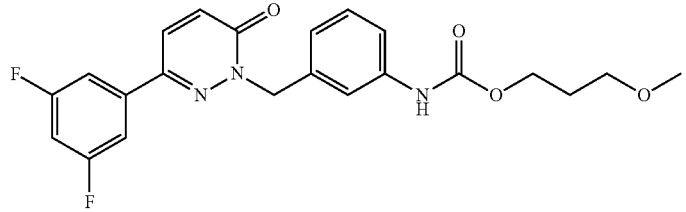 |

| No. | Structure and/or name |
|---|---|
| "A76" | 3-Methoxypropyl {3-[3-(3,4-difluorophenyl)-6-oxo-6H-pyridazin-1-ylmethyl]phenyl}carbamate |
| "A84" | 2-Methoxyethyl {3-[3-(3,5-difluorophenyl)-6-oxo-6H-pyridazin-1-ylmethyl]phenyl}carbamate |
| "A85" | 2-Methoxyethyl {3-[3-(3,4-difluorophenyl)-6-oxo-6H-pyridazin-1-ylmethyl]phenyl}carbamate |
| "A94" | 2-(2-Methoxyethoxy)ethyl {3-[3-(3,5-difluorophenyl)-6-oxo-6H-pyridazin-1-ylmethyl]phenyl}carbamate |
| "A97" | 2-(2-Methoxyethoxy)ethyl {3-[3-(3,4-difluorophenyl)-6-oxo-6H-pyridazin-1-ylmethyl]phenyl}carbamate |
| "A102" | 4-Dimethylaminobutyl {3-[3-(3,5-difluorophenyl)-6-oxo-6H-pyridazin-1-ylmethyl]phenyl}carbamate |
| "A103" | 4-(4-Methylpiperazin-1-yl)butyl {3-[3-(3,5-difluorophenyl)-6-oxo-6H-pyridazin-1-ylmethyl]phenyl}carbamate |

| No. | Structure and/or name |
|---|---|
| "A104" | 1-Methylpiperidin-4-ylmethyl {3-[3-(3,5-difluorophenyl)-6-oxo-6H-pyridazin-1-ylmethyl]phenyl}carbamate |
| "A108" | 3-(2-Methoxyethoxy)propyl {3-[3-(3,5-difluorophenyl)-6-oxo-6H-pyridazin-1-ylmethyl]phenyl}carbamate |
| "A111" | 3-(2-Methoxyethoxy)propyl {3-[3-(3,4-difluorophenyl)-6-oxo-6H-pyridazin-1-ylmethyl]phenyl}carbamate |
| "A112" | 4-Dimethylaminobutyl {3-[3-(3,4-difluorophenyl)-6-oxo-6H-pyridazin-1-ylmethyl]phenyl}carbamate |
| "A114" | 2-(3-Aminobenzyl)-6-(3,5-difluorophenyl)-2H-pyridazin-3-one |
| "A115" | 2-(3-Aminobenzyl)-6-(3,4-difluorophenyl)-2H-pyridazin-3-one |
| "A116" | 2-(3-Aminobenzyl)-6-(3,4,5-trifluorophenyl)-2H-pyridazin-3-one |
| "A117" | 2-(3-Aminobenzyl)-6-(4-fluorophenyl)-2H-pyridazin-3-one |
| "A118" | 3-[1-(3-Aminobenzyl)-6-oxo-1,6-dihydropyridazin-3-yl]-benzonitrile |

-continued

| No. | Structure and/or name |
|---|---|
| "A119" | 2-Hydroxyethyl {3-[3-(3,5-difluorophenyl)-6-oxo-6H-pyridazin-1-ylmethyl]phenyl}carbamate |
| "A120" | 2-Hydroxyethyl {3-[3-(3,4-difluorophenyl)-6-oxo-6H-pyridazin-1-ylmethyl]phenyl}carbamate |
| "A121" | 3-[3-(3,5-Difluorophenyl)-6-oxo-6H-pyridazin-1-ylmethyl]benzoic acid |
| "A122" | 6-(3,5-Difluorophenyl)-2-[3-(5-methyloxazol-2-yl)benzyl]-2H-pyridazin-3-one |
| "A123" | 6-(3,5-Difluorophenyl)-2-[3-(5-oxo-4,5-dihydro-1,3,4-oxadiazol-2-yl)benzyl]-2H-pyridazin-3-one |
| "A124" | 2-Benzo-1,2,5-thiadiazol-5-ylmethyl-6-(3-fluorophenyl)-2H-pyridazin-3-one |
| "A125" | 2-(2-Amino-1H-benzimidazol-5-ylmethyl)-6-(3-fluorophenyl)-2H-pyridazin-3-one |
| "A126" | 2-(1H-Benzimidazol-5-ylmethyl)-6-(3-fluorophenyl)-2H-pyridazin-3-one |
| "A127" | 5-[3-(3-Fluorophenyl)-6-oxo-6H-pyridazin-1-ylmethyl]-1,3-dihydrobenzimidazol-2-one |
| "A128" | 6-(3,5-Difluorophenyl)-2-(3-hydroxybenzyl)-2H-pyridazin-3-one |
| "A129" | 1-{3-[3-(3,5-Difluorophenyl)-6-oxo-6H-pyridazin-1-ylmethyl]-phenyl}-3-(3-morpholin-4-ylpropyl)urea |
| "A141" | {3-[3-(3,5-Difluorophenyl)-6-oxo-6H-pyridazin-1-ylmethyl]-phenyl}urea |
| "A142" | 3-Methylaminopropyl {3-[3-(3,5-difluorophenyl)-6-oxo-6H-pyridazin-1-ylmethyl]phenyl}carbamate |
| "A158" | 6-[3-(3,5-Difluorophenyl)-6-oxo-6H-pyridazin-1-ylmethyl]-1-(3-dimethylaminopropyl)-1,3-dihydrobenzimidazol-2-one |
| "A161" | 6-(3,5-Difluorophenyl)-2-(1H-indazol-5-ylmethyl)-2H-pyridazin-3-one |
| "A162" | 4-[1-(1H-Indazol-5-ylmethyl)-6-oxo-1,6-dihydropyridazin-3-yl]-benzonitrile |
| "A163" | 6-(3,5-Difluorophenyl)-2-(1-oxyquinolin-6-ylmethyl)-2H-pyridazin-3-one |
| "A164" | 6-[3-(3,5-Difluorophenyl)-6-oxo-6H-pyridazin-1-ylmethyl]-1H-quinoin-2-one |

| No. | Structure and/or name |
|---|---|
| "A165" | 2-(3-Amino-1H-indazol-5-ylmethyl)-6-(3,5-difluorophenyl)-2H-pyridazin-3-one |
| "A166" | 3-(4-Methylpiperazin-1-yl)propyl {3-[3-(3-carbamoylphenyl)-6-oxo-6H-pyridazin-1-ylmethyl]phenyl}carbamate |
| "A167" | [structure] |
| "A168" | [structure] |
| "A169" | 5-[3-(3,5-Difluorophenyl)-6-oxo-6H-pyridazin-1-ylmethyl]-1,3-dihydrobenzimidazol-2-one [structure] | and pharmaceutically usable salts, tautomers and stereoisomers thereof, including mixtures thereof in all ratios.

4. A compound according to claim 1, selected from the following compounds:

| No. | Structure and/or name |
|---|---|
| "A1" | [structure] |
| "A2" | [structure] |
| "A3" | [structure] |

-continued
| No. | Structure and/or name |
|---|---|
| "A4" | 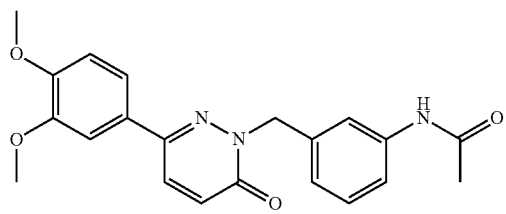 |
| "A5" | 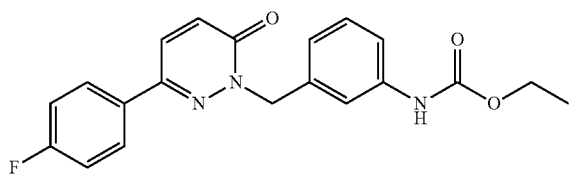 |
| "A6" | 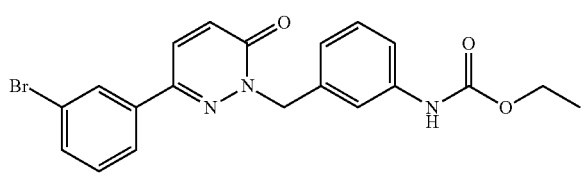 |
| "A7" | 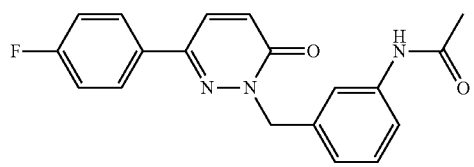 |
| "A8" | 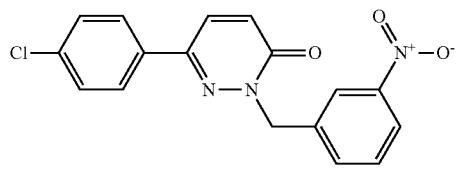 |
| "A9" | 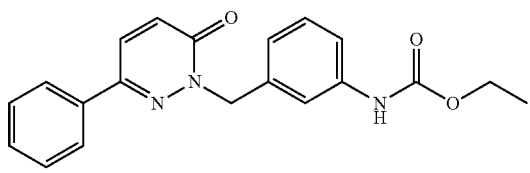 |
| "A10" | 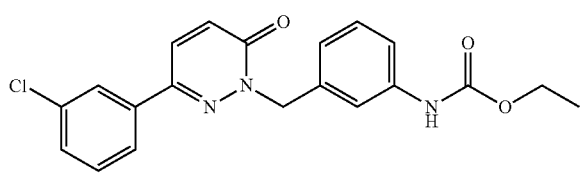 |
| "A11" | 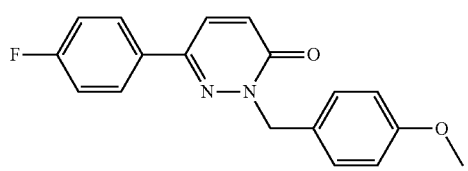 |

| No. | Structure and/or name |
|---|---|
| "A12" | 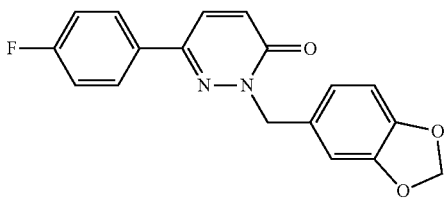 |
| "A13" | 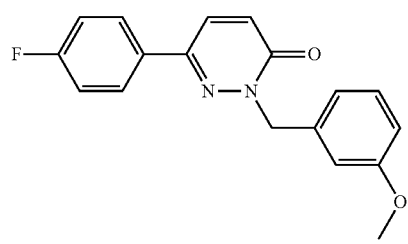 |
| "A14" | 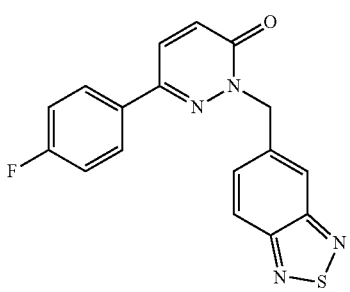 |
| "A15" | 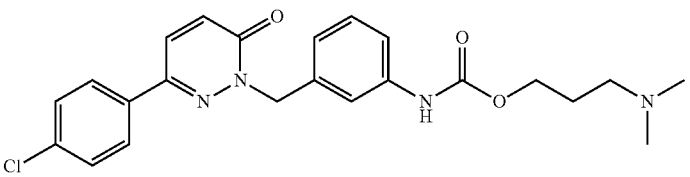 |
and pharmaceutically usable salts, tautomers and stereoisomers thereof, including mixtures thereof in all ratios.
5. A compound according to claim 1, selected from the following compounds:
| No. | Structure and/or name |
|---|---|
| "A16" | 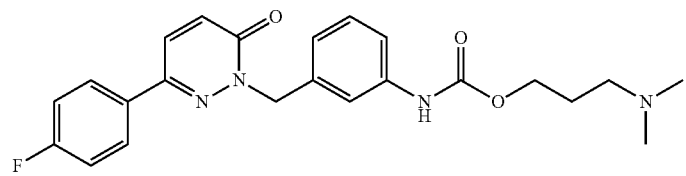 |
| "A17" | 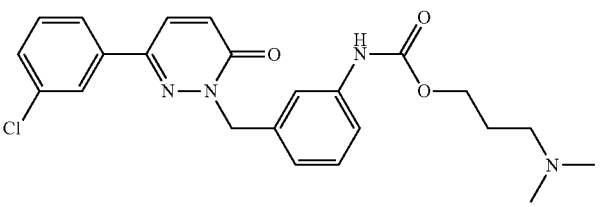 |

-continued

| No. | Structure and/or name |
|---|---|
| "A18" | 3-(4-fluorophenyl)-2-[[3-(3-ethylureido)phenyl]methyl]pyridazin-3(2H)-one |
| "A19" | ethyl [3-[[6-oxo-3-(thiophen-2-yl)pyridazin-1(6H)-yl]methyl]phenyl]carbamate |
| "A20" | 3-(3-chlorophenyl)-2-[[3-(3-ethylureido)phenyl]methyl]pyridazin-3(2H)-one |
| "A21" | 3-(4-fluorophenyl)-2-[(1H-benzimidazol-5-yl)methyl]pyridazin-3(2H)-one |
| "A22" | 2-amino-5-[[3-(4-fluorophenyl)-6-oxopyridazin-1(6H)-yl]methyl]-1H-benzimidazole |
| "A23" | 3-(3-chlorophenyl)-2-(pyridin-3-ylmethyl)pyridazin-3(2H)-one |
| "A24" | 3-(5-chlorothiophen-2-yl)-2-[(6-methoxypyridin-3-yl)methyl]pyridazin-3(2H)-one |
| "A25" | 3-(3-chlorophenyl)-2-[(6-methoxypyridin-3-yl)methyl]pyridazin-3(2H)-one |

| No. | Structure and/or name |
|---|---|
| "A25a" | 6-(3-chlorophenyl)-2-[(6-hydroxypyridin-3-yl)methyl]pyridazin-3(2H)-one |
| "A26" | carbamate of 3-{[3-oxo-6-(1,3-thiazol-2-yl)pyridazin-2(3H)-yl]methyl}phenyl with 3-(dimethylamino)propanol |
| "A27" | 3-{[6-(4-fluorophenyl)-3-oxopyridazin-2(3H)-yl]methyl}phenyl carbamate with 3-morpholinopropanol |
| "A28" | 3-{[6-(3-fluorophenyl)-3-oxopyridazin-2(3H)-yl]methyl}phenyl carbamate with 3-(dimethylamino)propanol |
| "A29" | 3-{[6-(5-chloro-2-hydroxyphenyl)-3-oxopyridazin-2(3H)-yl]methyl}phenyl carbamate with 3-(dimethylamino)propanol | and pharmaceutically usable salts, tautomers and stereoisomers thereof, including mixtures thereof in all ratios.

6. A compound according to claim 1, selected from the following compounds:

| No. | Structure and/or name |
|---|---|
| "A30" | 3-{[6-(5-chlorothiophen-2-yl)-3-oxopyridazin-2(3H)-yl]methyl}phenyl carbamate with 3-(dimethylamino)propanol |

| No. | Structure and/or name |
|---|---|
| "A31" | 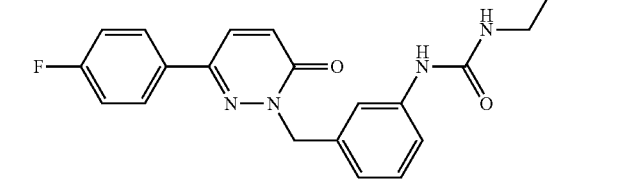 |
| "A32" | 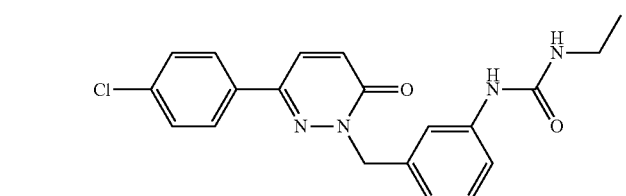 |
| "A33" | 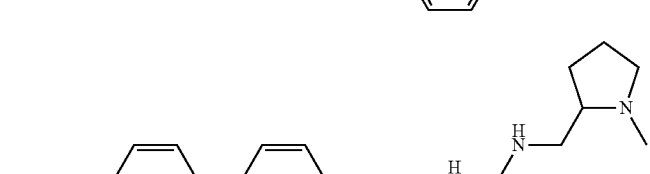 |
| "A34" | 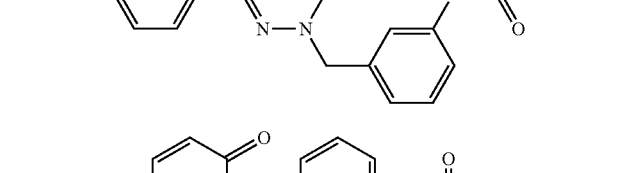 |
| "A35" | 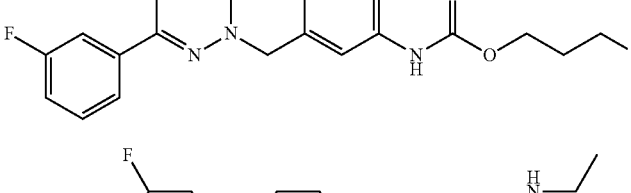 |
| "A36" | 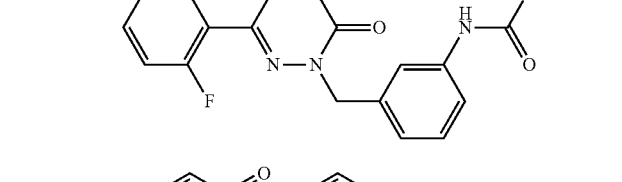 |
| "A37" | 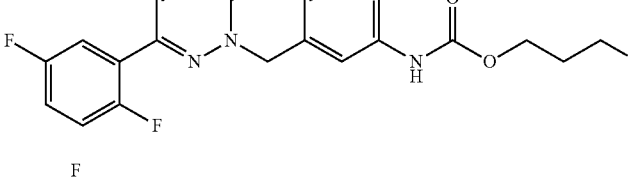 |

-continued

| No. | Structure and/or name |
|---|---|
| "A38" | [structure: 3-(3-fluorophenyl)-6-oxo-pyridazine with N-CH2-phenyl-NH-C(=O)-O-ethyl] |
| "A39" | [structure: 3-(5-chloro-2-hydroxyphenyl)-6-oxo-pyridazine with N-CH2-phenyl-NH-C(=O)-O-ethyl] |
| "A40" | [structure: 3-(3-chlorophenyl)-6-oxo-pyridazine with N-CH2-phenyl-NH-C(=O)-O-propyl-morpholine] |
| "A41" | [structure: 3-(3-cyanophenyl)-6-oxo-pyridazine with N-CH2-phenyl-NH-C(=O)-O-propyl-N(CH3)2] |
| "A42" | [structure: 3-(3-chlorophenyl)-6-oxo-pyridazine with N-CH2-(6-methoxypyridin-3-yl)] |
| "A43" | [structure: 3-[3-(2-morpholinoethoxy)phenyl]-6-oxo-pyridazine with N-CH2-phenyl-NH-C(=O)-NH-ethyl] |
| "A43a" | 1-Ethyl-3{3-[3-(3-hydroxyphenyl)-6-oxo-6H-pyridazin-1-yl-methyl]phenyl}urea | and pharmaceutically usable salts, tautomers and stereoisomers thereof, including mixtures thereof in all ratios.

7. A compound according to claim 1, selected from the following compounds:

| No. | Structure and/or name |
|---|---|
| "A43b" | 1-(3-{3-[3-(2-Dimethylaminoethoxy)phenyl]-6-oxo-6H-pyridazin-1-ylmethyl}phenyl)-3-ethylurea |
| "A44" | [structure: 3-[3-(3-morpholinopropoxy)phenyl]-6-oxo-pyridazine with N-CH2-phenyl-NH-C(=O)-NH-ethyl] |

-continued

| No. | Structure and/or name |
|---|---|
| "A45" | 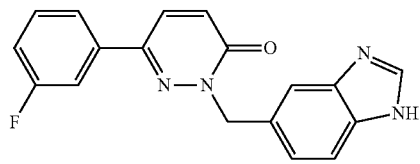 |
| "A45a" | 2-(2-Amino-1H-benzimidazol-5-ylmethyl)-6-(3-fluorophenyl)-2H-pyridazin-3-one |
| "A46" | 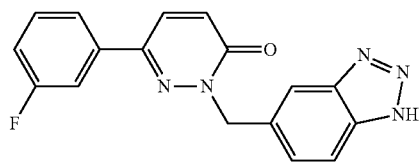 |
| "A47" | 2-Benzo-1,2,5-thiadiazol-5-ylmethyl-6-(3-fluorophenyl)-2H-pyridazin-3-one 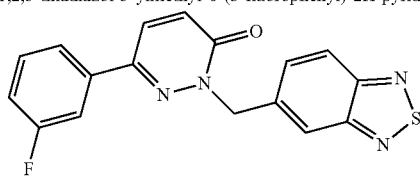 |
| "A48" | 6-(3,5-Difluorophenyl)-2-pyridin-3-ylmethyl-2H-pyridazin-3-one 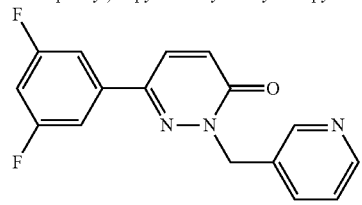 |
| "A49" | 6-(3,5-Difluorophenyl)-2-(3-cyanobenzyl)-2H-pyridazin-3-one 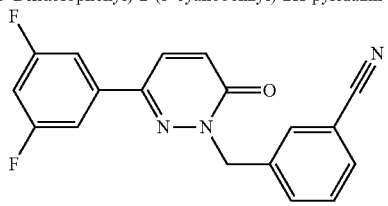 |
| "A50" | 6-(3,5-Difluorophenyl)-2-(3-methoxycarbonylbenzyl)-2H-pyridazin-3-one |
| "A51" | 6-(3,5-Difluorophenyl)-2-quinolin-6-ylmethyl-2H-pyridazin-3-one 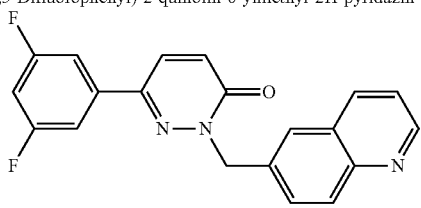 |
| "A52" | 6-(3,4-Difluorophenyl)-2-quinolin-6-ylmethyl-2H-pyridazin-3-one |
| "A53" | 6-(4-Fluorophenyl)-2-quinolin-6-ylmethyl-2H-pyridazin-3-one |
| "A54" | 6-(3,5-Difluorophenyl)-2-pyridin-4-ylmethyl-2H-pyridazin-3-one |
| "A55" | 6-(3,5-Difluorophenyl)-2-(3-acetamidobenzyl)-2H-pyridazin-3-one |

-continued

| No. | Structure and/or name |
|---|---|
| "A56" | 3-Dimethylaminopropyl{3-[3-(3,5-difluorophenyl)-6-oxo-6H-pyridazin-1-ylmethyl]phenyl}carbamate 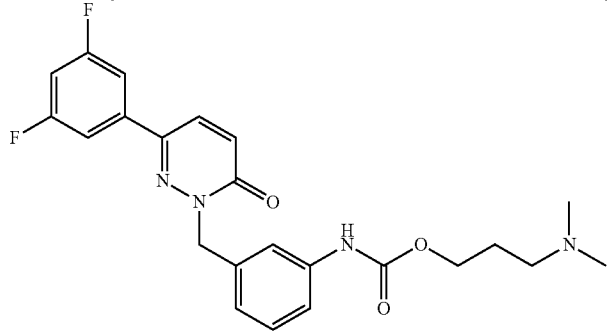 | and pharmaceutically usable salts, tautomers and stereoisomers thereof, including mixtures thereof in all ratios.

8. A compound according to claim 1, selected from the following compounds:

| No. | Structure and/or name |
|---|---|
| "A57" | 3-Dimethylaminopropyl[3-(6-oxo-3-thiazol-2-yl-6H-pyridazin-1-ylmethyl)phenyl]carbamate 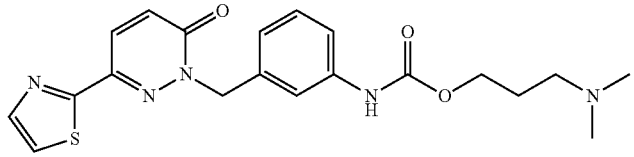 |
| "A58" | 3-Dimethylaminopropyl(3-{1-[3-(3,5-difluorophenyl)-6-oxo-6H-pyridazin-1-yl]ethyl}phenyl)carbamate 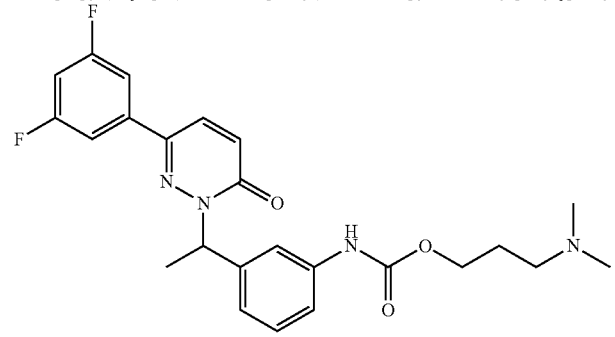 |
| "A59" | 3-Dimethylaminopropyl{3-[3-(3,4-difluorophenyl)-6-oxo-6H-pyridazin-1-ylmethyl]phenyl}carbamate |
| "A60" | 3-Dimethylaminopropyl{3-[3-(3,4,5-trifluorophenyl)-6-oxo-6H-pyridazin-1-ylmethyl]phenyl}carbamate |
| "A61" | 3-Dimethylaminopropyl{3-[3-(3-cyanophenyl)-6-oxo-6H-pyridazin-1-ylmethyl]phenyl}carbamate |
| "A62" | 3-Dimethylaminopropyl{3-[3-(2,3-difluorophenyl)-6-oxo-6H-pyridazin-1-ylmethyl]phenyl}carbamate |
| "A63" | 3-Dimethylaminopropyl{3-[3-(2,4-difluorophenyl)-6-oxo-6H-pyridazin-1-ylmethyl]phenyl}carbamate |
| "A64" | 3-Dimethylaminopropyl{3-[3-(3,5-dichlorophenyl)-6-oxo-6H-pyridazin-1-ylmethyl]phenyl}carbamate |
| "A65" | 3-Dimethylaminopropyl[3-(6-oxo-3-pyridin-3-yl-6H-pyridazin-1-ylmethyl)phenyl]carbamate 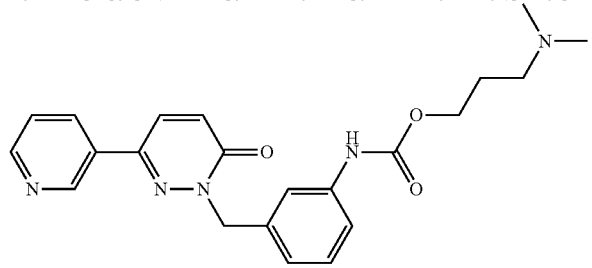 |

| No. | Structure and/or name |
|---|---|
| "A66" | 3-Dimethylaminopropyl{3-[3-(4-cyanophenyl)-6-oxo-6H-pyridazin-1-ylmethyl]phenyl}carbamate |
| "A67" | 3-Morpholin-4-ylpropyl{3-[3-(3,5-difluorophenyl)-6-oxo-6H-pyridazin-l-ylmethyl]phenyl}carbamate |
| "A68" | 3-Morpholin-4-ylpropyl{3-[3-(3,4-difluorophenyl)-6-oxo-6H-pyridazin-1-ylmethyl]phenyl}carbamate |
| "A69" | 3-Morpholin-4-ylpropyl{3-[3-(4-fluorophenyl)-6-oxo-6H-pyridazin-1-ylmethyl]phenyl}carbamate |
| "A70" | 3-Morpholin-4-ylpropyl[3-(6-oxo-3-thiazol-2-yl-6H-pyridazin-1-ylmethyl)phenyl]carbamate |
| "A71" | 3-Morpholin-4-ylpropyl[3-(6-oxo-3-thiophen-2-yl-6H-pyridazin-1-ylmethyl)phenyl]carbamate | and pharmaceutically usable salts, tautomers and stereoisomers thereof, including mixtures thereof in all ratios.

9. A compound according to claim 1, selected from the following compounds:

| No. | Structure and/or name |
|---|---|
| "A72" | 3-Morpholin-4-ylpropyl(3-{1[3-(3,5-difluorophenyl)-6-oxo-6H-pyridazin-1-yl]ethyl}phenyl)carbamate |

-continued

| No. | Structure and/or name |
|---|---|
| "A73" | 3-Pyrrolidin-1-ylpropyl{3-[3-(3,4-difluorophenyl)-6-oxo-6H-pyridazin-1-ylmethyl]phenyl}carbamate 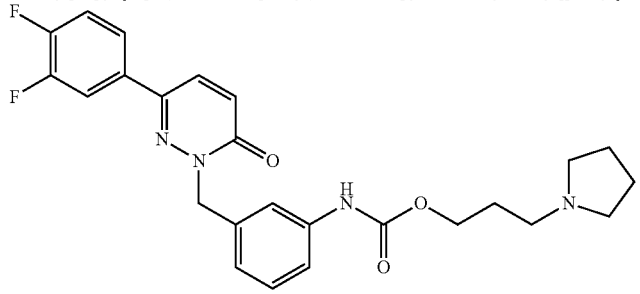 |
| "A73a" | 2-Pyrrolidin-1-ylethyl{3-[3-(3,4-difluorophenyl)-6-oxo-6H-pyridazin-1-ylmethyl]phenyl}carbamate |
| "A74" | 3-Pyrrolidin-1-ylpropyl{3-[3-(3,5-difluorophenyl)-6-oxo-6H-pyridazin-1-ylmethyl]phenyl}carbamate |
| "A75" | 3-Methoxypropyl{3-[3(3,5-difluorophenyl)-6-oxo-6H-pyridazin-1-ylmethyl]phenyl}carbamate 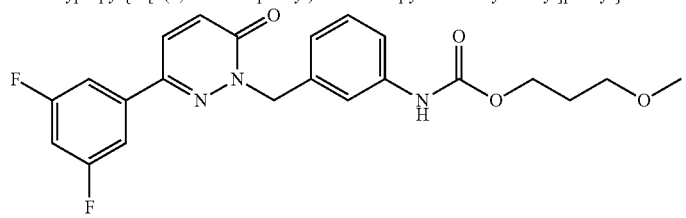 |
| "A76" | 3-Methoxypropyl{3-[3(3,4-difluorophenyl)-6-oxo-6H-pyridazin-1-ylmethyl]phenyl}carbamate |
| "A77" | 2-Morpholin-4-ylethyl{3-[3(3,5-difluorophenyl)-6-oxo-6H-pyridazin-1-ylmethyl]phenyl}carbamate |
| "A78" | 3-Morpholin-4-ylpropyl{3-[6-oxo-3-(3,4,5-trifluorophenyl)-6H-pyridazin-1-ylmethyl]phenyl}carbamate 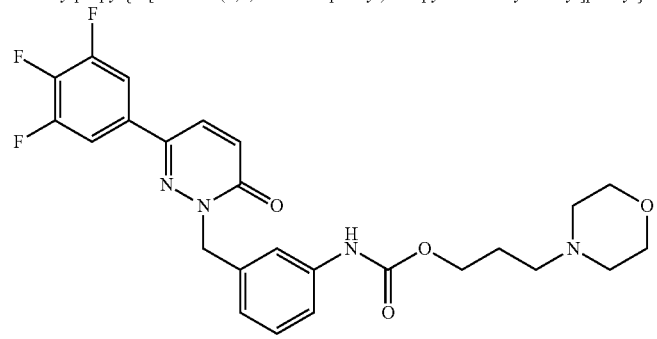 |
| "A79" | 3-Pyrrolidin-1-ylpropyl{3-[6-oxo-3-(3,4,5-trifluorophenyl)-6H-pyridazin-1-ylmethyl]phenyl}carbamate 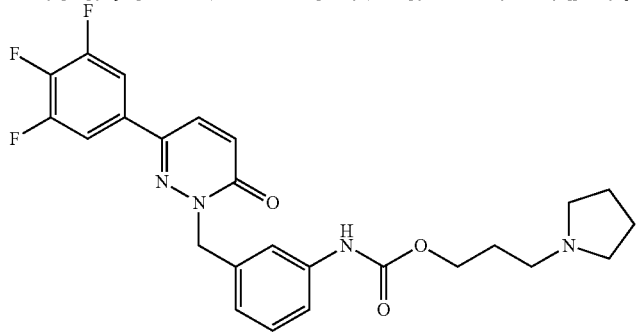 |

| No. | Structure and/or name |
|---|---|
| "A80" | 2-Dimethylaminoethyl{3-[3-(3,5-difluorophenyl)-6-oxo-6H-pyridazin-1-ylmethyl]phenyl}carbamate 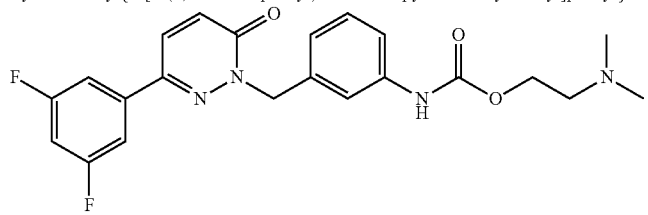 |
| "A81" | 2-Morpholin-4-ylethyl{3-[3-(3,4-difluorophenyl)-6-oxo-6H-pyridazin-1-ylmethyl]phenyl}carbamate 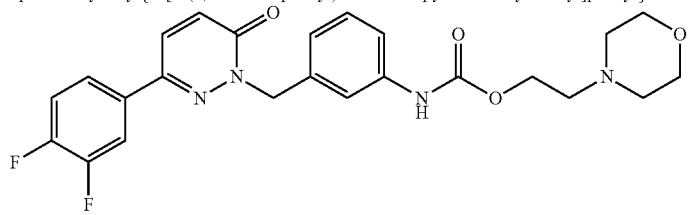 |
| "A82" | 2-Dimethylaminoethyl{3-[3-(3,4-difluorophenyl)-6-oxo-6H-pyridazin-1-ylmethyl]phenyl}carbamate 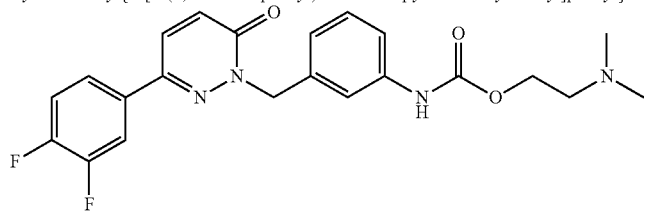 |
| "A83" | 2-Pyrrolidin-1-ylethyl{3-[3-(3,5-difluorophenyl)-6-oxo-6H-pyridazin-1-ylmethyl]phenyl}carbamate 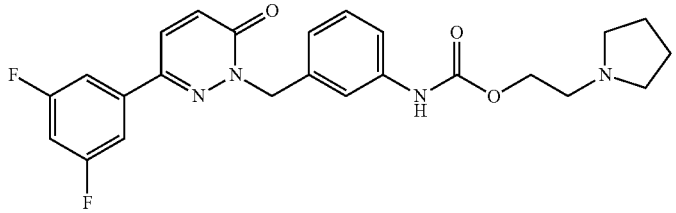 |
| "A84" | 2-Methoxyethyl{3-[3-(3,5-difluorophenyl)-6-oxo-6H-pyridazin-1-ylmethyl]phenyl}carbamate 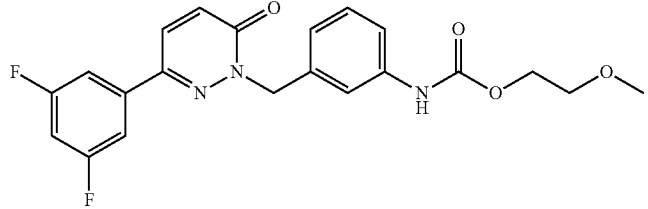 |
| "A85" | 2-Methoxyethyl{3-[3-(3,4-difluorophenyl)-6-oxo-6H-pyridazin-1-ylmethyl]phenyl}carbamate | and pharmaceutically usable salts, tautomers and stereoisomers thereof, including mixtures thereof in all ratios.

10. A compound according to claim 1, selected from the following compounds:

| No. | Structure and/or name |
|---|---|
| "A86" | 3-Morpholin-4-ylpropyl {3-[3-(2,4-difluorophenyl)-6-oxo-6H-pyridazin-1-ylmethyl]phenyl}carbamate |

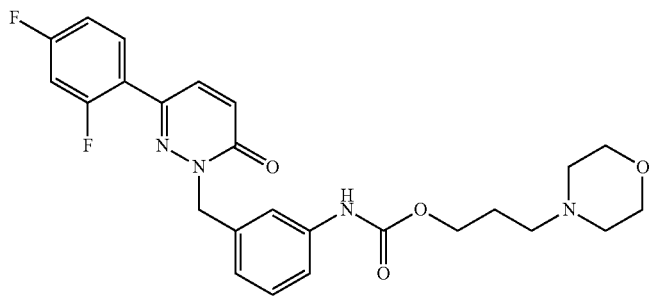

| | |
|---|---|
| "A87" | 3-Morpholin-4-ylpropyl {3-[3-(2,3-difluorophenyl)-6-oxo-6H-pyridazin-1-ylmethyl]phenyl}carbamate |
| "A88" | 3-Morpholin-4-ylpropyl {3-[3-(3-cyanophenyl)-6-oxo-6H-pyridazin-1-ylmethyl]phenyl}carbamate |

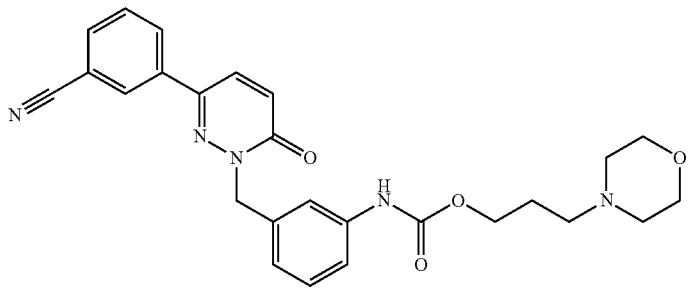

| | |
|---|---|
| "A89" | 2-Morpholin-4-ylethyl {3-[3-(3,4-difluorophenyl)-6-oxo-6H-pyridazin-1-ylmethyl]phenyl}carbamate |

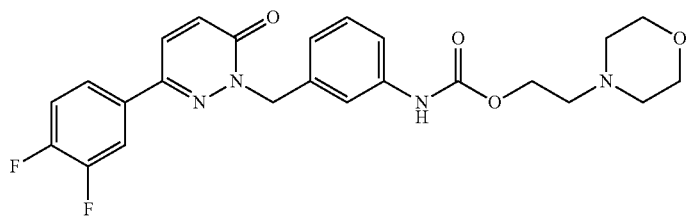

| | |
|---|---|
| "A90" | 3-(4-Methylpiperazin-1-yl)propyl {3-[3-(3,4-difluorophenyl)-6-oxo-6H-pyridazin-1-ylmethyl]phenyl}carbamate |

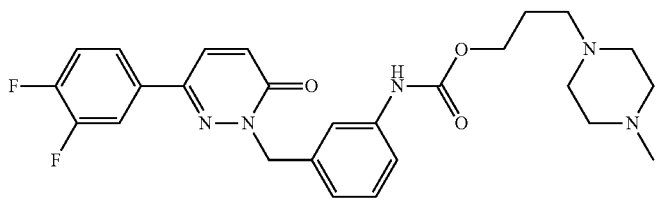

| No. | Structure and/or name |
|---|---|
| "A91" | 3-(4-Methylpiperazin-1-yl)propyl {3-[3-(3,5-difluorophenyl)-6-oxo-6H-pyridazin-1-ylmethyl]phenyl}carbamate |
| "A92" | 2-(4-Methylpiperazin-1-yl)ethyl {3-[3-(3,4-difluorophenyl)-6-oxo-6H-pyridazin-1-ylmethyl]phenyl}carbamate |
| "A93" | 2-(4-Methylpiperazin-1-yl)ethyl {3-[3-(3,5-difluorophenyl)-6-oxo-6H-pyridazin-1-ylmethyl]phenyl}carbamate |
| "A94" | 2-(2-Methoxyethoxy)ethyl {3-[3-(3,5-difluorophenyl)-6-oxo-6H-pyridazin-1-ylmethyl]phenyl}carbamate |
| "A95" | 2-Morpholin-4-ylethyl {3-[6-oxo-3-(3,4,5-trifluorophenyl)-6H-pyridazin-1-ylmethyl]phenyl}carbamate |
| "A96" | 3-Morpholin-4-ylpropyl {3-[3-(3,5-dichlorophenyl)-6-oxo-6H-pyridazin-1-ylmethyl]phenyl}carbamate |

| No. | Structure and/or name |
|---|---|
| "A97" | 2-(2-Methoxyethoxy)ethyl {3-[3-(3,4-difluorophenyl)-6-oxo-6H-pyridazin-1-ylmethyl]phenyl}carbamate |

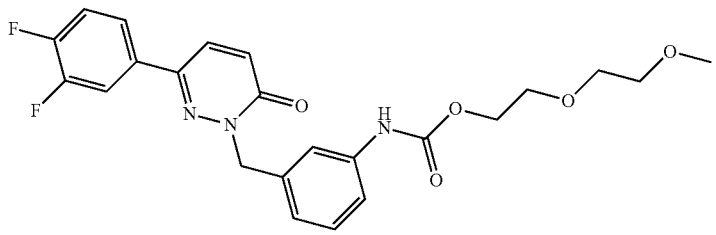

| | |
|---|---|
| "A98" | 1-Methylpiperidin-4-yl {3-[3-(3,5-difluorophenyl)-6-oxo-6H-pyridazin-1-ylmethyl]phenyl}carbamate |

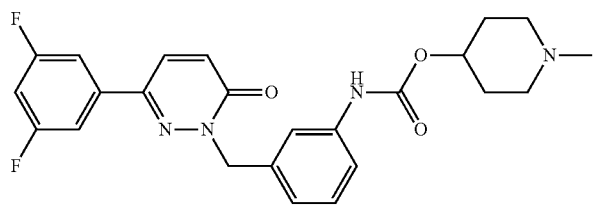

| | |
|---|---|
| "A99" | 1-Methylpiperidin-4-yl {3-[3-(3,4-difluorophenyl)-6-oxo-6H-pyridazin-1-ylmethyl]phenyl}carbamate |
| "A100" | 2-Morpholin-4-ylethyl {3-[3-(4-cyanophenyl)-6-oxo-6H-pyridazin-1-ylmethyl]phenyl}carbamate |

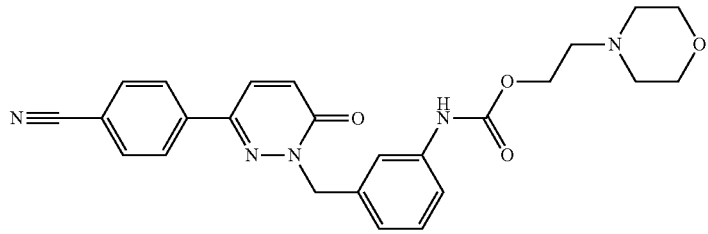

and pharmaceutically usable salts, tautomers and stereoisomers thereof, including mixtures thereof in all ratios.

11. A compound according to claim 1, selected from the following compounds:

| No. | Structure and/or name |
|---|---|
| "A101" | 3-(4-Methylpiperazin-1-yl)propyl {3-[6-oxo-3-(3,4,5-trifluorophenyl)-6H-pyridazin-1-ylmethyl]phenyl}carbamate |

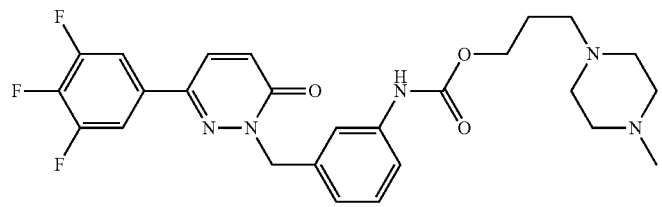

| No. | Structure and/or name |
|---|---|
| "A102" | 4-Dimethylaminobutyl {3-[3-(3,5-difluorophenyl)-6-oxo-6H-pyridazin-1-ylmethyl]phenyl}carbamate 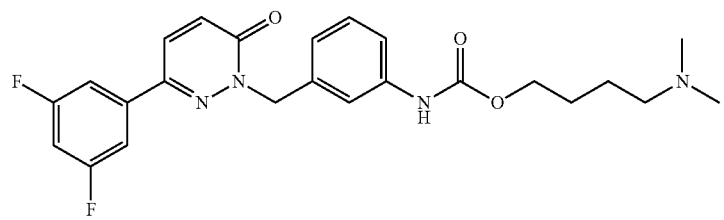 |
| "A103" | 4-(4-Methylpiperazin-1-yl)butyl {3-[3-(3,5-difluorophenyl)-6-oxo-6H-pyridazin-1-ylmethyl]phenyl}carbamate 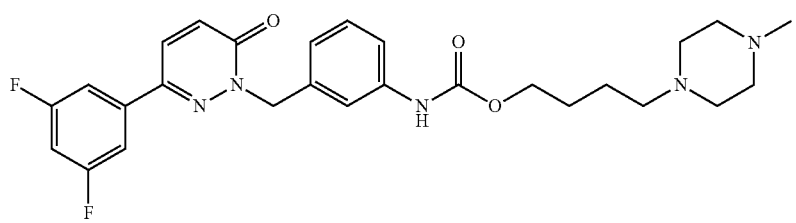 |
| "A104" | 1-Methylpiperidin-4-ylmethyl {3-[3-(3,5-difluorophenyl)-6-oxo-6H-pyridazin-1-ylmethyl]phenyl}carbamate 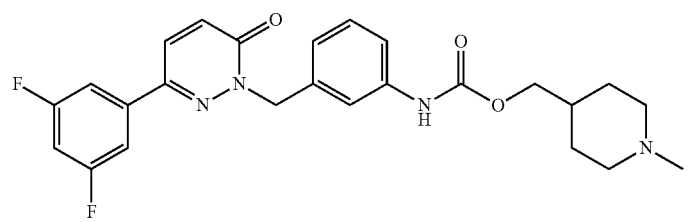 |
| "A105" | 2-(1-Methylpyrrolidin-2-yl)ethyl {3-[3-(3,5-difluorophenyl)-6-oxo-6H-pyridazin-1-ylmethyl]phenyl}carbamate 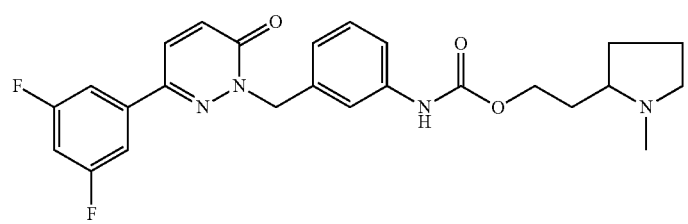 |
| "A106" | 1-Methylpiperidin-3-ylmethyl {3-[3-(3,5-difluorophenyl)-6-oxo-6H-pyridazin-1-ylmethyl]phenyl}carbamate 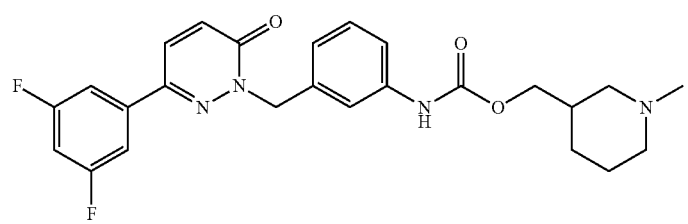 |

-continued

| No. | Structure and/or name |
|---|---|
| "A107" | 3-(4-Methylpiperazin-1-yl)propyl {3-[3-(3-cyanophenyl)-6-oxo-6H-pyridazin-1-ylmethyl]phenyl}carbamate |

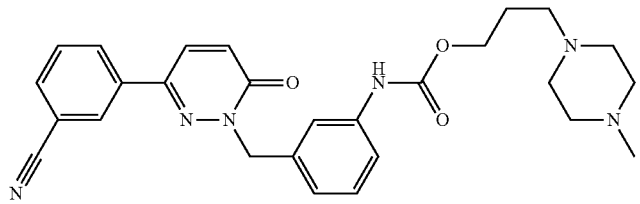

| | |
|---|---|
| "A108" | 3-(2-Methoxyethoxy)propyl {3-[3-(3,5-difluorophenyl)-6-oxo-6H-pyridazin-1-ylmethyl]phenyl}carbamate |

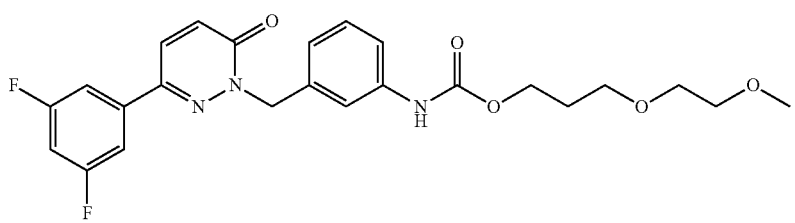

| | |
|---|---|
| "A109" | 3-Diethylaminopropyl {3-[3-(3,5-difluorophenyl)-6-oxo-6H-pyridazin-1-ylmethyl]phenyl}carbamate |

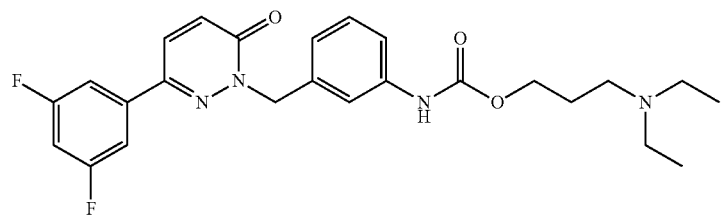

| | |
|---|---|
| "A110" | 4-Dimethylaminobutyl {3-[3-(3,5-difluorophenyl)-6-oxo-6H-pyridazin-1-ylmethyl]phenyl}carbamate |

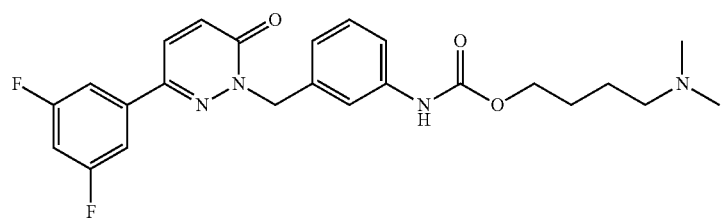

| | |
|---|---|
| "A111" | 3-(2-Methoxyethoxy)propyl {3-[3-(3,4-diflorophenyl)-6-oxo-6H-pyridazin-1-ylmethyl]phenyl}carbamate |

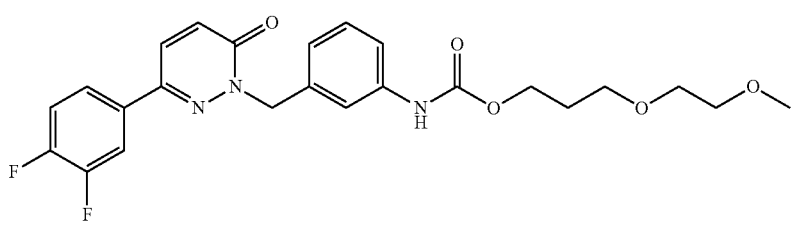

| No. | Structure and/or name |
|---|---|
| "A112" | 4-Dimethylaminobutyl {3-[3-(3,4-difluorophenyl)-6-oxo-6H-pyridazin-1-ylmethyl]phenyl}carbamate |
| "A113" | 2-(4-Methylpiperazin-1-yl)ethyl {3-[6-oxo-3-(3,4,5-trifluoro-phenyl)-6H-pyridazin-1-ylmethyl]phenyl}carbamate |
| "A114" | 2-(3-Aminobenzyl)-6-(3,5-difluorophenyl)-2H-pyridazin-3-one |
| "A115" | 2-(3-Aminobenzyl)-6-(3,4-difluorophenyl)-2H-pyridazin-3-one | and pharmaceutically usable salts, tautomers and stereoisomers thereof, including mixtures thereof in all ratios.

12. A compound according to claim 1, selected from the following compounds:

| No. | Structure and/or name |
|---|---|
| "A116" | 2-(3-Aminobenzyl)-6-(3,4,5-trifluorophenyl)-2H-pyridazin-3-one |
| "A117" | 2-(3-Aminobenzyl)-6-(4-fluorophenyl)-2H-pyridazin-3-one |
| "A118" | 3-[1-(3-Aminobenzyl)-6-oxo-1,6-dihydropyridazin-3-yl]-benzonitrile |
| "A119" | 2-Hydroxyethyl {3-[3-(3,5-difluorophenyl)-6-oxo-6H-pyridazin-1-ylmethyl]phenyl}carbamate |
| "A120" | 2-Hydroxyethyl {3-[3-(3,4-difluorophenyl)-6-oxo-6H-pyridazin-1-ylmethyl]phenyl}carbamate |
| "A121" | 3-[3-(3,5-Difluorophenyl)-6-oxo-6H-pyridazin-1-ylmethyl]benzoic acid |

-continued

| No. | Structure and/or name |
|---|---|
| "A122" | 6-(3,5-Difluorophenyl)-2-[3-(5-methyloxazol-2-yl)benzyl]-2H-pyridazin-3-one |
| "A123" | 6-(3,5-Difluorophenyl)-2-[3-(5-oxo-4,5-dihydro-1,3,4-oxadiazol-2-yl)benzyl]-2H-pyridazin-3-one |
| "A124" | 2-Benzo-1,2,5-thiadiazol-5-ylmethyl-6-(3-fluorophenyl)-2H-pyridazin-3-one |
| "A125" | 2-(2-Amino-1H-benzimidazol-5-ylmethyl)-6-(3-fluorophenyl)-2H-pyridazin-3-one |
| "A126" | 2-(1H-Benzimidazol-5-ylmethyl)-6-(3-fluorophenyl)-2H-pyridazin-3-one |
| "A127" | 5-[3-(3-Fluorophenyl)-6-oxo-6H-pyridazin-1-ylmethyl]-1,3-dihydrobenzimidazol-2-one |
| "A128" | 6-(3,5-Difluorophenyl)-2-(3-hydroxybenzyl)-2H-pyridazin-3-one |
| "A129" | 1-{3-[3-(3,5-Difluorophenyl)-6-oxo-6H-pyridazin-1-ylmethyl]-phenyl}-3-(3-morpholin-4-ylpropyl)urea |
| "A130" | 1-{3-[3-(4-Fluorophenyl)-6-oxo-6H-pyridazin-1-ylmethyl]-phenyl}-3-(1-methylpyrrolidin-3-ylmethyl)urea | and pharmaceutically usable salts, tautomers and stereoisomers thereof, including mixtures thereof in all ratios.

13. A compound according to claim 1, selected from the following compounds:

| No. | Structure and/or name |
|---|---|
| "A131" | 1-{3-[3-(3,5-Difluorophenyl)-6-oxo-6H-pyridazin-1-ylmethyl]-phenyl}-3-(3-pyrrolidin-1-ylpropyl)urea |

| No. | Structure and/or name |
|---|---|
| "A132" | 1-{3-[3-(3,4-Difluorophenyl)-6-oxo-6H-pyridazin-1-ylmethyl]-phenyl}-3-(3-pyrrolidin-1-ylpropyl)urea |
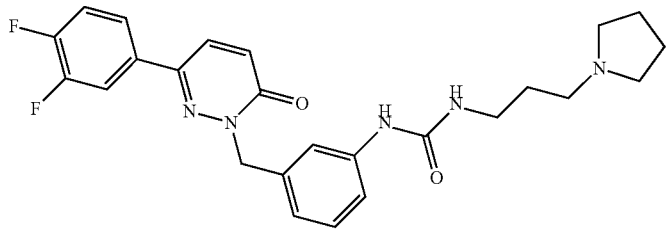
| | |
|---|---|
| "A133" | 3-[3-(3,5-Difluorophenyl)-6-oxo-6H-pyridazin-1-ylmethyl]phenyl (3-dimethylaminopropyl)carbamate |
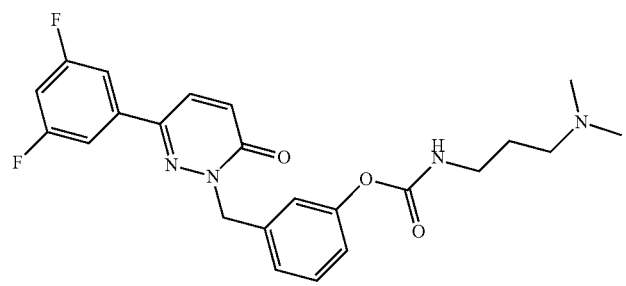
| | |
|---|---|
| "A134" | 1-{3-[3-(3,5-Difluorophenyl)-6-oxo-6H-pyridazin-1-ylmethyl]-phenyl}-3-(3-dimethylaminopropyl)urea |
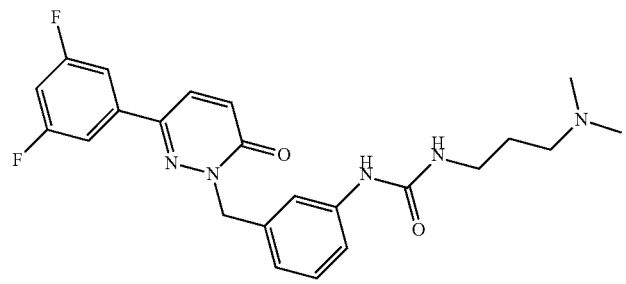
| | |
|---|---|
| "A135" | 1-{3-[3-(3,5-Difluorophenyl)-6-oxo-6H-pyridazin-1-ylmethyl]-phenyl}-3-(2-morpholin-4-ylethyl)urea |
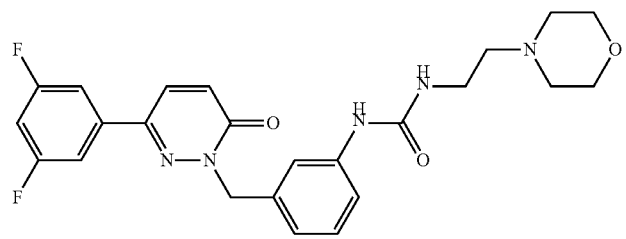

| No. | Structure and/or name |
|---|---|
| "A136" | 1-{3-[3-(3,5-Difluorophenyl)-6-oxo-6H-pyridazin-1-ylmethyl]-phenyl}-3-[3-(4-methylpiperazin-1-yl)propyl]urea 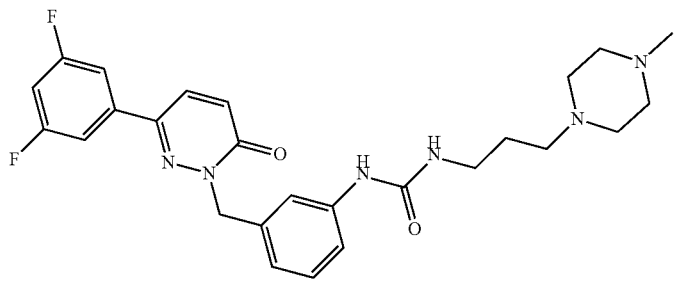 |
| "A137" | 1-{3-[3-(3,4-Difluorophenyl)-6-oxo-6H-pyridazin-1-ylmethyl]-phenyl}-3-(3-dimethylaminopropyl)urea 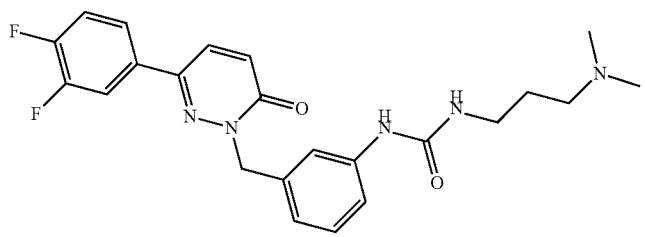 |
| "A138" | 1-{3-[3-(3,4-Difluorophenyl)-6-oxo-6H-pyridazin-1-ylmethyl]-phenyl}-3-(3-morpholin-4-ylpropyl)urea 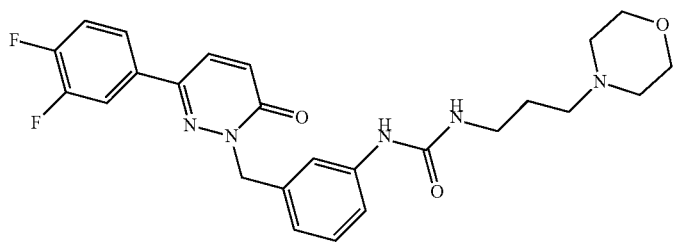 |
| "A139" | 1-{3-[3-(3,4-Difluorophenyl)-6-oxo-6H-pyridazin-1-ylmethyl]-phenyl}-3-(2-morpholin-4-ylethyl)urea 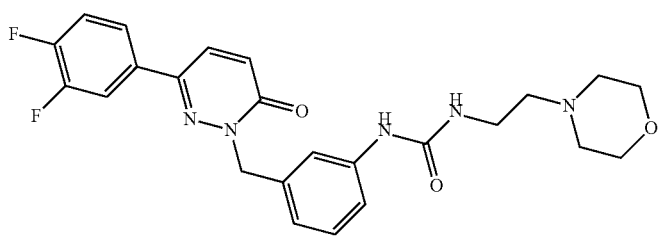 |
| "A140" | 1-{3-[3-(3,4-Difluorophenyl)-6-oxo-6H-pyridazin-1-ylmethyl]-phenyl}-3-[3-(4-methylpiperazin-1-yl)propyl]urea 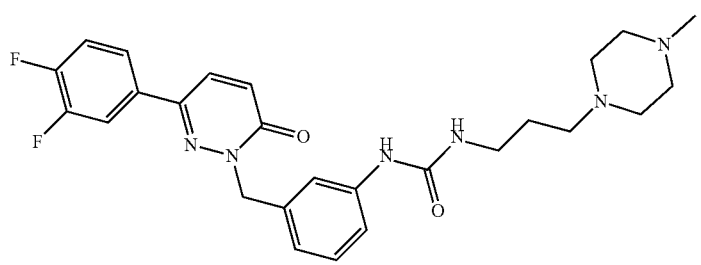 |

| No. | Structure and/or name |
|---|---|
| "A141" | {3-[3-(3,5-Difluorophenyl)-6-oxo-6H-pyridazin-1-ylmethyl]-phenyl}urea |

| "A142" | 3-Methylaminopropyl {3-[3-(3,5-difluorophenyl)-6-oxo-6H-pyridazin-1-ylmethyl]phenyl}carbamate |
|---|---|
| "A143" | 2-Piperazin-1-ylethyl {3-[3-(3,5-difluorophenyl)-6-oxo-6H-pyridazin-1-ylmethyl]phenyl}carbamate |

| "A144" | 3-Piperazin-1-ylpropyl {3-[3-(3,4-difluorophenyl)-6-oxo-6H-pyridazin-1-ylmethyl]phenyl}carbamate |
|---|---|

| "A145" | 3-Piperazin-1-ylpropyl {3-[3-(3,5-difluorophenyl)-6-oxo-6H-pyridazin-1-ylmethyl]phenyl}carbamate |
|---|---| and pharmaceutically usable salts, tautomers and stereoisomers thereof, including mixtures thereof in all ratios.

14. A compound according to claim 1, selected from the following compounds:

| No. | Structure and/or name |
|---|---|
| "A146" | 2-Piperazin-1-ylethyl {3-[3-(3,4-difluorophenyl)-6-oxo-6H-pyridazin-1-ylmethyl]phenyl}carbamate |

-continued

| No. | Structure and/or name |
|---|---|
| "A147" | 3-Methylaminopropyl {3-[3-(3,4-difluorophenyl)-6-oxo-6H-pyridazin-1-ylmethyl]phenyl}carbamate 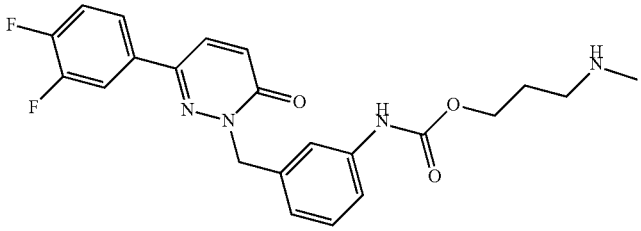 |
| "A148" | 2-Isopropylaminoethyl {3-[3-(3,4-difluorophenyl)-6-oxo-6H-pyridazin-1-ylmethyl]phenyl}carbamate 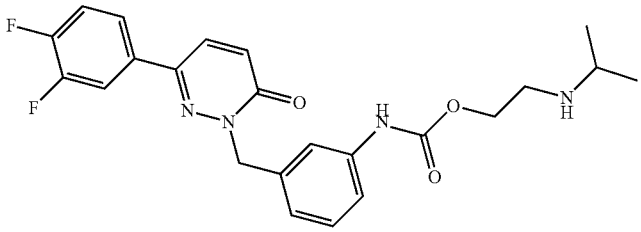 |
| "A149" | 3-Isopropylaminopropyl {3-[3-(3,4-difluorophenyl)-6-oxo-6H-pyridazin-1-ylmethyl]phenyl}carbamate 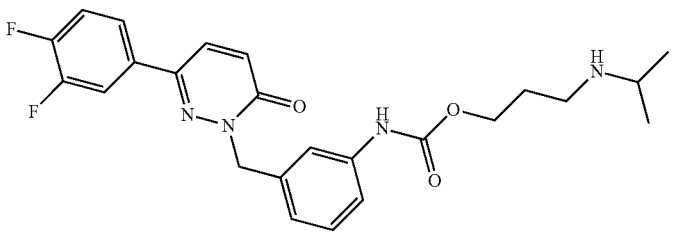 |
| "A150" | 3-Isopropylaminopropyl {3-[3-(3,5-difluorophenyl)-6-oxo-6H-pyridazin-1-ylmethyl]phenyl}carbamate 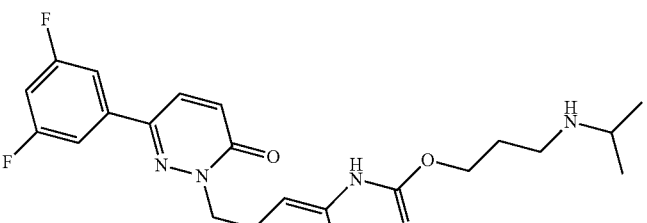 |
| "A151" | 2-Methylaminoethyl {3-[3-(3,4-difluorophenyl)-6-oxo-6H-pyridazin-1-ylmethyl]phenyl}carbamate 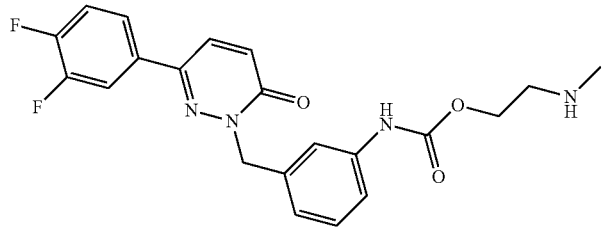 |

-continued

| No. | Structure and/or name |
|---|---|
| "A152" | 2-Methylaminoethyl {3-[3-(3,5-difluorophenyl)-6-oxo-6H-pyridazin-1-ylmethyl]phenyl}carbamate |

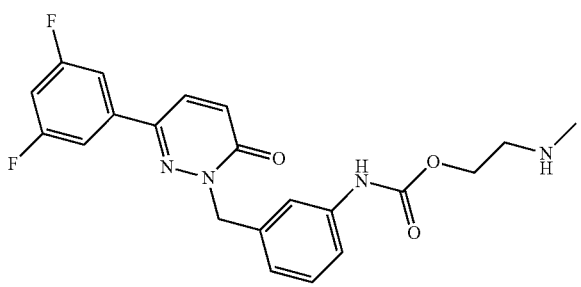

| "A153" | 2-Isopropylaminoethyl {3-[3-(3,5-difluorophenyl)-6-oxo-6H-pyridazin-1-ylmethyl]phenyl}carbamate |
|---|---|

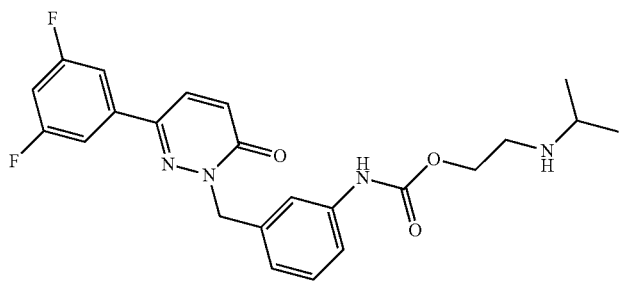

| "A154" | 3-Methylaminopropyl {3-[3-(4-cyanophenyl)-6-oxo-6H-pyridazin-1-ylmethyl]phenyl}carbamate |
|---|---|

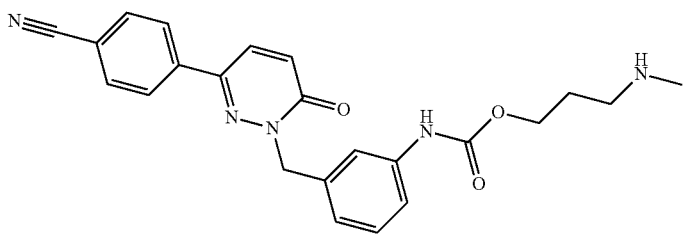

| "A155" | 4-Methylaminobutyl {3-[3-(3,5-difluorophenyl)-6-oxo-6H-pyridazin-1-ylmethyl]phenyl}carbamate |
|---|---|

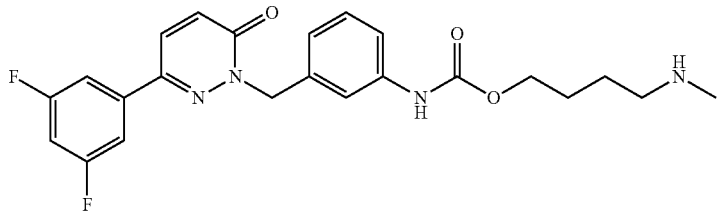

| "A156" | Piperidin-4-ylmethyl {3-[3-(3,5-difluorophenyl)-6-oxo-6H-pyridazin-1-ylmethyl]phenyl}carbamate |
|---|---|

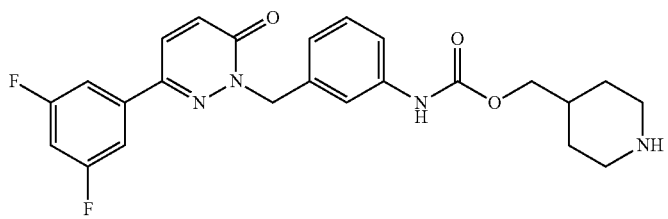

| No. | Structure and/or name |
|---|---|
| "A157" | Piperidin-3-ylmethyl {3-[3-(3,5-difluorophenyl)-6-oxo-6H-pyridazin-1-ylmethyl]phenyl}carbamate |

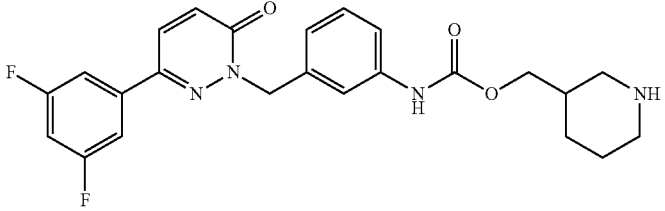

and pharmaceutically usable salts, tautomers and stereoisomers thereof, including mixtures thereof in all ratios.

15. A compound according to claim 1, selected from the following compounds:

| No. | Structure and/or name |
|---|---|
| "A158" | 6-[3-(3,5-Difluorophenyl)-6-oxo-6H-pyridazin-1-ylmethyl]-1-(3-dimethylaminopropyl)-1,3-dihydrobenzimidazol-2-one |
| "A159" | 6-[3-(3,5-Difluorophenyl)-6-oxo-6H-pyridazin-1-ylmethyl]-1-(2-dimethylaminoethyl)-1,3-dihydrobenzimidazol-2-one |

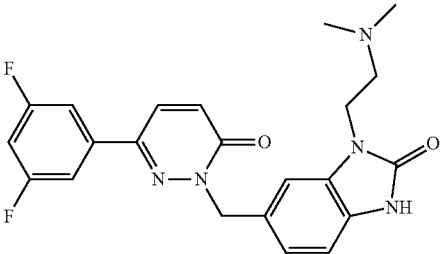

| | |
|---|---|
| "A160" | 6-[3-(3,5-Difluorophenyl)-6-oxo-6H-pyridazin-1-ylmethyl]-1-(4-dimethylaminobutyl)-1,3-dihydrobenzimidazol-2-one |

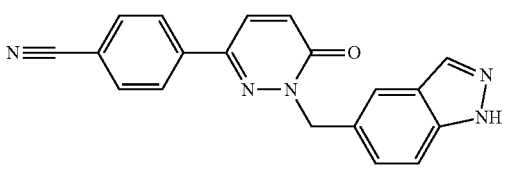

| | |
|---|---|
| "A161" | 6-(3,5-Difluorophenyl)-2-(1H-indazol-5-ylmethyl)-2H-pyridazin-3-one |
| "A162" | 4-[1-(1H-Indazol-5-ylmethyl)-6-oxo-1,6-dihydropyridazin-3-yl]-benzonitrile |

| | |
|---|---|
| "A163" | 6-(3,5-Difluorophenyl)-2-(1-oxyquinolin-6-ylmethyl)-2H-pyridazin-3-one |
| "A164" | 6-[3-(3,5-Difluorophenyl)-6-oxo-6H-pyridazin-1-ylmethyl]-1H-quinolin-2-one |
| "A165" | 2-(3-Amino-1H-indazol-5-ylmethyl)-6-(3,5-difluorophenyl)-2H-pyridazin-3-one |

| No. | Structure and/or name |
|---|---|
| "A166" | 3-(4-Methylpiperazin-1-yl)propyl {3-[3-(3-carbamoylphenyl)-6-oxo-6H-pyridazin-1-ylmethyl]phenyl}carbamate |
| "A167" | 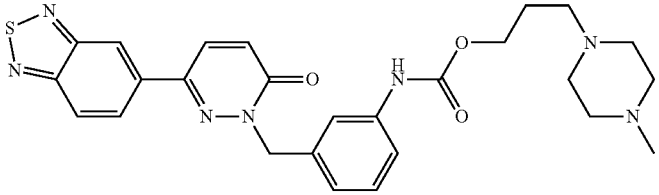 |
| "A168" | 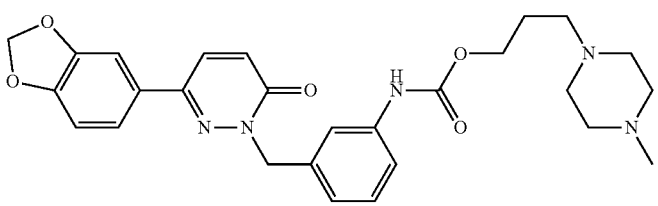 |
| "A169" | 5-[3-(3,5-Difluorophenyl)-6-oxo-6H-pyridazin-1-ylmethyl]-1,3-dihydrobenzimidazol-2-one 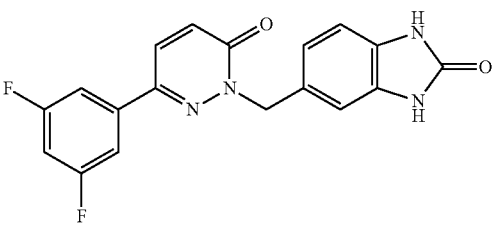 | and pharmaceutically usable salts, tautomers and stereoisomers thereof, including mixtures thereof in all ratios.

16. A composition comprising at least one compound of according to claim 1 and/or pharmaceutically usable salts, tautomers and stereoisomers thereof, including mixtures thereof in all ratios, and at least one excipient and/or adjuvant.

\* \* \* \* \*

UNITED STATES PATENT AND TRADEMARK OFFICE
CERTIFICATE OF CORRECTION

Page 1 of 1

PATENT NO. : 8,173,653 B2
APPLICATION NO. : 12/096079
DATED : May 8, 2012
INVENTOR(S) : Dieter Dorsch et al.

It is certified that error appears in the above-identified patent and that said Letters Patent is hereby corrected as shown below:

Column 128, Line 56, Claim 2 reads:
"3-(4-Methylpiperazin-1-yl)propyl }3-[3-(3-cyanophenyl)-6-oxo-" should read
-- 3-(4-Methylpiperazin-1-yl)propyl {3-[3-(3-cyanophenyl)-6-oxo- --.

Signed and Sealed this
Twenty-seventh Day of November, 2012

David J. Kappos
*Director of the United States Patent and Trademark Office*